US012076369B2

(12) United States Patent
Garcia De Vinuesa De La Concha et al.

(10) Patent No.: US 12,076,369 B2
(45) Date of Patent: Sep. 3, 2024

(54) IMMUNOREGULATORY MOLECULES AND USES THEREFOR

(71) Applicant: The Frances Crick Institute Limited, London (GB)

(72) Inventors: Maria Carola Garcia De Vinuesa De La Concha, Lyons (AU); Paula Carolina Cecilia Gonzalez-Figueroa, Acton (AU)

(73) Assignee: The Frances Crick Institute Limited, London (GB)

( * ) Notice: Subject to any disclaimer, the term of this patent is extended or adjusted under 35 U.S.C. 154(b) by 0 days.

(21) Appl. No.: 16/642,769

(22) PCT Filed: Aug. 31, 2018

(86) PCT No.: PCT/AU2018/050944
§ 371 (c)(1),
(2) Date: Feb. 27, 2020

(87) PCT Pub. No.: WO2019/040994
PCT Pub. Date: Mar. 7, 2019

(65) Prior Publication Data
US 2021/0196792 A1    Jul. 1, 2021

(30) Foreign Application Priority Data
Sep. 1, 2017 (AU) .............................. 2017903538

(51) Int. Cl.
*A61K 38/18* (2006.01)
*A61K 47/60* (2017.01)

(52) U.S. Cl.
CPC ............ *A61K 38/185* (2013.01); *A61K 47/60* (2017.08)

(58) Field of Classification Search
None
See application file for complete search history.

(56) References Cited

U.S. PATENT DOCUMENTS

2008/0227745 A1    9/2008  Becker et al.

FOREIGN PATENT DOCUMENTS

| WO | WO 1998/006843 | 2/1998 |
| WO | WO 2007/095113 | 8/2007 |
| WO | WO 2007/030820 | 3/2017 |

OTHER PUBLICATIONS

Genecards (https://www.genecards.org/cgi-bin/carddisp.pl?gene=NRN1 accessed Nov. 6, 2021).*
Barbi, J., et al., "Neuritin promotes the expansion and persistence of regulatory T cells in vitro and in vivo", Journal of Immunology, May 2013, vol. 190, Supplement 1, p. 139.15, Abstract No. P1051.
Barbi, J. et al., "Neuritin Bolsters the Regulatory T Cell Pool and Suppresses the Severity of Experimental Colitis", Inflammatory Bowel Diseases, Dec. 2014, vol. 20, Supplement No. 1, p. S91, Abstract No. P-156.
Barbi, J., et al., "The Neurotrophic Factor Neuritin Maintains and Promotes the Function of Regulatory T cells in Autoimmunity and Cancer", Journal of Immunology, May 2016, vol. 196, Supplement No. 1, p. 58.12.
Cooper, J.J.M., et al., "Neuritin is Required for T Regulatory Cell-Mediated Suppression of the Long-Lived Plasma Cell Niche", Journal of Immunology, May 2018, vol. 200, Supplement No. 1, p. 107.6.
Dong, H., et al., "Neuritin 1 expression in human normal tissues and its association with various human cancers", International Journal of Clinical and Experimental Pathology, Apr. 2018, vol. 11, No. 4, pp. 1956-1964.
Li, J., et al., "Oxidative stress induced neural neuritin reduction is associated with peripheral nerve dysfunction in diabetic rats", Diabetologia, Aug. 2016, vol. 59, Supplement No. 1, p. S460, Abstract No. 954.
International Search Report and Written Opinion for PCT/AU2018/050944, mailed Nov. 14, 2018, 13 pages.

* cited by examiner

*Primary Examiner* — Julie Ha
*Assistant Examiner* — Tara L Martinez
(74) *Attorney, Agent, or Firm* — Casimir Jones, S.C.; Mary Ann D. Brow

(57) ABSTRACT

Disclosed are agents and methods for treating unwanted or deleterious immune responses. More particularly, the present invention discloses neuritin agents for use in inhibiting plasma cell (PC) differentiation, reducing the number of autoreactive B cells, treating, or inhibiting the development or progression of, autoreactive B cell disorders including B cell-mediated autoimmune diseases and IgE-mediated disorders and of monoclonal gammopathies and PC dyscrasias.

14 Claims, 15 Drawing Sheets

Specification includes a Sequence Listing.

FIGURE 13

| ID | Name | Sequence | |
|---|---|---|---|
| G1RL84 | G1RL84_NOMLE | 1 | MGLKLNGRYISLILAVQIAYLVQAVRAAGKCDAVFKGFSDCLLKLGDSMANYPQGLDDDKT | 60 |
| A0A0D9R4S6 | A0A0D9R4S6_CHLSB | 1 | MGLKLNGRYISLILAVQIAYLVQAVRAAGKCDAVFKGFSDCLLKLGDSMANYPQGLDDDKT | 60 |
| H2PBU4 | H2PHU4_PONAB | 1 | MGLKLNGRYISLILAVQIAYLVQAVRAAGKCDAVFKGFSDCLLKLGDSMANYPQGLDDDKT | 60 |
| G3QR76 | G3QR76_GORGO | 1 | MGLKLNGRYISLILAVQIAYLVQAVRAAGKCDAVFKGFSDCLLKLGDSMANYPQGLDDDKT | 60 |
| H2QS91 | H2QS91_PANTR | 1 | MGLKLNGRYISLILAVQIAYLVQAVRAAGKCDAVFKGFSDCLLKLGDSMANYPQGLDDDKT | 60 |
| Q9NPD7 | NRN1_HUMAN | 1 | MGLKLNGRYISLILAVQIAYLVQAVRAAGKCDAVFKGFSDCLLKLGDSMANYPQGLDDDKT | 60 |
| A0A096NKQ3 | A0A096NKQ3_PAPAN | 1 | MGLKLNGRYISLILAVQIAYLVQAVRAAGKCDAVFKGFSDCLLKLGDSMANYPQGLDDDKT | 60 |
| M3X8K3 | M3X8K3_FELCA | 1 | MGLKLNGRYISLILAVQIAYLVQAVRAAGKCDAVFKGFSDCLLKLGDSMANYPQGLDDDKT | 60 |
| G1MGEJ | G1MGE3_AILME | 1 | MGLKLNGRYISLILAVQIAYLVQAVRAAGKCDAVFKGFSDCLLKLGDSMANYPQGLDDDKT | 60 |
| G7P4C7 | G7P4C7_MACFA | 1 | MGLKLNGRYISLILAVQIAYLVQAVRAAGKCDAVFKGFSDCLLKLGDSMANYPQGLDDDKT | 60 |
| F7HEM3 | F7BEM3_CALJA | 1 | MGLKLNGRYISLILAVQIAYLVQAVRAAGKCDAVFKGFSDCLLKLGDSMANYPQGLDDDKT | 60 |
| F6SIB8 | F6SIB8_MACMU | 1 | MGLKLNGRYISLILAVQIAYLVQAVRAAGKCDAVFKGFSDCLLKLGDSMANYPQGLDDDKT | 60 |
| E2RK66 | E2RK66_CANLE | 1 | MGLKLNGRYISLILAVQIAYLVQAVRAAGKCDAVFKGFSDCLLKLGDSMANYPQGLDDDKT | 60 |
| F1RW81 | F1RW81_PIG | 1 | MGLKLNGRYISLILAVQIAYLVQAVRAAGKCDAVFKGFSDCLLKLGDSMANYPQGLDDDKT | 60 |
| L5KUZ4 | L5KUZ4_PTEAL | 1 | MGLKLNGRYISLILAVQIAYLVQAVRAAGKCDAVFKGFSDCLLKLGDSMANYPQGLDDDKT | 60 |
| A0A1S3F647 | A0A1S3F647_DIPOR | 1 | MGLKLNGRYISLILAVQIAYLVQAVRAAGKCDAVFKGFSDCLLKLGDSMANYPQGLDDDKT | 60 |
| F7DF40 | F7DF40_HORSE | 1 | MGLKLNGRYISLILAVQIAYLVQAVRAAGKCDAVFKGFSDCLLKLGDSMANYPQGLDDDKT | 60 |
| U6CV18 | U6CV18_NEOVI | 1 | MGLKLNGRYISLILAVQIAYLVQAVRAAGKCDAVFKGFSDCLLKLGDSMANYPQGLDDDKT | 60 |
| A0A1U7UID3 | A0A1U7UID3_TARSY | 1 | MGLKLNGRYISLILAVQIAYLVQAVRAAGKCDAVFKGFSDCLLKLGDSMANYPQGLDDDKT | 60 |
| A0A1U7Q3RO | A0A1U7Q3RO_MESAU | 1 | MGLKLNGRYISLILAVQIAYLVQAVRAAGKCDAVFKGFSDCLLKLGDSMANYPQGLDDDKT | 60 |
| HOXRS4 | HOXRS4_OTOGA | 1 | MGLKLNGRYISLILAVQIAYLVQAVRAAGKCDAVFKGFSDCLLKLGDSMANYPQGLDDDKT | 60 |
| O08957 | NRN1_RAT | 1 | MGLKLNGRYISLILAVQIAYLVQAVRAAGKCDAVFKGFSDCLLKLGDSMANYPQGLDDDKT | 60 |
| Q2KIC6 | NRN1_BOVIN | 1 | MGLKLNGRYISLILAVQIAYLVQAVRAAGKCDAVFKGFSDCLLKLGDSMANYPQGLDDDKT | 60 |
| A0A1A6HJB8 | A0A1A6HJB8_NEOLE | 1 | MGLKLNGRYISLILAVQIAYLVQAVRAAGKCDAVFKGFSDCLLKLGDSMANYPQGLDDDKT | 60 |
| W5QBC3 | W5QBC3_SHEEP | 1 | MGLKLNGRYISLILAVQIAYLVQAVRAAGKCDAVFKGFSDCLLKLGDSMANYPQGLDDDKT | 60 |
| | | | ************************************************************ |

FIGURE 13 (continued)

| | | | |
|---|---|---|---|
| G1RL84 | G1RL84_NOMLE | 61 | NIKTVCTYWEDFHSCTVTALTDCQEGAKIMDKLRKESKNLNIQGSLFELCGSGNGAAGS 120 |
| A0A0D9R4S6 | A0A0D9R4S6_CHLSB | 61 | NIKTVCTYWEDFHSCTVTALTDCQEGAKIMDKLRKESKNLNIQGSLFELCGSGNGAAGS 120 |
| H2PBU4 | H2PHU4_PONAB | 61 | NIKTVCTYWEDFHSCTVTALTDCQEGAKIWDKLRKESKNLNIQGSLFELCGSGNGAAGS 120 |
| G3QR76 | G3QR76_GORGO | 61 | NIKTVCTYWEDFHSCTVTALTDCQEGAKIMDKLRKESKNLNIQGSLFELCGSGNGAAGS 120 |
| H2QS91 | H2QS91_PANTR | 61 | NIKTVCTYWEDFHSCTVTALTDCQEGAKIMDKLRKESKNLNIQGSLFELCGSGNGAAGS 120 |
| Q9NPD7 | NRN1_HUMAN | 61 | NIKTVCTYWEDFHSCTVTALTDCQEGAKIMDKLRKESKNLNIQGSLFELCGSGNGAAGS 120 |
| A0A096NKQ3 | A0A096NKQ3_PAPAN | 61 | NIKTVCTYWEDFHSCTVTALTDCQEGAKIMDKLRKESKNLNIQGSLFELCGSGNGAAGS 120 |
| M3X8K3 | M3X8K3_FELCA | 61 | NIKTVCTYWEDFHSCTVTALTDCQEGAKIMDKLRKESKNLNIQGSLFELCGSGNGAAGS 120 |
| G1MGEJ | G1MGE3_AILME | 61 | NIKTVCTYWEDFHSCTVTALTDCQEGAKIMDKLRKESKNLNIQGSLFELCGSGNGAAGS 120 |
| G7P4C7 | G7P4C7_MACFA | 61 | NIKTVCTYWEDFHSCTVTALTDCQEGAKIMDKLRKESKNLNIQGSLFELCGSGNGAAGS 120 |
| F7HEM3 | F7BEM3_CALJA | 61 | NIKTVCTYWEDFHSCTVTALTDCQEGAKIMDKLRKESKNLNIQGSLFELCGSGNGAAGS 120 |
| F6SIB8 | F6SIB8_MACMU | 61 | NIKTVCTYWEDFHSCTVTALTDCQEGAKIMDKLRKESKNLNIQGSLFELCGSGNGAAGS 120 |
| E2RK66 | E2RK66_CANLF | 61 | NIKTVCTYWEDFHSCTVTALTDCQEGAKIMDKLRKESKNLNIQGSLFELCGSGNGAAGS 120 |
| F1RW81 | F1RW81_PIG | 61 | NIKTVCTYWEDFHSCTVTALTDCQEGAKIMDKLRKESKNLNIQGSLFELCGSGNGAAGS 120 |
| L5KUZ4 | L5KUZ4_PTEAL | 61 | NIKTVCTYWEDFHSCTVTALTDCQEGAKIMDKLRKESKNLNIQGSLFELCGSGNGAAGS 120 |
| A0A1S3F647 | A0A1S3F647_DIPOR | 61 | NIKTVCTYWEDFHSCTVTALTDCQEGAKIMDKLRKESKNLNIQGSLFELCGSGNGAAGP 120 |
| F7DF40 | F7DF40_HORSE | 61 | NIKTVCTYWEDFHSCTVTALTDCQEGAKIMDKLRKESKNLNIQGSLFELCGSGNGAAGS 120 |
| U6CV18 | U6CV18_NEOVI | 61 | NIKTVCTYWEDFHSCTVTALTDCQEGAKIMDKLRKESKNLNIQGSLFELCGSGNGAAGS 120 |
| A0A1U7UID3 | A0A1U7UID3_TARSY | 61 | NIKTVCTYWEDFHSCTVTALTDCQEGAKIMDKLRKESKNLNFQGSLFELCGSGNGAAGS 120 |
| A0A1U7Q3RO | A0A1U7Q3RO_MESAU | 61 | NIKTVCTYWEDFHSCTVTALTDCQEGAKIMDKLRKESKNLNIQGSLFELCGSGNGAAGS 120 |
| HOXRS4 | HOXRS4_OTOGA | 61 | NIKTVCTYWEDFHSCTVTALTDCQEGAKIMDKLRKESKNLNIQGSLFELCGSGNGAAGS 120 |
| O08957 | NRN1_RAT | 61 | NIKTVCTYWEDFHSCTVTALTDCQEGAKIMDKLRKESKNLNIQGSLFELCGSGNGAAGS 120 |
| Q2KIC6 | NRN1_BOVIN | 61 | NIKTVCTYWEDFHSCTVTALTDCQEGAKIMDKLRKESKNLNIQGSLFELCGTGNGAAGP 120 |
| A0A1A6HJB8 | A0A1A6HJB8_NEOLE | 61 | NIKTVCTYWEDFHSCTVTALTDCQEGAKIMDKLRKESKNLNIQGSLFELCGGGNGAAGP 120 |
| W5QBC3 | W5QBC3_SHEEP | 61 | NIKTVCTYWEDFHSCTVTALTDCQEGAKIMDKLRKESKNLNIQGSLFELCGGGNGAAGP 120 |
| | | | ************************ ************ ****** :* *:*****. |

FIGURE 13 (continued)

| | | | |
|---|---|---|---|
| G1RL84 G1RL84_NOMLE | 121 | HLPAFPVLIVSLSAALATWLSF | 142 |
| A0A0D9R4S6 A0A0D9R4S6_CHLSB | 121 | HLPAFPVLIVSLSAALATWLSF | 142 |
| H2PBU4 H2PHU4_PONAB | 121 | HLPAFPVLIVSLSAALATWLSF | 142 |
| G3QR76 G3QR76_GORGO | 121 | HLPAFPVLIVSLSAALATWLSF | 142 |
| H2QS91 H2QS91_PANTR | 121 | HLPAFPVLIVSLSAALATWLSF | 142 |
| Q9NPD7 NRN1_HUMAN | 121 | HLPAFPVLIVSLSAALATWLSF | 142 |
| A0A096NKQ3 A0A096NKQ3_PAPAN | 121 | HLPALPVLIVSLSAALATWLSF | 142 |
| M3X8K3 M3X8K3_FELCA | 121 | HLPALPVLIVSLSAALATWLSF | 142 |
| G1MGEJ G1MGE3_AILME | 121 | HLPALPVLIVSLSAALATWLSF | 142 |
| G7P4C7 G7P4C7_MACFA | 121 | HLPALPVLIVSLSAALATWLSF | 142 |
| F7HEM3 F7BEM3_CALJA | 121 | HLPALPVLIVSLSAALATWLSF | 142 |
| F6SIB8 F6SIB8_MACMU | 121 | HLPALPVLIVSLSAALATWLSF | 142 |
| E2RK66 E2RK66_CANLF | 121 | HLPALPVLIVSLSAALATWLSF | 142 |
| F1RW81 F1RW81_PIG | 121 | HLPALPVLIIVALSAALATWLSF | 142 |
| L5KUZ4 L5KUZ4_PTEAL | 121 | LFPALPVLIIVSLSAALATWLSF | 142 |
| A0A1S3F647 A0A1S3F647_DIPOR | 121 | HLPALPVLIMSLSAALATWLSF | 142 |
| F7DF40 F7DF40_HORSE | 121 | HLPALPTLPVLMSLSAALATWLSF | 142 |
| U6CV18 U6CV18_NEOVI | 121 | HLPALSVLIVSLSAALATWLSF | 142 |
| A0A1U7UID3 A0A1U7UID3_TARSY | 121 | HLPALSVLIVSLSAALATWLSF | 142 |
| A0A1U7Q3RO A0A1U7Q3RO_MESAU | 121 | HLPALPVLIVSLSAALATWLSF | 142 |
| HOXRS4 HOXRS4_OTOGA | 121 | LFPALPVLIVSLSAALATWLSF | 142 |
| O08957 NRN1_RAT | 121 | HLPALSVLIVSLSAALATWLSF | 142 |
| Q2KIC6 NRN1_BOVIN | 121 | HLPALSVLIVSLSAALATWLSF | 142 |
| A0A1A6HJB8 A0A1A6HJB8_NEOLE | 121 | HLPALSVLIVSLSAALAAWLSF | 142 |
| W5QBC3 W5QBC3_SHEEP | 121 | HLPALPVLIVSLSAALAAWLSF | 142 |

SEQUENCE LISTING

```
<160> NUMBER OF SEQ ID NOS: 30

<210> SEQ ID NO 1
<211> LENGTH: 429
<212> TYPE: DNA
<213> ORGANISM: Homo sapiens
```

<400> SEQUENCE: 1

```
atgggactta agttgaacgg cagatatatt tcactgatcc tcgcggtgca aatagcgtat      60
ctggtgcagg ccgtgagagc agcgggcaag tgcgatgcgg tcttcaaggg cttttcggac    120
tgtttgctca agctgggcga cagcatggcc aactacccgc agggcctgga cgacaagacg    180
aacatcaaga ccgtgtgcac atactgggag gatttccaca gctgcacggt cacagccctt    240
acggattgcc aggaagggc gaaagatatg tgggataaac tgagaaaaga tccaaaaac     300 ctcaacatcc aaggcagctt attcgaactc tgcggcagcg gcaacggggc ggcggggtcc    360
ctgctcccgg cgttcccggt gctcctggtg tctctctcgg cagctttagc gacctggctt    420
tccttctga                                                             429
```

<210> SEQ ID NO 2
<211> LENGTH: 142
<212> TYPE: PRT
<213> ORGANISM: Homo sapiens

<400> SEQUENCE: 2

```
Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
    50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
            100                 105                 110

Ser Gly Asn Gly Ala Ala Gly Ser Leu Leu Pro Ala Phe Pro Val Leu
        115                 120                 125

Leu Val Ser Leu Ser Ala Ala Leu Ala Thr Trp Leu Ser Phe
    130                 135                 140
```

<210> SEQ ID NO 3
<211> LENGTH: 348
<212> TYPE: DNA
<213> ORGANISM: Homo sapiens

<400> SEQUENCE: 3

```
gcgggcaagt gcgatgcggt cttcaagggc ttttcggact gtttgctcaa gctgggcgac      60
agcatggcca actacccgca gggcctggac gacaagacga acatcaagac cgtgtgcaca    120
tactgggagg atttccacag ctgcacggtc acagccctta cggattgcca ggaaggggcg    180
aaagatatgt gggataaact gagaaaagaa tccaaaaacc tcaacatcca aggcagctta    240
ttcgaactct gcggcagcgg caacggggcg gcggggtccc tgctcccggc gttcccggtg    300
ctcctggtgt ctctctcggc agctttagcg acctggcttt ccttctga                  348
```

<210> SEQ ID NO 4
<211> LENGTH: 115
<212> TYPE: PRT
<213> ORGANISM: Homo sapiens

<400> SEQUENCE: 4

Ala Gly Lys Cys Asp Ala Val Phe Lys Gly Phe Ser Asp Cys Leu Leu
1               5                   10                  15

Lys Leu Gly Asp Ser Met Ala Asn Tyr Pro Gln Gly Leu Asp Asp Lys
            20                  25                  30

Thr Asn Ile Lys Thr Val Cys Thr Tyr Trp Glu Asp Phe His Ser Cys
        35                  40                  45

Thr Val Thr Ala Leu Thr Asp Cys Gln Glu Gly Ala Lys Asp Met Trp
    50                  55                  60

Asp Lys Leu Arg Lys Glu Ser Lys Asn Leu Asn Ile Gln Gly Ser Leu
65                  70                  75                  80

Phe Glu Leu Cys Gly Ser Gly Asn Gly Ala Ala Gly Ser Leu Leu Pro
                85                  90                  95

Ala Phe Pro Val Leu Leu Val Ser Leu Ser Ala Ala Leu Ala Thr Trp
            100                 105                 110

Leu Ser Phe
        115

<210> SEQ ID NO 5
<211> LENGTH: 267
<212> TYPE: DNA
<213> ORGANISM: Homo sapiens

<400> SEQUENCE: 5
gcgggcaagt gcgatgcggt cttcaagggc ttttcggact gtttgctcaa gctgggcgac     60
agcatggcca actacccgca gggcctggac gacaagacga acatcaagac cgtgtgcaca    120
tactgggagg atttccacag ctgcacggtc acagccctta cggattgcca ggaaggggcg    180
aaagatatgt gggataaact gagaaaagaa tccaaaaacc tcaacatcca aggcagctta    240
ttcgaactct gcggcagcgg caacggg                                        267

<210> SEQ ID NO 6
<211> LENGTH: 89
<212> TYPE: PRT
<213> ORGANISM: Homo sapiens

<400> SEQUENCE: 6

Ala Gly Lys Cys Asp Ala Val Phe Lys Gly Phe Ser Asp Cys Leu Leu
1               5                   10                  15

Lys Leu Gly Asp Ser Met Ala Asn Tyr Pro Gln Gly Leu Asp Asp Lys
            20                  25                  30

Thr Asn Ile Lys Thr Val Cys Thr Tyr Trp Glu Asp Phe His Ser Cys
        35                  40                  45

Thr Val Thr Ala Leu Thr Asp Cys Gln Glu Gly Ala Lys Asp Met Trp
    50                  55                  60

Asp Lys Leu Arg Lys Glu Ser Lys Asn Leu Asn Ile Gln Gly Ser Leu
65                  70                  75                  80

Phe Glu Leu Cys Gly Ser Gly Asn Gly
                85

<210> SEQ ID NO 7
<211> LENGTH: 142
<212> TYPE: PRT
<213> ORGANISM: Nomascus leucogenys

```
<400> SEQUENCE: 7

Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
    50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
            100                 105                 110

Ser Gly Asn Gly Ala Ala Gly Ser Leu Leu Pro Ala Phe Pro Val Leu
        115                 120                 125

Leu Val Ser Leu Ser Ala Ala Leu Ala Thr Trp Leu Ser Phe
    130                 135                 140

<210> SEQ ID NO 8
<211> LENGTH: 142
<212> TYPE: PRT
<213> ORGANISM: Chlorocebus sabaeus

<400> SEQUENCE: 8

Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
    50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
            100                 105                 110

Ser Gly Asn Gly Ala Ala Gly Ser Leu Leu Pro Ala Phe Pro Val Leu
        115                 120                 125

Leu Val Ser Leu Ser Ala Ala Leu Ala Thr Trp Leu Ser Phe
    130                 135                 140

<210> SEQ ID NO 9
<211> LENGTH: 142
<212> TYPE: PRT
<213> ORGANISM: Pongo abelii

<400> SEQUENCE: 9

Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30
```

```
Ala Val Phe Lys Gly Phe Ser Asp Cys Leu Leu Lys Leu Gly Asp Ser
            35                  40                  45

Met Ala Asn Tyr Pro Gln Gly Leu Asp Asp Lys Thr Asn Ile Lys Thr
 50                  55                  60

Val Cys Thr Tyr Trp Glu Asp Phe His Ser Cys Thr Val Thr Ala Leu
 65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
                100                 105                 110

Ser Gly Asn Gly Ala Ala Gly Ser Leu Leu Pro Ala Phe Pro Val Leu
            115                 120                 125

Leu Val Ser Leu Ser Ala Ala Leu Ala Thr Trp Leu Ser Phe
        130                 135                 140

<210> SEQ ID NO 10
<211> LENGTH: 142
<212> TYPE: PRT
<213> ORGANISM: Gorilla gorilla gorilla

<400> SEQUENCE: 10

Met Gly Leu Lys Leu Asn Gly Arg Tyr Ile Ser Leu Ile Leu Ala Val
 1               5                  10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
            35                  40                  45

Met Ala Asn Tyr Pro Gln Gly Leu Asp Asp Lys Thr Asn Ile Lys Thr
 50                  55                  60

Val Cys Thr Tyr Trp Glu Asp Phe His Ser Cys Thr Val Thr Ala Leu
 65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
                100                 105                 110

Ser Gly Asn Gly Ala Ala Gly Ser Leu Leu Pro Ala Phe Pro Val Leu
            115                 120                 125

Leu Val Ser Leu Ser Ala Ala Leu Ala Thr Trp Leu Ser Phe
        130                 135                 140

<210> SEQ ID NO 11
<211> LENGTH: 142
<212> TYPE: PRT
<213> ORGANISM: Pan troglodytes

<400> SEQUENCE: 11

Met Gly Leu Lys Leu Asn Gly Arg Tyr Ile Ser Leu Ile Leu Ala Val
 1               5                  10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
            35                  40                  45

Met Ala Asn Tyr Pro Gln Gly Leu Asp Asp Lys Thr Asn Ile Lys Thr
 50                  55                  60

Val Cys Thr Tyr Trp Glu Asp Phe His Ser Cys Thr Val Thr Ala Leu
 65                  70                  75                  80
```

```
Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
            100                 105                 110

Ser Gly Asn Gly Ala Ala Gly Ser Leu Leu Pro Ala Phe Pro Val Leu
        115                 120                 125

Leu Val Ser Leu Ser Ala Ala Leu Ala Thr Trp Leu Ser Phe
130                 135                 140

<210> SEQ ID NO 12
<211> LENGTH: 142
<212> TYPE: PRT
<213> ORGANISM: Papio anubis

<400> SEQUENCE: 12

Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
            100                 105                 110

Ser Gly Asn Gly Ala Ala Gly Ser Leu Leu Pro Ala Leu Pro Val Leu
        115                 120                 125

Leu Val Ser Leu Ser Ala Ala Leu Ala Thr Trp Leu Ser Phe
130                 135                 140

<210> SEQ ID NO 13
<211> LENGTH: 142
<212> TYPE: PRT
<213> ORGANISM: Felis catus

<400> SEQUENCE: 13

Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
            100                 105                 110

Ser Gly Asn Gly Ala Ala Gly Ser Leu Leu Pro Ala Leu Pro Val Leu
        115                 120                 125
```

```
Leu Val Ser Leu Ser Ala Ala Leu Ala Thr Trp Leu Ser Phe
        130                 135                 140
```

<210> SEQ ID NO 14
<211> LENGTH: 142
<212> TYPE: PRT
<213> ORGANISM: Ailuropoda melanoleuca

<400> SEQUENCE: 14

```
Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
    50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
            100                 105                 110

Ser Gly Asn Gly Ala Ala Gly Ser Leu Leu Pro Ala Leu Pro Val Leu
        115                 120                 125

Leu Val Ser Leu Ser Ala Ala Leu Ala Thr Trp Leu Ser Phe
    130                 135                 140
```

<210> SEQ ID NO 15
<211> LENGTH: 142
<212> TYPE: PRT
<213> ORGANISM: Macaca fascicularis

<400> SEQUENCE: 15

```
Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
    50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
            100                 105                 110

Ser Gly Asn Gly Ala Ala Gly Ser Leu Leu Pro Ala Leu Pro Val Leu
        115                 120                 125

Leu Val Ser Leu Ser Ala Ala Leu Ala Thr Trp Leu Ser Phe
    130                 135                 140
```

<210> SEQ ID NO 16
<211> LENGTH: 163
<212> TYPE: PRT
<213> ORGANISM: Callithrix jacchus

<400> SEQUENCE: 16

Met Thr Ile Asn Gly Asp Ser Leu Pro Arg Ser Ala Val Ala Asn Gly
1               5                   10                  15

Leu Thr Lys Arg Arg Met Gly Leu Lys Leu Asn Gly Arg Tyr Ile Ser
            20                  25                  30

Leu Ile Leu Ala Val Gln Ile Ala Tyr Leu Val Gln Ala Val Arg Ala
        35                  40                  45

Ala Gly Lys Cys Asp Ala Val Phe Lys Gly Phe Ser Asp Cys Leu Leu
    50                  55                  60

Lys Leu Gly Asp Ser Met Ala Asn Tyr Pro Gln Gly Leu Asp Asp Lys
65                  70                  75                  80

Thr Asn Ile Lys Thr Val Cys Thr Tyr Trp Glu Asp Phe His Ser Cys
                85                  90                  95

Thr Val Thr Ala Leu Thr Asp Cys Gln Glu Gly Ala Lys Asp Met Trp
            100                 105                 110

Asp Lys Leu Arg Lys Glu Ser Lys Asn Leu Asn Ile Gln Gly Ser Leu
        115                 120                 125

Phe Glu Leu Cys Gly Ser Gly Asn Gly Ala Ala Gly Ser Leu Leu Pro
    130                 135                 140

Ala Leu Pro Val Leu Leu Val Ser Leu Ser Ala Ala Leu Ala Thr Trp
145                 150                 155                 160

Leu Ser Phe

<210> SEQ ID NO 17
<211> LENGTH: 142
<212> TYPE: PRT
<213> ORGANISM: Macaca mulatta

<400> SEQUENCE: 17

Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
    50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
            100                 105                 110

Ser Gly Asn Gly Ala Ala Gly Ser Leu Leu Pro Ala Leu Pro Val Leu
        115                 120                 125

Leu Val Ser Leu Ser Ala Ala Leu Ala Thr Trp Leu Ser Phe
    130                 135                 140

<210> SEQ ID NO 18
<211> LENGTH: 142
<212> TYPE: PRT
<213> ORGANISM: Canis lupus familiaris

<400> SEQUENCE: 18

Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
    50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
            100                 105                 110

Ser Gly Asn Gly Ala Ala Gly Ser Leu Leu Pro Ala Leu Pro Leu Leu
            115                 120                 125

Leu Val Ser Leu Ser Ala Ala Leu Ala Thr Trp Leu Ser Phe
    130                 135                 140

<210> SEQ ID NO 19
<211> LENGTH: 142
<212> TYPE: PRT
<213> ORGANISM: Sus scrofa

<400> SEQUENCE: 19

Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
    50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
            100                 105                 110

Ser Gly Asn Gly Ala Ala Gly Ser Leu Leu Pro Ala Leu Pro Val Leu
            115                 120                 125

Leu Val Ala Leu Ser Ala Ala Leu Ala Thr Trp Leu Ser Phe
    130                 135                 140

<210> SEQ ID NO 20
<211> LENGTH: 142
<212> TYPE: PRT
<213> ORGANISM: Pteropus Alecto

<400> SEQUENCE: 20

Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
    50                  55                  60

```
Val Cys Thr Tyr Trp Glu Asp Phe His Ser Cys Thr Val Thr Ala Leu
 65                  70                  75                  80

Thr Asp Cys Gln Glu Gly Ala Lys Asp Met Trp Asp Lys Leu Arg Lys
                 85                  90                  95

Glu Ser Lys Asn Leu Asn Ile Gln Gly Ser Leu Phe Glu Leu Cys Gly
                100                 105                 110

Ser Gly Asn Gly Ala Ala Gly Ser Leu Leu Pro Ala Leu Pro Val Leu
            115                 120                 125

Leu Ala Ser Leu Ser Ala Ala Leu Ala Thr Trp Leu Ser Phe
    130                 135                 140
```

<210> SEQ ID NO 21
<211> LENGTH: 142
<212> TYPE: PRT
<213> ORGANISM: Dipodomys ordii

<400> SEQUENCE: 21

```
Met Gly Leu Lys Leu Asn Gly Arg Tyr Ile Ser Leu Ile Leu Ala Val
  1               5                  10                  15

Gln Ile Ala Tyr Leu Val Gln Ala Val Arg Ala Ala Gly Lys Cys Asp
                 20                  25                  30

Ala Val Phe Lys Gly Phe Ser Asp Cys Leu Leu Lys Leu Gly Asp Ser
                 35                  40                  45

Met Ala Asn Tyr Pro Gln Gly Leu Asp Asp Lys Thr Asn Ile Lys Thr
     50                  55                  60

Val Cys Thr Tyr Trp Glu Asp Phe His Ser Cys Thr Val Thr Ala Leu
 65                  70                  75                  80

Thr Asp Cys Gln Glu Gly Ala Lys Asp Met Trp Asp Lys Leu Arg Lys
                 85                  90                  95

Glu Ser Lys Asn Leu Asn Ile Gln Gly Ser Leu Phe Glu Leu Cys Ser
                100                 105                 110

Ser Gly Asn Gly Ala Ala Gly Pro Leu Leu Pro Ala Phe Pro Val Leu
            115                 120                 125

Leu Val Ser Leu Ser Ala Ala Leu Ala Thr Trp Leu Ser Phe
    130                 135                 140
```

<210> SEQ ID NO 22
<211> LENGTH: 142
<212> TYPE: PRT
<213> ORGANISM: Equus caballus

<400> SEQUENCE: 22

```
Met Gly Leu Lys Leu Asn Gly Arg Tyr Ile Ser Leu Ile Leu Ala Val
  1               5                  10                  15

Gln Ile Ala Tyr Leu Val Gln Ala Val Arg Ala Ala Gly Lys Cys Asp
                 20                  25                  30

Ala Val Phe Lys Gly Phe Ser Asp Cys Leu Leu Lys Leu Gly Asp Ser
                 35                  40                  45

Met Ala Asn Tyr Pro Gln Gly Leu Asp Asp Lys Thr Asn Ile Lys Thr
     50                  55                  60

Val Cys Thr Tyr Trp Glu Asp Phe His Ser Cys Thr Val Thr Ala Leu
 65                  70                  75                  80

Thr Asp Cys Gln Glu Gly Ala Lys Asp Met Trp Asp Lys Leu Arg Lys
                 85                  90                  95

Glu Ser Lys Asn Leu Asn Ile Gln Gly Ser Leu Phe Glu Leu Cys Gly
                100                 105                 110
```

```
Ser Gly Asn Gly Ala Ala Gly Ser Leu Leu Pro Ala Leu Pro Val Leu
        115                 120                 125

Leu Val Ser Leu Ser Ala Ala Leu Ala Ala Trp Leu Ser Phe
130                 135                 140
```

<210> SEQ ID NO 23
<211> LENGTH: 142
<212> TYPE: PRT
<213> ORGANISM: Neovison vison

<400> SEQUENCE: 23

```
Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
    50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
            100                 105                 110

Ser Gly Asn Gly Ala Ala Gly Ser Leu Leu Pro Thr Leu Pro Val Leu
        115                 120                 125

Leu Met Ser Leu Ser Ala Ala Leu Ala Thr Trp Leu Ser Phe
130                 135                 140
```

<210> SEQ ID NO 24
<211> LENGTH: 142
<212> TYPE: PRT
<213> ORGANISM: Carlito syrichta

<400> SEQUENCE: 24

```
Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
    50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Leu Trp Asp Lys Leu Arg Lys
                85                  90                  95

Glu Ser Lys Asn Leu Asn Phe Gln Gly Ser Leu Phe Glu Leu Cys Gly
            100                 105                 110

Ser Gly Asn Gly Ala Ala Gly Ser Leu Leu Pro Ala Leu Pro Val Leu
        115                 120                 125

Leu Val Ser Leu Ser Ala Ala Leu Ala Thr Trp Leu Ser Phe
130                 135                 140
```

<210> SEQ ID NO 25

<211> LENGTH: 142
<212> TYPE: PRT
<213> ORGANISM: Mesocricetus auratus

<400> SEQUENCE: 25

Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
    50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
            100                 105                 110

Ser Gly Asn Gly Ala Ala Gly Ser Leu Leu Pro Ala Leu Ser Val Leu
        115                 120                 125

Leu Val Ser Leu Ser Ala Ala Leu Ala Thr Trp Leu Ser Phe
    130                 135                 140

<210> SEQ ID NO 26
<211> LENGTH: 142
<212> TYPE: PRT
<213> ORGANISM: Otolemur garnettii

<400> SEQUENCE: 26

Met Gly Leu Lys Leu Asn Gly Arg Tyr Ile Ser Leu Ile Leu Ala Val
1               5                   10                  15

Gln Ile Ala Tyr Leu Val Gln Ala Val Arg Ala Ala Gly Lys Cys Asp
            20                  25                  30

Ala Val Phe Lys Gly Phe Ser Asp Cys Leu Leu Lys Leu Gly Asp Ser
        35                  40                  45

Met Ala Asn Tyr Pro Gln Gly Leu Asp Asp Lys Thr Asn Ile Lys Thr
    50                  55                  60

Val Cys Thr Tyr Trp Glu Asp Phe His Ser Cys Thr Val Thr Ala Leu
65                  70                  75                  80

Thr Asp Cys Gln Glu Gly Ala Lys Asp Met Trp Asp Lys Leu Arg Lys
                85                  90                  95

Glu Ser Lys Asn Leu Asn Ile Gln Gly Ser Leu Phe Glu Leu Cys Gly
            100                 105                 110

Gly Gly Asn Gly Ala Ala Gly Ser Leu Phe Pro Ala Leu Pro Val Leu
        115                 120                 125

Leu Val Ser Leu Ser Ala Ala Leu Ala Thr Trp Leu Ser Phe
    130                 135                 140

<210> SEQ ID NO 27
<211> LENGTH: 142
<212> TYPE: PRT
<213> ORGANISM: Rattus norvegicus

<400> SEQUENCE: 27

Met Gly Leu Lys Leu Asn Gly Arg Tyr Ile Ser Leu Ile Leu Ala Val
1               5                   10                  15

```
Gln Ile Ala Tyr Leu Val Gln Ala Val Arg Ala Ala Gly Lys Cys Asp
             20                  25                  30

Ala Val Phe Lys Gly Phe Ser Asp Cys Leu Leu Lys Leu Gly Asp Ser
         35                  40                  45

Met Ala Asn Tyr Pro Gln Gly Leu Asp Asp Lys Thr Asn Ile Lys Thr
 50                  55                  60

Val Cys Thr Tyr Trp Glu Asp Phe His Ser Cys Thr Val Thr Ala Leu
 65                  70                  75                  80

Thr Asp Cys Gln Glu Gly Ala Lys Asp Met Trp Asp Lys Leu Arg Lys
                 85                  90                  95

Glu Ser Lys Asn Leu Asn Ile Gln Gly Ser Leu Phe Glu Leu Cys Gly
            100                 105                 110

Ser Gly Asn Gly Ala Ala Gly Ser Leu Leu Pro Ala Leu Ser Val Leu
        115                 120                 125

Leu Val Ser Leu Ser Ala Ala Leu Ala Thr Trp Leu Ser Phe
    130                 135                 140
```

<210> SEQ ID NO 28
<211> LENGTH: 142
<212> TYPE: PRT
<213> ORGANISM: Bos taurus

<400> SEQUENCE: 28

```
Met Gly Leu Lys Leu Asn Gly Arg Tyr Ile Ser Leu Ile Leu Ala Val
 1               5                  10                  15

Gln Ile Ala Tyr Leu Val Gln Ala Val Arg Ala Ala Gly Lys Cys Asp
             20                  25                  30

Ala Val Phe Lys Gly Phe Ser Asp Cys Leu Leu Lys Leu Gly Asp Ser
         35                  40                  45

Met Ala Asn Tyr Pro Gln Gly Leu Asp Asp Lys Thr Asn Ile Lys Thr
 50                  55                  60

Val Cys Thr Tyr Trp Glu Asp Phe His Ser Cys Thr Val Thr Ala Leu
 65                  70                  75                  80

Thr Asp Cys Gln Glu Gly Ala Lys Asp Met Trp Asp Lys Leu Arg Lys
                 85                  90                  95

Glu Ser Lys Asn Leu Asn Ile Gln Gly Ser Leu Phe Glu Leu Cys Gly
            100                 105                 110

Gly Gly Asn Gly Ala Ala Gly Pro Leu Leu Pro Ala Leu Pro Val Leu
        115                 120                 125

Leu Val Ser Leu Ser Ala Ala Leu Ala Thr Trp Leu Ser Phe
    130                 135                 140
```

<210> SEQ ID NO 29
<211> LENGTH: 142
<212> TYPE: PRT
<213> ORGANISM: Neotoma lepida

<400> SEQUENCE: 29

```
Met Gly Leu Lys Leu Asn Gly Arg Tyr Ile Ser Leu Ile Leu Ala Val
 1               5                  10                  15

Gln Ile Ala Tyr Leu Val Gln Ala Val Arg Ala Ala Gly Lys Cys Asp
             20                  25                  30

Ala Val Phe Lys Gly Phe Ser Asp Cys Leu Leu Lys Leu Gly Asp Ser
         35                  40                  45

Met Ala Asn Tyr Pro Gln Gly Leu Asp Asp Lys Thr Asn Ile Lys Thr
 50                  55                  60
```

-continued

```
Val Cys Thr Tyr Trp Glu Asp Phe His Ser Cys Thr Val Thr Ala Leu
 65                  70                  75                  80

Thr Asp Cys Gln Glu Gly Ala Lys Asp Met Trp Asp Lys Leu Arg Lys
                 85                  90                  95

Glu Ser Lys Asn Leu Asn Ile Gln Gly Ser Leu Phe Glu Leu Cys Gly
            100                 105                 110

Thr Gly Asn Gly Ala Ala Gly Ser Leu Leu Pro Ala Leu Ser Val Leu
            115                 120                 125

Leu Val Ser Leu Ser Ala Ala Leu Ala Thr Trp Leu Ser Phe
        130                 135                 140

<210> SEQ ID NO 30
<211> LENGTH: 142
<212> TYPE: PRT
<213> ORGANISM: Ovis aries

<400> SEQUENCE: 30

Met Gly Leu Lys Leu Asn Gly Arg Tyr Ile Ser Leu Ile Leu Ala Val
 1               5                  10                  15

Gln Ile Ala Tyr Leu Val Gln Ala Val Arg Ala Ala Gly Lys Cys Asp
                 20                  25                  30

Ala Val Phe Lys Gly Phe Ser Asp Cys Leu Leu Lys Leu Gly Asp Ser
             35                  40                  45

Met Ala Asn Tyr Pro Gln Gly Leu Asp Asp Lys Thr Asn Ile Lys Thr
     50                  55                  60

Val Cys Thr Tyr Trp Glu Asp Phe His Ser Cys Thr Val Thr Ala Leu
 65                  70                  75                  80

Thr Asp Cys Gln Glu Gly Ala Lys Asp Met Trp Asp Lys Leu Arg Lys
                 85                  90                  95

Glu Ser Lys Asn Leu Asn Ile Gln Gly Ser Leu Phe Glu Leu Cys Gly
            100                 105                 110

Gly Gly Asn Gly Ala Ala Gly Pro Leu Leu Pro Ala Leu Pro Val Leu
            115                 120                 125

Leu Val Ser Leu Ser Ala Ala Leu Ala Ala Trp Leu Ser Phe
        130                 135                 140
```

| | | *: : :***.:***: | |

IMMUNOREGULATORY MOLECULES AND USES THEREFOR

RELATED APPLICATIONS

This application is a § 371 National Entry Application of PCT/AU2018/050944, filed Aug. 31, 2018, which claims priority to Australian Provisional Application No. 2017903538 entitled "Immunoregulatory molecules and Uses therefor" filed 1 Sep. 2017.

SEQUENCE LISTING

The text of the computer readable sequence listing filed herewith, titled "38305-251_SEQUENCE_LISTING_ST25", created Feb. 8, 2021, having a file size of 36,163 bytes, is hereby incorporated by reference in its entirety.

FIELD OF THE INVENTION

This invention relates generally to treating unwanted or deleterious immune responses. More particularly, the present invention relates to neuritin agents for use in inhibiting plasma cell (PC) differentiation, reducing the number of autoreactive B cells, treating, or inhibiting the development or progression of, autoreactive B cell disorders including B cell-mediated autoimmune diseases and IgE-mediated disorders and of monoclonal gammopathies and PC dyscrasias.

BACKGROUND OF THE INVENTION

The incidence and prevalence of autoimmune diseases across the world are increasing (Lerner et al., 2015. *International Journal of Celiac Disease* 3(4):151-155). These diseases are characterized by a break in tolerance where a patient's immune system attacks its own organs and tissues. Many of these diseases, like rheumatoid arthritis (RA), systemic lupus erythematous (SLE) and multiple sclerosis (MS) are at least in part the result of dysregulated antibody production. Allergies can also be caused by dysregulated selection of antibody producing cells, where potentially pathogenic isotypes such as IgE are excessively produced.

Production of autoantibodies can lead to several pathologic sequelae. For example, autoantibodies can greatly amplify inflammatory responses and thereby play an important role in promoting tissue damage. Immune complexes containing IgM or IgG autoantibodies can initiate complement-mediated inflammation and can activate inflammatory cells by binding to Fc receptors (Takai T., 2002. *Nat Rev Immunol* 2:580-592). The formation of large immune complexes can also block kidney tubules and blood vessels, leading to glomerulonephritis or thrombosis (Lipsky P E., 2001. *Nat Immunol* 2:764-766). Additionally, autoantibodies that bind to host cells may promote antibody-dependent cellular cytotoxicity carried out by natural killer (NK) cells or macrophages (Herberman et al., 1986. *Annu Rev Immunol* 4:651-680).

Aberrant regulation of PCs can lead to PC dyscrasias. PC dyscrasias (also termed PC disorders and PC proliferative diseases) are a spectrum of progressively more severe monoclonal gammopathies in which a clone or multiple clones of pre-malignant or malignant PCs (sometimes in association with lymphoplasmacytoid cells or B lymphocytes) overproduce a myeloma protein, i.e., an abnormal monoclonal antibody or portion thereof. A common and clinically silent disorder termed monoclonal gammopathy of undetermined significance (MGUS) may progress to the malignant form which includes multiple myeloma, Waldenström's macroglobulinemia, or other B cell-associated neoplasms that derive stepwise from an MGUS precursor.

Germinal centers (GCs) are the hallmark of the T-dependent antigen immune response. They originate within secondary lymphoid tissues upon infection or immunization. Within GCs, B cells undergo a reiterative process of proliferation, mutation and selection by T follicular helper ($T_{FH}$) cells, allowing the fittest B cells to survive and differentiate into memory cells and PCs. During this process, B cells can acquire mutations that could potentially make them self-reactive. A stringent process of selection is thought to occur to prevent the emergence of autoreactive and IgE-expressing B cells.

Several years ago, the existence of T follicular regulatory ($T_{FR}$) cells was described by Linterman et al., (2011. *Nat Med* 17(8):975-982). These cells arise as the repressive GC T cell subset, important for curtailing the GC reaction. The balance between $T_{FH}$ and $T_{FR}$ cells controls antibody selection in GCs, which is essential to achieve optimal affinity maturation in the course of immunization.

SUMMARY OF THE INVENTION

In an effort to identify key molecules that mediate suppression of autoantibody formation, the present inventors identified 1283 genes that are differentially expressed between $T_{FR}$ and $T_{FH}$ cells. Of these, Nrn-1, the gene encoding the neurotrophic factor, neuritin, was found to be the most highly upregulated gene in $T_{FR}$ cells, as compared to $T_{FH}$ cells. Indeed, the present inventors found that $T_{FR}$ cells are the major source of neuritin in the GC and that neuritin binds preferentially to GC B cells, suppresses IgE production and terminal differentiation of PCs, and reduces the incidence of autoantibodies in the absence of $T_{FR}$ cells. These findings have been reduced to practice in methods and compositions for inhibiting PC differentiation, for reducing the number of autoreactive B cells, and for treating, or inhibiting the development or progression of, autoreactive B cell disorders (e.g., B cell-mediated autoimmune diseases), and IgE-mediated disorders, as described hereafter.

Accordingly, the present invention in one aspect provides methods for inhibiting PC differentiation in a subject. These methods generally comprise, consist or consist essentially of contacting a B cell (e.g., a GC B cell) of the subject with a neuritin polypeptide, to thereby inhibit PC differentiation in the subject.

In a related aspect, the present invention provides methods for inhibiting PC differentiation in a subject. These methods generally comprise, consist or consist essentially of administering to the subject an effective amount of a neuritin agent selected from a neuritin polypeptide, a coding sequence for a neuritin polypeptide and a cell (e.g., a T cell such as a $T_{FR}$ cell) from which a coding sequence for a neuritin polypeptide is expressible, to thereby inhibit PC differentiation in the subject.

Suitably, the PC differentiation is associated with production of autoreactive B cells. In representative examples of this type, the PC differentiation is associated with the presence or risk of development of an autoreactive B cell disorder (e.g., a B cell-mediated autoimmune disease). The autoreactive B cell disorder (e.g., a B cell-mediated autoimmune disease) is suitably a systemic or organ-specific autoimmune disease.

In some embodiments, these methods further comprise identifying that the subject has or is at risk of developing an autoreactive B cell disorder (e.g., a B cell-mediated autoimmune disease). The autoreactive B cell disorder (e.g., a B cell-mediated autoimmune disease) is suitably a systemic or organ-specific autoimmune disease.

In some of the same and other embodiments, these methods further comprise identifying that the subject has or is at risk of developing an IgE-mediated disorder (e.g., an allergy or an IgE-mediated autoimmune disease). The IgE-mediated autoimmune disease is suitably a systemic or organ-specific autoimmune disease.

Another aspect of the present invention provides methods for reducing the number of autoreactive B cells in a subject. These methods generally comprise, consist or consist essentially of contacting a B cell (e.g., a recently activated or GC B cell) of the subject with a neuritin polypeptide, to thereby reduce the number of autoreactive B cells in the subject.

In a related aspect, the present invention provides methods for reducing the number of autoreactive B cells in a subject. These methods generally comprise, consist or consist essentially of administering to the subject an effective amount of a neuritin agent selected from a neuritin polypeptide, a coding sequence for a neuritin polypeptide and a cell (e.g., a T cell such as a $T_{FR}$ cell) from which a coding sequence for a neuritin polypeptide is expressible, to thereby reduce the number of autoreactive B cells in the subject.

In some embodiments, these methods further comprise identifying that the subject has or is at risk of developing an autoreactive B cell disorder (e.g., a B cell-mediated autoimmune disease). The autoreactive B cell disorder (e.g., a B cell-mediated autoimmune disease) is suitably a systemic or organ-specific autoimmune disease.

In some of the same and other embodiments, these methods further comprise identifying that the subject has or is at risk of developing an IgE-mediated disorder (e.g., an allergy or an IgE-mediated autoimmune disease). The IgE-mediated autoimmune disease is suitably a systemic or an organ-specific autoimmune disease.

Yet another aspect of the present invention provides methods for treating, or inhibiting the development or progression of, an autoreactive B cell disorder. These methods generally comprise, consist or consist essentially of administering to the subject an effective amount of a neuritin agent selected from a neuritin polypeptide, a coding sequence for a neuritin polypeptide and a cell (e.g., a T cell such as a $T_{FR}$ cell) from which a coding sequence for a neuritin polypeptide is expressible, to thereby treat, or inhibit the development or progression of, the autoreactive B cell disorder. In specific embodiments, the autoreactive B cell disorder is a B cell-mediated autoimmune disease. The autoreactive B cell disorder (e.g., a B cell-mediated autoimmune disease) is suitably a systemic or an organ-specific autoimmune disease.

In still another aspect, the present invention provides methods for treating, or inhibiting the development or progression of, a B cell-mediated autoimmune disease. These methods generally comprise, consist or consist essentially of administering to the subject an effective amount of a neuritin agent selected from a neuritin polypeptide, a coding sequence for a neuritin polypeptide and a cell (e.g., a T cell such as a $T_{FR}$ cell) from which a coding sequence for a neuritin polypeptide is expressible, to thereby treat, or inhibit the development or progression of, the B cell-mediated autoimmune disease, which is suitably a systemic or an organ-specific autoimmune disease.

Yet another aspect of the present invention provides methods for treating, or inhibiting the development or progression of, an IgE-mediated disorder. These methods generally comprise, consist or consist essentially of administering to the subject an effective amount of a neuritin agent selected from a neuritin polypeptide, a coding sequence for a neuritin polypeptide and a cell (e.g., a T cell such as a $T_{FR}$ cell) from which a coding sequence for a neuritin polypeptide is expressible, to thereby treat, or inhibit the development or progression of, the IgE-mediated disorder (e.g., an allergy or an IgE-mediated autoimmune disease), which is suitably a systemic or an organ-specific autoimmune disease.

Still another aspect of the present invention provides methods for treating, or inhibiting the development or progression of, an PC dyscrasia. These methods generally comprise, consist or consist essentially of administering to the subject an effective amount of a neuritin agent selected from a neuritin polypeptide, a coding sequence for a neuritin polypeptide and a cell (e.g., a T cell such as a $T_{FR}$ cell) from which a coding sequence for a neuritin polypeptide is expressible, to thereby treat, or inhibit the development or progression of, the PC dyscrasia (e.g., a MGUS which is suitably associated with a malignancy such as but not limited to multiple myeloma, Waldenström's macroglobulinemia, or other B cell-associated neoplasm).

A further aspect of the present invention provides a use of a neuritin agent selected from a neuritin polypeptide, a coding sequence for a neuritin polypeptide and a cell (e.g., a T cell such as a $T_{FR}$ cell) from which a coding sequence for a neuritin polypeptide is expressible, for inhibiting PC differentiation, for reducing the number of autoreactive B cells, for treating, or inhibiting the development or progression of, an autoreactive B cell disorder, for treating, or inhibiting the development or progression of, a B cell-mediated autoimmune disease, and/or for treating, or inhibiting the development or progression of, an IgE-mediated disorder. In some embodiments, the neuritin agent is prepared or manufactured as a medicament for that use.

BRIEF DESCRIPTION OF THE DRAWINGS

FIG. 13 is a diagrammatic representation showing the results of a sequence alignment of the following full-length precursor neuritin amino acid sequences: northern white-cheeked gibbon (UniProt Accession No. G1RL84) (SEQ ID NO: 7), green monkey (UniProt Accession No. A0A0D9R4S6) (SEQ ID NO: 8), Sumatran orangutan (UniProt Accession No. H2PHU4) (SEQ ID NO: 9), western lowland gorilla (UniProt Accession No. G3QR76) (SEQ ID NO: 10), chimpanzee (UniProt Accession No. H2QS91) (SEQ ID NO: 11), human (UniProt Accession No. Q9NPD7) (SEQ ID NO: 2), olive baboon (UniProt Accession No. A0A096NKQ3_A0A2I3LJGO) (SEQ ID NO: 12), cat (UniProt Accession No. M3X8K3) (SEQ ID NO: 13), giant panda (UniProt Accession No. G1MGE3) (SEQ ID NO: 14), crab-eating macaque (UniProt Accession No. G7P4C7) (SEQ ID NO: 15), white-tufted-ear marmoset (UniProt Accession No. F7HEM3) (SEQ ID NO: 16), rhesus macaque (UniProt Accession No. F6SIH8) (SEQ ID NO: 17), dog (UniProt Accession No. E2RK66) (SEQ ID NO: 18), pig (UniProt Accession No. F1RW81) (SEQ ID NO: 19), black flying fox (UniProt Accession No. L5KUZ4) (SEQ ID NO: 20), Ord's kangaroo rat (UniProt Accession No. A0A1S3F647) (SEQ ID NO: 21), horse (UniProt Accession No. F7DF40) (SEQ ID NO: 22), American mink (UniProt Accession No. U6CV18) (SEQ ID NO: 23), Philippine tarsier (UniProt Accession No. A0A1U7UID3) (SEQ ID NO: 24), golden hamster (UniProt Accession No. A0A1U7Q3R0) (SEQ ID NO: 25), small-eared galago (UniProt Accession No. HOXRS4) (SEQ ID NO: 26), rat (UniProt Accession No. O08957) (SEQ ID NO: 27), bovine (UniProt Accession No. Q2KIC6) (SEQ ID NO: 28), desert woodrat (UniProt Accession No. A0A1A6HJB8) (SEQ ID NO: 29) and sheep (UniProt Accession No. W5QBC3) (SEQ ID NO: 30).

Figure 1:
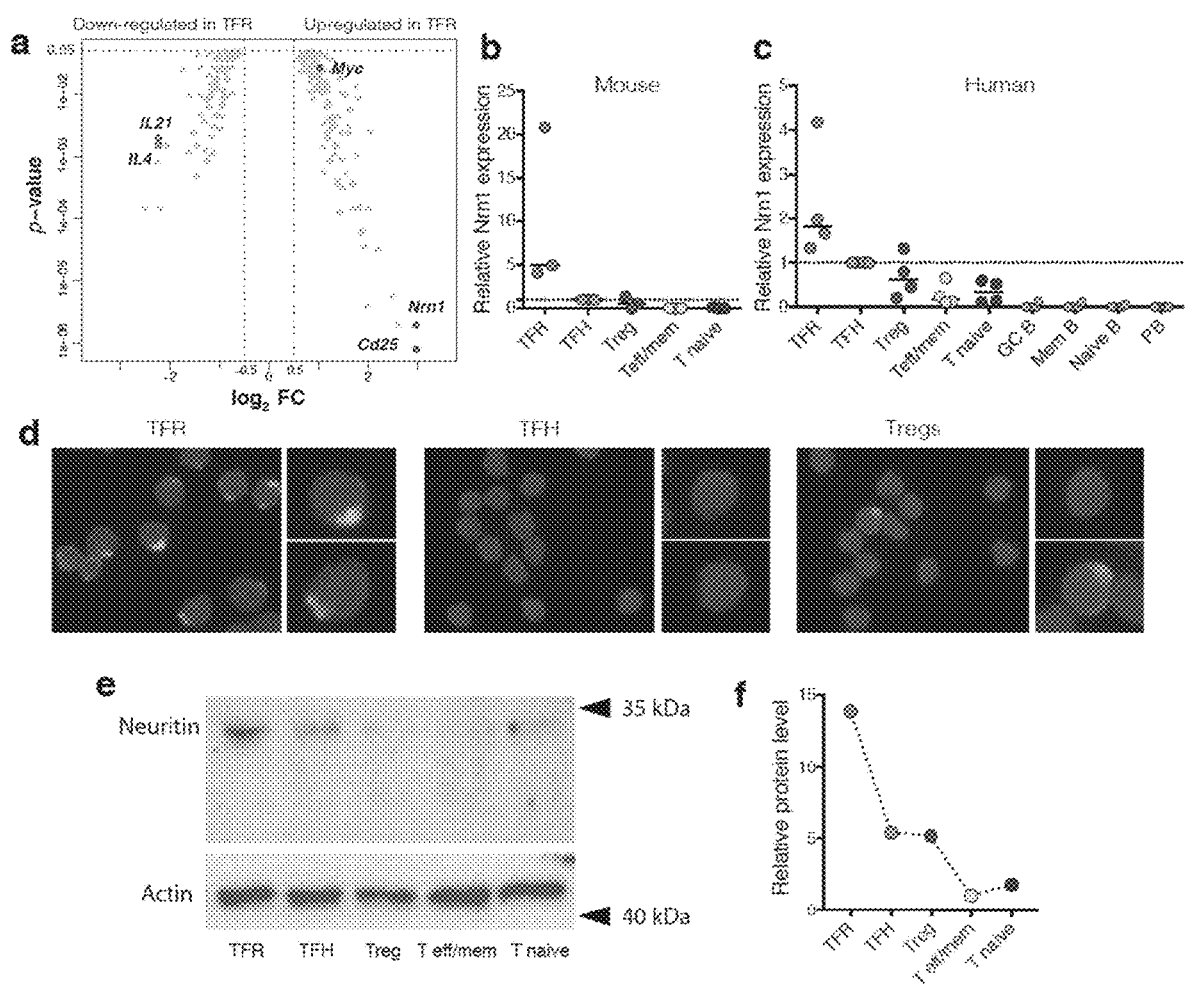
FIG. 1 is a graphical and photographic representation showing that $T_{FR}$ cells express neuritin mRNA and protein. A) Volcano plot showing differentially expressed genes in sorted mouse $T_{FR}$ cells compared to $T_{FH}$ cells by microarray expression analysis (* p≤0.05). B) Relative neuritin expression in sorted mouse and (C) human T and B cell subsets by qPCR. D) Cytospin of sorted human $T_{FR}$, $T_{FH}$ and $T_{REG}$ cells (DAPI in blue; neuritin in red). E) Western blot analysis and (F) quantification of neuritin protein expression in sorted human $T_{FR}$, $T_{FH}$, $T_{REG}$, T effector/memory and T naïve cells.

Some figures and text contain color representations or entities. Color illustrations are available from the Applicant upon request or from an appropriate Patent Office. A fee may be imposed if obtained from a Patent Office.

TABLE A

BRIEF DESCRIPTION OF THE SEQUENCES

| SEQUENCE ID NUMBER | SEQUENCE | LENGTH |
|---|---|---|
| SEQ ID NO: 1 | Nrn-1 coding sequence | 429 nts |
| SEQ ID NO: 2 | Nrn-1 precursor polypeptide | 142 aa |
| SEQ ID NO: 3 | Coding sequence for Nrn-1 pro-peptide | 348 nts |
| SEQ ID NO: 4 | Nrn-1 pro-peptide | 115 aa |
| SEQ ID NO: 5 | Coding sequence for mature Nrn-1 polypeptide | 267 nts |
| SEQ ID NO: 6 | Mature Nrn-1 polypeptide | 89 aa |

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

As used herein, the term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about 1 min to within about 1 d before or after another. Any contemporaneous time is useful. However, it will often be the case that when not administered simultaneously, the agents will be administered within about 1 min to within about 8 h and preferably within less than about 1 h to about 4 h. When administered contemporaneously, the agents are suitably administered at the same site on the subject. The term "same site" includes the exact location, but can be within about 0.5 cm to about 15 cm, preferably from within about 0.5 cm to about 5 cm. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

The term "agent" includes a compound that induces a desired pharmacological and/or physiological effect. The term also encompass pharmaceutically acceptable and pharmacologically active ingredients of those compounds specifically mentioned herein including but not limited to salts, esters, amides, prodrugs, active metabolites, analogs and the like. When the above term is used, then it is to be understood that this includes the active agent per se as well as pharmaceutically acceptable, pharmacologically active salts, esters, amides, prodrugs, metabolites, analogs, etc. The term "agent" is not to be construed narrowly but extends to small molecules, proteinaceous molecules such as peptides, polypeptides and proteins as well as compositions comprising them and genetic molecules such as RNA, DNA and mimetics and chemical analogs thereof as well as cellular agents. The term "agent" includes a cell that is capable of producing and secreting a polypeptide referred to herein as well as a polynucleotide comprising a nucleotide sequence that encodes that polypeptide. Thus, the term "agent" extends to nucleic acid constructs including vectors such as viral or non-viral vectors, expression vectors and plasmids for expression in and secretion in a range of cells.

As used herein, "and/or" refers to and encompasses any and all possible combinations of one or more of the associated listed items, as well as the lack of combinations when interpreted in the alternative (or).

An "autoimmune disease" herein is a disease or disorder arising from and directed against an individual's own tissues or organs or a co-segregation or manifestation thereof or resulting condition therefrom. In many of these autoimmune and inflammatory disorders, a number of clinical and laboratory markers may exist, including, but not limited to, hypergammaglobulinemia, high levels of autoantibodies, antigen-antibody complex deposits in tissues, benefit from corticosteroid or immunosuppressive treatments, and lymphoid cell aggregates in affected tissues.

The term "autoreactive B cell" and "autoreactive B cell disorder" as used herein is understood in the following way. Autoreactive B cells are part of the naïve or post-antigenic (i.e., GC B cells, memory B cells, plasmablasts or PCs) B cell repertoire, and central in the pathogenesis of autoimmune diseases not only by producing autoantibodies but also by secreting cytokines and by presenting autoantigens. An autoreactive B cell disorder is meant to refer to a disease condition caused by activation and/or differentiation of self-reactive B cells, that may be ameliorated by the administration of a pharmaceutical composition comprising a neuritin agent of the invention. In diseases associated with an autoreactive B cell disorder, like B cell-mediated autoimmune diseases, there is typically an aberrant negative selection, or a lowered threshold for positive selection and activation of autoreactive B cells.

As used herein, "cell therapy" is a method of treatment involving the administration of live cells The term "contacting" or "exposing" as used herein refers to bringing a disclosed compound and a cell, a target receptor, or other biological entity together in such a manner that the compound can affect the activity of the target (e.g., enzyme, cell, etc.), either directly; i.e., by interacting with the target itself, or indirectly; i.e., by interacting with another molecule, co-factor, factor, or protein on which the activity of the target is dependent. Contacting can take place in vitro, ex vivo, or in vivo. In specific embodiments, the term "contacting" includes allowing a neuritin polypeptide and a B cell (e.g., a GC B cell) or surface molecule of a B cell to interact. Contacting may include allowing a neuritin polypeptide to interact with a protein or enzyme that is involved in a signaling pathway.

By "coding sequence" is meant any nucleic acid sequence that contributes to the code for the polypeptide product of a gene or for the final mRNA product of a gene (e.g. the mRNA product of a gene following splicing). By contrast, the term "non-coding sequence" refers to any nucleic acid sequence that does not contribute to the code for the polypeptide product of a gene or for the final mRNA product of a gene.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

A "conservative amino acid substitution" is one in which the amino acid residue is replaced with an amino acid residue having a similar side chain. Families of amino acid residues having similar side chains have been defined in the art, which can be generally sub-classified as follows:

TABLE 1

AMINO ACID SUB-CLASSIFICATION

| Sub-classes | Amino acids |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional polypeptide can readily be determined by assaying its activity. Conservative substitutions are shown in Table 2 under the heading of exemplary and preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE 2

EXEMPLARY AND PREFERRED AMINO ACID SUBSTITUTIONS

| Original Residue | Exemplary Substitutions | Preferred Substitutions |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

The term "construct" refers to a recombinant genetic molecule including one or more isolated nucleic acid sequences from different sources. Thus, constructs are chimeric molecules in which two or more nucleic acid sequences of different origin are assembled into a single nucleic acid molecule and include any construct that contains (1) nucleic acid sequences, including regulatory and coding sequences that are not found together in nature (i.e., at least one of the nucleotide sequences is heterologous with respect to at least one of its other nucleotide sequences), or (2) sequences encoding parts of functional RNA molecules or proteins not naturally adjoined, or (3) parts of promoters that are not naturally adjoined. Representative constructs include any recombinant nucleic acid molecule such as a plasmid, cosmid, virus, autonomously replicating polynucleotide molecule, phage, or linear or circular single stranded or double stranded DNA or RNA nucleic acid molecule, derived from any source, capable of genomic integration or autonomous replication, comprising a nucleic acid molecule where one or more nucleic acid molecules have been operably linked. Constructs of the present invention will generally include the necessary elements to direct expression of a nucleic acid sequence of interest that is also contained in the construct, such as, for example, a target nucleic acid sequence or a modulator nucleic acid sequence. Such elements may include control elements such as a promoter that is operably linked to (so as to direct transcription of) the nucleic acid sequence of interest, and often includes a polyadenylation sequence as well. Within certain embodiments of the invention, the construct may be contained within a vector. In addition to the components of the construct, the vector may include, for example, one or more selectable markers, one or more origins of replication, such as prokaryotic and eukaryotic origins, at least one multiple cloning site, and/or elements to facilitate stable integration of the construct into the genome of a host cell. Two or more constructs can be contained within a single nucleic acid molecule, such as a single vector, or can be containing within two or more separate nucleic acid molecules, such as two or more separate vectors. An "expression construct" generally includes at least a control sequence operably linked to a nucleotide sequence of interest. In this manner, for example, promoters in operable connection with the nucleotide sequences to be expressed are provided in expression constructs for expression in an organism or part thereof including a host cell. For the practice of the present invention, conventional compositions and methods for preparing and using constructs and host cells are well known to one skilled in the art, see for example, Molecular Cloning: A Laboratory Manual, 3rd edition Volumes 1, 2, and 3. J. F. Sambrook, D. W. Russell, and N. Irwin, Cold Spring Harbor Laboratory Press, 2000.

By "corresponds to" or "corresponding to" is meant an amino acid sequence that displays substantial sequence similarity or identity to a reference amino acid sequence. In general the amino acid sequence will display at least about 80, 81, 82, 83, 84, 85, 86, 87, 88, 89, 90, 91, 92, 93, 94, 95, 96, 97, 98 or 99% sequence similarity or identity to at least a portion, and suitably over the entire length, of the reference amino acid sequence.

The term "cytokine" is a generic term for proteins released by one cell population that act on another cell as intercellular mediators. Examples of such cytokines are lymphokines, monokines; interleukins (ILs) such as IL-1, IL-1α, IL-2, IL-3, IL-4, IL-5, IL-6, IL-7, IL-8, IL-9, IL-11, IL-12, IL-13, IL-15, including PROLEUKIN® rIL-2; a tumor-necrosis factor such as TNF-α or TNF-β; and other polypeptide factors including LIF and kit ligand (KL). As used herein, the term cytokine includes proteins from natural sources or from recombinant cell culture and biologically active equivalents of the native-sequence cytokines, including synthetically produced small-molecule entities and pharmaceutically acceptable derivatives and salts thereof.

The terms "disorder" and "disease" are used interchangeably herein to refer to an abnormal condition that impairs bodily functions, associated with specific symptoms and signs.

As used herein, the terms "encode", "encoding" and the like refer to the capacity of a nucleic acid to provide for another nucleic acid or a polypeptide. For example, a nucleic acid sequence is said to "encode" a polypeptide if it can be transcribed and/or translated to produce the polypeptide or if it can be processed into a form that can be transcribed and/or translated to produce the polypeptide. Such a nucleic acid sequence may include a coding sequence or both a coding sequence and a non-coding sequence. Thus, the terms "encode", "encoding" and the like include a RNA product resulting from transcription of a DNA molecule, a protein resulting from translation of a RNA molecule, a protein resulting from transcription of a DNA molecule to form a RNA product and the subsequent translation of the RNA product, or a protein resulting from transcription of a DNA molecule to provide a RNA product, processing of the RNA product to provide a processed RNA product (e.g., mRNA) and the subsequent translation of the processed RNA product.

By "effective amount," in the context of eliciting an immune response to a fusion protein of an enveloped virus, or complex of the fusion protein, or of treating or preventing a disease or condition, is meant the administration of an amount of agent to an individual in need thereof, either in a single dose or as part of a series, that is effective for that elicitation, treatment or prevention. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

The term "expression" and its grammatical equivalents, in the context of a gene sequence, refer to transcription of the gene to produce a RNA transcript (e.g., mRNA, antisense RNA, siRNA, shRNA, miRNA, etc.) and, as appropriate, translation of a resulting mRNA transcript to a protein. Thus, as will be clear from the context, expression of a coding sequence results from transcription and translation of the coding sequence. Conversely, expression of a non-coding sequence results from the transcription of the non-coding sequence.

As used herein, a "fusion" protein refers to two or more polypeptides coupled together which are not naturally found in a coupled arrangement.

As used herein, the term "gene" refers to a nucleic acid molecule capable of being used to produce mRNA, antisense RNA, siRNA, shRNA, miRNA, and the like, and in some embodiments, polypeptide. Genes may or may not be capable of being used to produce a functional protein. Genes can include both coding and non-coding regions (e.g., introns, regulatory elements including promoters, enhancers, termination sequences and 5' and 3' untranslated regions). A gene may be "isolated" by which is meant a nucleic acid molecule that is substantially or essentially free from components normally found in association with the nucleic acid molecule in its natural state. Such components include other cellular material, culture medium from recombinant production, and/or various chemicals used in chemically synthesizing the nucleic acid molecule. Reference to a "gene" also includes within its scope reference to genes having a contiguous sequence, thus defining contiguous nucleic acid entities, as defined herein, or a non-contiguous sequence thus defining a non-contiguous nucleic acid entity as defined herein. In certain embodiments, the term "gene" includes within its scope the open reading frame encoding specific polypeptides, introns, and adjacent 5' and 3' non-coding nucleotide sequences involved in the regulation of expression. In this regard, the gene may further comprise control sequences such as promoters, enhancers, termination and/or polyadenylation signals that are naturally associated with a given gene, or heterologous control sequences. The gene sequences may be cDNA or genomic DNA or a fragment thereof. The gene may be introduced into an appropriate vector for extrachromosomal maintenance or for introduction into a host.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA, U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

The term "IgE-mediated disorders" includes atopic disorders, which are characterized by a general inherited propensity to respond immunologically to many common naturally occurring inhaled and ingested antigens and the continual production of IgE antibodies. Examples of such disorders in which IgE plays a causal or contributing factor include allergies, asthma, anaphylaxis and food intolerances.

The term "immune suppression" as used herein refers to suppression of an immune response, e.g., in order to inhibit the development or progression of an unwanted or deleterious immune response including a pro-inflammatory immune response such as those associated with autoimmune diseases, allergies and transplantation associated diseases.

The term "immunomodulation" and its grammatical equivalents, as used herein, refer to an alteration of the immune response by augmenting (immunopotentiation) or reducing (immunosuppression) the ability of the immune system to produce antibodies or sensitized cells that recognize and react with the antigen that initiated their production.

The term "interaction", when referring to an interaction between two molecules, refers to the physical contact of the molecules with one another. Generally, such an interaction results in an activity (which produces a biological effect) of one or both of said molecules. The physical contact typically requires binding or association of the molecules with one another and may involve the formation of an induced magnetic field or paramagnetic field, covalent bond formation, ionic interaction (such as, for example, as occurs in an ionic lattice), a hydrogen bond, or alternatively, a van der Waals interaction such as, for example, a dipole-dipole interaction, dipole-induced dipole interaction, induced dipole-induced dipole interaction, or a repulsive interaction, or any combination of the above forces of attraction.

The term "neuritin polypeptide" as used herein refers to a polypeptide having an amino acid sequence corresponding to a naturally-occurring neuritin polypeptide. This term encompasses, without limitation, polypeptides having an amino acid sequence that shares at least 80% (and at least 81% to at least 99% and all integer percentages in between) sequence identity or similarity with the sequence set forth in any one of SEQ ID NOs: 2, 3 or 4 and preferably having a biological activity such as but not limited to any one or more of: promoting neurite outgrowth, modulating neurite outgrowth during neuronal differentiation, protecting motor neuron axons, promoting dendritic growth, shaping dendritic arbors of target neurons, regulating synaptic plasticity, stabilizing active synapses, promoting synaptic maturation and neuronal migration, promoting the development and maturation of visual cortical neurons, regulating apoptosis of proliferative neurons, and regenerating peripheral nerve and spinal axons, antidepressant actions, inhibition of neuronal and behavioral deficits caused by chronic stress, angiogenesis, and especially any one or more of binding to B cells (e.g., GC B cells), suppression of IgE production, inhibition of PC differentiation, and inhibiting the development or reducing the number of autoreactive B cells. It further encompasses natural allelic variation of neuritin polypeptides that may exist and occur from one organism to another. Also, degree and location of glycosylation or other post-translation modifications may vary depending on the chosen host and the nature of the hosts cellular environment. The term "neuritin polypeptide" is also intended to encompass neuritin polypeptides in their precursor form, as well as those that have been processed to yield their respective bioactive forms. It further encompasses neuritin polypeptides that have either been chemically modified relative to a reference or naturally-occurring neuritin polypeptide and/or contain one or more amino acid sequence alterations relative to a reference or naturally-occurring neuritin polypeptide and/or contain truncated amino acid sequences relative to a reference or naturally-occurring full-length or precursor neuritin polypeptide or domains thereof, including the neuritin signal peptide, mature polypeptide and pro-peptide that is removed in the mature form. The term "neuritin polypeptide" also encompasses proteinaceous molecules with a slightly modified amino acid sequence, for instance, polypeptides having a modified N-terminal end including N-terminal amino acid deletions or additions, and/or polypeptides that have been chemically modified relative to a reference or naturally-occurring neuritin polypeptide. Neuritin polypeptides also encompass proteinaceous molecules exhibiting substantially the same or better bioactivity than a reference or naturally-occurring neuritin polypeptide, or, alternatively, exhibiting substantially modified or reduced bioactivity relative to a reference or naturally-occurring neuritin polypeptide. They also include, without limitation, polypeptides having an amino acid sequence that differs from the sequence of a reference or naturally-occurring neuritin polypeptide by insertion, deletion, or substitution of one or more amino acids and in illustrative examples, encompass proteinaceous molecules that exhibit at least about 10%, 20%, 30%, 40%, 50%, 60%, 70%, 80%, 90%, 100%, 110%, 120%, and 130% of the specific activity of a reference or naturally-occurring neuritin polypeptide that has been produced in the same cell or cell type. In some embodiments, neuritin polypeptides exhibit different properties relative to a reference or naturally-occurring neuritin polypeptide, including altered (e.g., increased) stability and altered (e.g., enhanced) biological activity such as but not limited to any one or more of: promoting neurite outgrowth, modulating neurite outgrowth during neuronal differentiation, protecting motor neuron axons, promoting dendritic growth, shaping dendritic arbors of target neurons, regulating synaptic plasticity, stabilizing active synapses, promoting synaptic maturation and neuronal migration, promoting the development and maturation of visual cortical neurons, regulating apoptosis of proliferative neurons, and regenerating peripheral nerve and spinal axons, antidepressant actions, inhibition of neuronal and behavioral deficits caused by chronic stress, angiogenesis, and especially any one or more of binding to B cells (e.g., GC B cells), suppression of IgE production, inhibition of PC differentiation, and inhibiting the development or reducing the number of autoreactive B cells.

The term "operably connected" or "operably linked" as used herein refers to a juxtaposition wherein the components so described are in a relationship permitting them to function in their intended manner. For example, a regulatory sequence (e.g., a promoter) "operably linked" to a nucleotide sequence of interest (e.g., a coding and/or non-coding sequence) refers to positioning and/or orientation of the control sequence relative to the nucleotide sequence of interest to permit expression of that sequence under conditions compatible with the control sequence. The control sequences need not be contiguous with the nucleotide sequence of interest, so long as they function to direct its expression. Thus, for example, intervening non-coding sequences (e.g., untranslated, yet transcribed, sequences) can be present between a promoter and a coding sequence, and the promoter sequence can still be considered "operably linked" to the coding sequence.

The term "organ-specific autoimmune disease" as used herein refers to a disordered state of immunological regulation which contributes to pathogenesis in an affected organ, typically a single organ; and generally includes a humoral immune response against one or more organ antigens. The disordered state of immunological regulation may affect an organ selected from the group consisting of the central nervous system, peripheral nervous system, gastrointestinal tract (including small intestine, stomach and colon), thyroid, liver, lung, pancreas (exocrine and endocrine), eye, skin and reproductive organs such as breast and prostate.

The term "systemic autoimmune disease" as used herein refers to a disordered state of immunological regulation which contributes to pathogenesis in multiple affected organs, and generally includes a humoral immune response against one or more organ antigens such as DNA, cell surface molecules, collagen, and intracellular matrix proteins. The disordered state of immunological regulation may affect an organ selected from the group consisting of the skin, kidney, salivary glands, eyes, muscle, blood vessels, lung, brain and heart. Examples of such diseases include RA, SLE (and subsets of Lupus), Sjogren's syndrome (SjS), Systemic Sclerosis (SSc), Polymyositis (PM) and Dermatomyositis (DM).

The terms "patient", "subject", "host" or "individual" are used interchangeably herein to refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)), and baboon (*Papio ursinus*), as well as marmosets (species from the genus Callithrix), squirrel monkeys (species from the genus *Saimiri*) and tamarins (species from the genus *Saguinus*), as well as species of apes such as chimpanzees (Pan troglodytes), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as *canaries*, budgerigars etc.), marine mammals (e.g., dolphins, whales etc.), reptiles (snakes, frogs, lizards etc.), and fish. A preferred subject is a human in need of modulating an immune response. However, it will be understood that the aforementioned terms do not imply that symptoms are present.

By "pharmaceutically acceptable carrier" is meant a solid or liquid filler, diluent or encapsulating substance that can be safely used in topical or systemic administration to an animal, preferably a mammal, including humans. Representative pharmaceutically acceptable carriers include any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, *Remington's Pharmaceutical Sciences*, 18th Ed. Mack Printing Company, 1990, pp. 1289-1329, incorporated herein by reference). Except insofar as any conventional carrier is incompatible with the active ingredient(s), its use in the pharmaceutical compositions is contemplated.

The term "polynucleotide" or "nucleic acid" as used herein designates mRNA, RNA, cRNA, cDNA or DNA. The term typically refers to polymeric forms of nucleotides of at least 10 bases in length, either ribonucleotides or deoxynucleotides or a modified form of either type of nucleotide. The term includes single and double stranded forms of DNA.

"Polypeptide", "peptide", "protein" and "proteinaceous molecule" are used interchangeably herein to refer to molecules comprising or consisting of a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

"Regulatory elements", "regulatory sequences", "control elements", "control sequences" and the like are used interchangeably herein to refer to nucleotide sequences located upstream (5' non-coding sequences), within, or downstream (3' non-coding sequences) of a coding sequence, and which influence the transcription, RNA processing or stability, or translation of the associated coding sequence, either directly or indirectly. Regulatory elements include enhancers, promoters, translation leader sequences, introns, repetitive extragenic palindrome (REP) recognition element, intergenic regions and polyadenylation signal sequences. They include natural and synthetic sequences as well as sequences which may be a combination of synthetic and natural sequences.

By "regulatory lymphocyte" is meant a lymphocyte that is involved in regulating or suppressing responses and actions of other cells, especially of other immune cells such as B lymphocytes and T helper lymphocytes.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G and I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. The present invention contemplates the use in the methods and systems of the present invention of full-length neuritin polypeptides as well as their biologically active fragments. Typically, biologically active fragments of a full-length neuritin polypeptide may participate in an interaction, for example, an intra-molecular or an inter-molecular interaction.

"Similarity" refers to the percentage number of amino acids that are identical or constitute conservative substitutions as defined in Tables 1 and 2 supra. Similarity may be determined using sequence comparison programs such as GAP (Deveraux et al., 1984. *Nucleic Acids Research* 12: 387-395). In this way, sequences of a similar or substantially different length to those cited herein might be compared by insertion of gaps into the alignment, such gaps being determined, for example, by the comparison algorithm used by GAP.

Illustrative calculations of sequence similarity or sequence identity between sequences are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In some embodiments, the length of a reference sequence aligned for comparison purposes is at least 30%, usually at least 40%, more usually at least 50%, 60%, and even more usually at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. For amino acid sequence comparison, when a position in the first sequence is occupied by the same or similar amino acid residue (i.e., conservative substitution) at the corresponding position in the second sequence, then the molecules are similar at that position.

The percent identity between the two sequences is a function of the number of identical amino acid residues shared by the sequences at individual positions, taking into account the number of gaps, and the length of each gap, which need to be introduced for optimal alignment of the two sequences. By contrast, the percent similarity between the two sequences is a function of the number of identical and similar amino acid residues shared by the sequences at individual positions, taking into account the number of gaps, and the length of each gap, which need to be introduced for optimal alignment of the two sequences.

The comparison of sequences and determination of percent identity or percent similarity between sequences can be accomplished using a mathematical algorithm. In certain embodiments, the percent identity or similarity between amino acid sequences is determined using the Needleman and Wunsch, (1970. *J Mol Biol* 48: 444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In specific embodiments, the percent identity between nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. An non-limiting set of parameters (and the one that should be used unless otherwise specified) includes a Blossum 62 scoring matrix with a gap penalty of 12, a gap extend penalty of 4, and a frameshift gap penalty of 5.

Alternatively, the percent identity or similarity between amino acid or nucleotide sequences can be determined using the algorithm of E. Meyers and W. Miller (1989. *Cabios* 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al., 1990. *J Mol Biol* 215: 403-10. BLAST nucleotide searches can be performed with the NBLAST program, score=100, wordlength=12 to obtain nucleotide sequences homologous to 53010 nucleic acid molecules of the invention. BLAST protein searches can be performed with the XBLAST program, score=50, wordlength=3 to obtain amino acid sequences homologous to 53010 protein molecules of the invention. To obtain gapped alignments for comparison purposes, Gapped BLAST can be utilized as described in Altschul et al., 1997. *Nucleic Acids Res* 25: 3389-3402. When utilizing BLAST and Gapped BLAST programs, the default parameters of the respective programs (e.g., XBLAST and NBLAST) can be used.

Terms used to describe sequence relationships between two or more polynucleotides or polypeptides include "reference sequence," "comparison window", "sequence identity," "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997. *Nucleic Acids Res* 25:3389. A detailed discussion of sequence analysis can be found in Unit 19.3 of Ausubel et al., "Current Protocols in Molecular Biology", John Wiley & Sons Inc, 1994-1998, Chapter 15.

As used herein, the term "T helper cell" or "$T_H$ cell" refers to a sub-group of T lymphocytes involved in establishing and maximizing the capabilities of the immune system. While $T_H$ cells lack cytotoxic or phagocytic activity, they activate and direct other immune cells, including, in the case of the follicular $T_H$ subset now known as "$T_{FH}$ cells (see below), regulating the proliferation of B cells and B cell responses, B cell antibody class switching and the activation and growth of cytotoxic T cells. $T_H$ cells are also involved in maximizing the activity of phagocytes such as macrophages. Mature $T_H$ cells express the surface protein CD4, and are therefore referred to as CD4$^+$ T cells. $T_H$ cells differentiate into several major subtypes of cells known as Type 1 ($T_{H-1}$, which activate macrophages), Type 2 ($T_{H-2}$, which activate eosinophils) helper cells, $T_{H17}$ (Which activate neutrophils) and $T_{FH}$ cells, which activate B cells. In particular, $T_H$ cells play an important role in humoral immunity and immunopathology.

"Follicular helper T cells ($T_{FH}$)" are a subset of CD4$^+$ $T_H$ cells that are essential for helping cognate B cells form and maintain the GC reaction, and for extrafollicular differentiation of B cells into PCs. Thus, $T_{FH}$ cells are essential for the development of humoral immune responses. These cells are universally defined by expression of the chemokine receptor CXCR5, which directs them to the B cell follicles via gradients of the chemokine CXCL131. $T_{FH}$ cells also express the transcription factor Bcl6 (which represses Blimp-1/Prdm1) and high levels of the costimulatory receptor ICOS, which are both critical for their differentiation and maintenance. In specific embodiments, $T_{FH}$ cells include, but are not limited to the following cell surface marker phenotype: CD4$^+$ICOS$^+$CXCR5$^+$Foxp3$^-$CD19$^-$. In representative examples of this type, $T_{FH}$ cells have the following cell surface markers: CD4, CXCR5, ICOS positive and at least one marker selected from CD163, CD127, CD8a, CD89, CD197, CD161, CD6, CD229, CD96, CD272, CD148, CD107a, CD100, CD82, CD126, CD45RO, CD279, CD5, and CD99 and optionally wherein the $T_{FH}$ cells are negative for one or more of the following receptors GITR, CD25, CD162, CD27, CD95, CD9, CD43, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, IntegrinR7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86. In one embodiment, $T_{FH}$ cells have the following cell surface markers: CD4, CXCR5, ICOS positive and at least one marker selected from CD163, CD127, CD161, CD6, CD229, CD272, CD100, CD126, PD-1 (CD279), and optionally wherein the $T_{FH}$ cells are negative for one or more of the following receptors GITR, CD25, CD162, CD27, CD95, CD9, CD43, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, IntegrinR7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86. In addition, $T_{FH}$ cells secrete large amounts of IL-21, which aids in GC formation, isotype switching and PC formation. In humans and mice functionally similar $T_{FH}$ cells can be found in secondary lymphoid organs. CXCR5$^+$ $T_{FH}$ cells are also present in peripheral blood and seen at elevated levels in individuals with autoantibodies, including SLE, myasthenia gravis and juvenile DM patients.

As used herein, the terms "$T_{REG}$ cell", $T_{REG}$ and "regulatory T cell" are used interchangeably herein to refer to a naturally occurring subtype of T cell that can inhibit T cell immune responses to an antigen. $T_{REG}$ cells represent a distinct T cell lineage that has a key role in an individual's tolerance of self-antigens and the prevention of autoimmune disease and inappropriate immune responses. When activated, they are anergic and suppress the proliferation and cytokine production of conventional T cells. Like all T cells, $T_{REG}$ cells require T cell receptor activation and co-stimulation to become fully active. $T_{REG}$ cells include T cells which produce low levels of IL-2, IL-4, IL-5, and IL-12. Regulatory T cells produce TNF-α, TGFβ, IFN-γ, and IL-10, albeit at lower levels than effector T cells. Although TGFβ is the predominant cytokine produced by regulatory T cells, the cytokine is produced at levels less than or equal to that produced by $T_{H-1}$ or $T_{H-2}$ cells, e.g., an order of magnitude less than in $T_{H-1}$ or $T_{H-2}$ cells. Regulatory T cells can be found in the CD4$^+$CD25$^+$ population of cells (see, e.g., Waldmann and Cobbold, 2001. *Immunity* 14:399). Regulatory T cells actively suppress the proliferation and cytokine production of $T_{H-1}$, $T_{H-2}$, or naïve T cells which have been stimulated in culture with an activating signal (e.g., antigen and antigen presenting cells or with a signal that mimics antigen in the context of MEW, e.g., anti-CD3 antibody, plus anti-CD28 antibody). $T_{REG}$ cells have pluripotent anti-inflammatory effects on multiple cell types. In particular they control the activation of innate and adaptive immune cells. $T_{REG}$ cells acting in an antigen-specific manner reduce effector T cell activation and function, for example, after effector 'I' cells have successfully mounted an attack against an invading pathogen, or to suppress reactivity to self-antigen and thereby prevent autoimmune disease. Two subsets of $T_{REG}$ cells are classified according to the location at which they develop in vivo. Naturally occurring $T_{REG}$ (n$T_{REG}$) cells develop in the thymus and suppress self-reactive immune responses in the periphery, whereas adaptive $T_{REG}$ (a$T_{REG}$) cells develop in the periphery from conventional CD4$^+$ T cells to ensure tolerance to harmless antigens, including those derived from, for example, food and intestinal flora. Both subsets of $T_{REG}$ cells are characterized by expression of high levels of CD25 and the transcription factor Foxp3. In specific embodiments, they include the following cell surface markers CD4$^+$GITR$^+$CXCR5$^-$, or CD4$^+$Foxp3$^+$CXCR5$^-$, or CD4$^+$CD25$^{hi}$CXCR5$^-$. $T_{REG}$ cells are thought to inhibit the antigen-specific expansion and/or activation of self-reactive effector T cells and to secrete suppressive cytokines, including TGFβ or IL-10. Because of their potential to provide antigen-specific immune regulation without generalized immunosuppression, $T_{REG}$ cells have been contemplated for use in cell-based therapy for inflammatory or autoimmune disorders.

$T_{FR}$ cells are a subset of CD4$^+$CXCR5$^+$ cells which are positive for the transcription factors Foxp3, Bcl6 and Prdm1/Blimp1 and function to inhibit the GC response and prevent the selection of self-reactive GC B cells. In specific embodiments, they include the following cell surface marker phenotype: CD4$^+$ICOS$^+$CXCR5$^+$Foxp3$^+$CD19$^-$, or CD4$^+$ICOS$^+$CXCR5$^+$GITR$^+$CD19$^-$, or CD4$^+$ICOS$^+$CXCR5$^+$CD25$^{hi}$CD19$^-$. In representative examples of these embodiments, $T_{FR}$ cells have the following cell surface markers: CD4$^+$CXCR5$^+$ICOS$^+$ and at least one surface marker selected from: GITR$^+$, CD25$^{hi}$, CD162, CD27, CD95, CD9, CD43, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, IntegrinR7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86. In other representative examples, $T_{FR}$ cells have the following cell surface markers: CD4$^+$CXCR5$^+$ICOS$^+$ and at least one surface marker selected from: CD27, CD278 (ICOS), CD150, Siglec-9, CD140a, CD158b and CD33.

The term "transfected" or "transformed" or "transduced" as used herein refers to a process by which exogenous nucleic acid is transferred or introduced into a host cell. A "transfected" or "transformed" or "transduced" cell is one which has been transfected, transformed or transduced with exogenous nucleic acid. The cell includes the primary subject cell and its progeny. Transfection, transduction or transformation can be achieved by any one of a number of means including electroporation, microinjection, gene gun delivery, retroviral infection, lipofection, superfection and the like.

"Treating" or "treatment" of a state, disease, disorder or condition means an approach for obtaining beneficial or desired results, including clinical results. Beneficial or desired clinical results can include, but are not limited to, preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition, alleviation or amelioration of one or more symptoms or conditions, diminishment of extent of disease, stabilized (i.e., not worsening) state of disease (e.g., maintaining a patient in remission), preventing spread of disease, delay or slowing of disease progression, amelioration or palliation of the disease state, diminishment of the reoccurrence of disease, and remission (whether partial or total), whether detectable or undetectable, or relieving the disease, i.e., causing regression of the state, disorder or condition or at least one of its clinical or subclinical symptoms. "Treating" and "Treatment" can also mean prolonging survival as compared to expected survival if not receiving treatment, includes: the benefit to an individual to be treated is either statistically significant or at least perceptible to the patient or to the physician. "Treating" and "treatment" as used herein also include prophylactic treatment. In one embodiment, treatment methods comprise administering to a subject a therapeutically effective amount of a neuritin polypeptide and optionally consists of a single administration, or alternatively comprises a series of administrations.

By "vector" is meant a polynucleotide molecule, suitably a DNA molecule derived, for example, from a plasmid, bacteriophage, yeast or virus, into which a polynucleotide can be inserted or cloned. A vector may contain one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

As used herein, underscoring or italicizing the name of a gene shall indicate the gene, in contrast to its protein product, which is indicated by the name of the gene in the absence of any underscoring or italicizing. For example, "Nrn" shall mean the Nrn gene (e.g., Nrn-1) or Nrn polynucleotide, whereas "Nrn" or "neuritin" shall indicate the protein product or products generated from transcription and translation and alternative splicing of the "Nrn" gene (e.g., Nrn-1).

The terms "wild-type", "native" and "naturally occurring" are used interchangeably herein to refer to a gene or gene product that has the characteristics of that gene or gene product when isolated from a naturally occurring source. A wild type, native or naturally occurring gene or gene product (e.g., a polypeptide) is that which is most frequently observed in a population and is thus arbitrarily designed the "normal" or "wild-type" form of the gene or gene product.

Each embodiment described herein is to be applied mutatis mutandis to each and every embodiment unless specifically stated otherwise.

2. Neuritin Agents for Modulating Unwanted or Deleterious Immune Responses

Neuritin, also known as 0710008J23Rik, Candidate plasticity gene 15 protein (Cpg15) and Nrn, is an activity-induced glycosylphosphatidylinositol (GPI)-anchored protein, highly conserved across eukaryotes. Neuritin is mainly expressed in the brain, but it is also weakly expressed in healthy human kidney, heart, skeletal muscle and lung, and is overexpressed in gastric cancer, astrocytoma, Kaposi's sarcoma and hypoxic tumor cells. Neuritin has several effects in the nervous system, such as promoting neurite outgrowth, modulating neurite outgrowth during neuronal differentiation, protecting motor neuron axons, promoting dendritic growth, shaping dendritic arbors of target neurons, regulating synaptic plasticity, stabilizing active synapses, promoting synaptic maturation and neuronal migration, promoting the development and maturation of visual cortical neurons, regulating apoptosis of proliferative neurons, and mediating nerve growth factor (NGF)-induced peripheral nerve and spinal axons regeneration. Neuritin has antidepressant actions, blocks neuronal and behavioral deficits caused by chronic stress, and acts as an angiogenic factor. Neuritin has also been implicated in cerebral ischemia and cognitive function in schizophrenia, and can upregulate transient outward K$^+$ currents in neurons. Outside the nervous system, neuritin has been implicated in vessel pathfinding, tumorigenesis by promoting anchorage-independent growth, and liver maturation and regeneration. In accordance with the present invention, it has now been determined that neuritin is produced in $T_{FR}$ cells in the GC and at much lower amounts by conventional $T_{REG}$ cells and human $T_{FH}$ cells and binds preferentially to GC B cells, suppresses IgE production and terminal differentiation of PCs, and reduces the incidence of tissue-specific and nucleosome antibodies in the absence of $T_{FR}$ cells. Based on these findings, the present invention provides neuritin agents for use in inhibiting PC differentiation, reducing the number of autoreactive B cells, and treating, or inhibiting the development or progression of, autoreactive B cell disorders (e.g., B cell-mediated autoimmune diseases) and IgE-mediated disorders.

2.1 Neuritin Agents

Neuritin is a 142-amino acid protein containing a 27-amino acid secretory signal peptide (i.e., amino acids 1-27) at its N terminus and a 26-amino acid GPI signal peptide at its C terminus (i.e., amino acids 117-142), which are cleaved in the mature form (i.e., amino acids 28-116). Non-limiting examples of neuritin polypeptides comprise, consist or consist essentially of an amino acid sequence selected from:

(a) Human Neuritin Precursor:

[SEQ ID NO: 2]
MGLKLNGRYISLILAVQIAYLVQAVRAAGKCDAVFKGFSDCLLKLGDSM

ANYPQGLDDKTNIKTVCTYWEDFHSCTVTALTDCQEGAKDMWDKLRKES

KNLNIQGSLFELCGSGNGAAGSLLPAFPVLLVSLSAALATWLSF, as described for example in UniProt Accession No. Q9NPD7;

(b) Human neuritin minus secretory signal peptide:

[SEQ ID NO: 4]
AGKCDAVFKGFSDCLLKLGDSMANYPQGLDDKTNIKTVCTYWEDFHSCT

VTALTDCQEGAKDMWDKLRKESKNLNIQGSLFELCGSGNGAAGSLLPAF

PVLLVSLSAALATWLSF;

(c) Human neuritin minus secretory signal peptide and pro-peptide:

[SEQ ID NO: 6]
AGKCDAVFKGFSDCLLKLGDSMANYPQGLDDKTNIKTVCTYWEDFHSCT

VTALTDCQEGAKDMWDKLRKESKNLNIQGSLFELCGSGNG; and (d) an amino acid sequence corresponding to any one of the amino acid sequences set forth in SEQ ID NO: 2, 4 or 6.

The present invention also contemplates neuritin polypeptides that correspond to a wild-type or naturally-occurring neuritin polypeptide including precursor, pro-peptide and mature forms thereof processed. Such neuritin polypeptides include proteins derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein.

Neuritin polypeptides encompassed by the present invention are biologically active, that is, they continue to possess the desired biological activity of the native protein, including for example one or more activities selected from: promoting neurite outgrowth, modulating neurite outgrowth during neuronal differentiation, protecting motor neuron axons, promoting dendritic growth, shaping dendritic arbors of target neurons, regulating synaptic plasticity, stabilizing active synapses, promoting synaptic maturation and neuronal migration, promoting the development and maturation of visual cortical neurons, regulating apoptosis of proliferative neurons, and regenerating peripheral nerve and spinal axons, antidepressant actions, inhibition of neuronal and behavioral deficits caused by chronic stress, angiogenesis, and especially binding to B cells (e.g., GC B cells), suppression of IgE production, inhibition of PC differentiation, and inhibiting the development or reducing the number of autoreactive B cells. Such variants may result from, for example, genetic polymorphism or from human manipulation.

A neuritin polypeptide may be altered in various ways including amino acid substitutions, deletions, truncations, and insertions. Methods for such manipulations are generally known in the art. For example, neuritin polypeptides can be prepared by mutagenesis of a Nrn coding sequence. Methods for mutagenesis and nucleotide sequence alterations are well known in the art. See, for example, Kunkel (1985. *Proc Natl Acad Sci* 82: 488-492), Kunkel et al., (1987. *Methods in Enzymol* 154: 367-382), U.S. Pat. No. 4,873,192, Watson et al., ("Molecular Biology of the Gene", Fourth Edition, Benjamin/Cummings, Menlo Park, C A, 1987) and the references cited therein. Guidance as to appropriate amino acid substitutions that do not affect biological activity of the protein of interest may be found in the model of Dayhoff et al., (1978) *Atlas of Protein Sequence and Structure* (Natl *Biomed Res* Found, Washington, DC). Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of neuritin polypeptides. Recursive ensemble mutagenesis (REM), a technique which enhances the frequency of functional mutants in the libraries, can be used in combination with the screening assays to identify corresponding neuritin polypeptides (Arkin and Yourvan, 1992. *Proc Natl Acad Sci USA* 89: 7811-7815; Delgrave et al., 1993. *Protein Engineering* 6: 327-331). Conservative substitutions, such as exchanging one amino acid with another having similar properties, may be desirable as discussed in more detail below.

Neuritin polypeptides may contain conservative amino acid substitutions at various locations along their sequence, as compared to a parent (e.g., naturally-occurring or reference) neuritin amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/Polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al., 1978. A model of evolutionary change in proteins. Matrices for determining distance relationships. In: M. O. Dayhoff (ed.), Atlas of protein sequence and structure, vol. 5, pp. 345-358, National Biomedical Research Foundation, Washington DC; and by Gonnet et al., 1992. *Science* 256(5062):14430-1445), however, include proline in the same group as glycine, serine, alanine and threonine. Accordingly, for the purposes of the present invention, proline is classified as a "small" amino acid.

The degree of attraction or repulsion required for classification as polar or non-polar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table 1 supra.

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional neuritin polypeptide can readily be determined by assaying its activity. Conservative substitutions are shown in Table 2 supra under the heading of exemplary and preferred substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay G., Biochemistry, third edition, Wm C Brown Publishers, 1993.

Thus, a predicted non-essential amino acid residue in a naturally-occurring neuritin polypeptide is typically replaced with another amino acid residue from the same side chain family. Alternatively, mutations can be introduced randomly along all or part of a Nrn coding sequence, such as by saturation mutagenesis, and the resultant mutants can be screened for an activity of the parent polypeptide, as described for example herein, to identify mutants which retain that activity. Following mutagenesis of the coding sequences, the encoded peptide or polypeptide can be expressed recombinantly and its activity determined. A "non-essential" amino acid residue is a residue that can be altered from the wild-type sequence of an embodiment polypeptide without abolishing or substantially altering one or more of its activities, as described for example herein. Suitably, the alteration does not substantially alter one of these activities, for example, the activity is at least 20%, 40%, 60%, 70% or 80% of wild-type. Illustrative non-essential amino acid residues include any one or more of the amino acid residues that differ at the same position between the wild-type neuritin polypeptides shown in FIG. 13, for example at positions 90, 103, 112, 113, 120, 121, 122, 123, 124, 125, 126, 127, 128, 129, 130, 131 and 138. By contrast, an "essential" amino acid residue is a residue that, when altered from the wild-type sequence of a reference neuritin polypeptide, results in abolition of an activity of the parent molecule such that less than 20% of the wild-type activity is present. Non-limiting examples of essential amino acid residues may include those that are conserved in neuritin polypeptides across different species, for example at positions 1 through 89, 91 through 102, 104 through 111, 114 through 119, 132 through 137 and 138 through 142.

The present invention therefore contemplates as neuritin polypeptides, polypeptides that are distinguished from a naturally-occurring neuritin sequence by the addition, deletion, or substitution of one or more amino acid residues. In general, neuritin polypeptides will display at least about 80%, 81%, 82%, 83%, 84%, 85%, 86%, 87%, 88%, 89%, 90%, 91%, 92%, 93%, 94%, 95%, 96%, 97%, 98%, 99% similarity to a parent or reference neuritin polypeptide sequence as, for example, set forth in SEQ ID NO: 2, 4 or 6, or shown in FIG. 13 or processed forms thereof, as determined by sequence alignment programs described elsewhere herein using default parameters. Desirably, neuritin polypeptides will have at least 80%, 81%, 82%, 83%, 84%, 85%, 86%, 87%, 88%, 89%, 90%, 91%, 92%, 93%, 94%, 95%, 96%, 97%, 98%, 99% sequence identity to a parent neuritin polypeptide sequence as, for example, set forth in SEQ ID NO: 2, 4 or 6, or shown in FIG. 13 or processed forms thereof, as determined by sequence alignment programs described elsewhere herein using default parameters. Neuritin polypeptides, which fall within the scope of the present invention, may differ from a wild-type molecule generally by as much 20, 19, 18, 17, 16, 15, 14, 13, 12, or 11 amino acid residues or suitably by as few as 10, 9, 8, 7, 6, 5, 4, 3, 2, or 1 amino acid residue(s). In some embodiments, a neuritin polypeptide differs from the corresponding sequence in any one of SEQ ID NO: 2, 4 or 6, or those shown in FIG. 13 or processed forms thereof, by at least one 1% but less than or equal to 20%, 19%, 18%, 17%, 16%, 15%, 14%, 13%, 12%, 11%, 10%, 9%, 8%, 7%, 6%, 5%, 4%, 3% or 2% of the residues. If the sequence comparison requires alignment, the sequences are typically aligned for maximum similarity or identity. "Looped" out sequences from deletions or insertions, or mismatches, are generally considered differences. The differences are, suitably, differences or changes at a non-essential residue or a conservative substitution, as discussed in more detail below.

The neuritin polypeptides of the present invention also encompass neuritin polypeptides that comprise amino acids with modified side chains, incorporation of unnatural amino acid residues and/or their derivatives during protein synthesis and the use of cross-linkers and other methods which impose conformational constraints on the peptides, portions and variants of the invention. Examples of side chain modifications include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with NaBH$_4$; reductive alkylation by reaction with an aldehyde followed by reduction with NaBH$_4$; and trinitrobenzylation of amino groups with 2, 4, 6-trinitrobenzene sulfonic acid (TNBS).

The carboxyl group may be modified by carbodiimide activation via O-acylisourea formation followed by subsequent derivatization, by way of example, to a corresponding amide.

The guanidine group of arginine residues may be modified by formation of heterocyclic condensation products with reagents such as 2,3-butanedione, phenylglyoxal and glyoxal.

Sulfhydryl groups may be modified by methods such as performic acid oxidation to cysteic acid; formation of mercurial derivatives using 4-chloromercuriphenylsulfonic acid, 4-chloromercuribenzoate; 2-chloromercuri-4-nitrophenol, phenylmercury chloride, and other mercurials; formation of a mixed disulfides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulfonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. A non-limiting list of unnatural amino acids contemplated by the present invention is shown in Table 3.

TABLE 3

NON-CONVENTIONAL AMINO ACIDS
Non-Conventional Amino Acids

| | |
|---|---|
| α-aminobutyric acid | L-N-methylalanine |
| α-amino-α-methylbutyrate | L-N-methylarginine |
| aminocyclopropane-carboxylate | L-N-methylasparagine |
| aminoisobutyric acid | L-N-methylaspartic acid |
| aminonorbornyl-carboxylate | L-N-methylcysteine |
| cyclohexylalanine | L-N-methylglutamine |
| cyclopentylalanine | L-N-methylglutamic acid |
| L-N-methylisoleucine | L-N-methylhistidine |
| D-alanine | L-N-methylleucine |
| D-arginine | L-N-methyllysine |
| D-aspartic acid | L-N-methylmethionine |
| D-cysteine | L-N-methylnorleucine |
| D-glutamate | L-N-methylnorvaline |
| D-glutamic acid | L-N-methylornithine |
| D-histidine | L-N-methylphenylalanine |
| D-isoleucine | L-N-methylproline |
| D-leucine | L-N-medlylserine |
| D-lysine | L-N-methylthreonine |
| D-methionine | L-N-methyltryptophan |
| D-ornithine | L-N-methyltyrosine |
| D-phenylalanine | L-N-methylvaline |
| D-proline | L-N-methylethylglycine |
| D-serine | L-N-methyl-t-butylglycine |
| D-threonine | L-norleucine |
| D-tryptophan | L-norvaline |
| D-tyrosine | α-methyl-aminoisobutyrate |
| D-valine | α-methyl-γ-aminobutyrate |
| D-α-methylalanine | α-methylcyclohexylalanine |
| D-α-methylarginine | α-methylcylcopentylalanine |
| D-α-methylasparagine | α-methyl-α-napthylalanine |
| D-α-methylaspartate | α-methylpenicillamine |
| D-α-methylcysteine | N-(4-aminobutyl)glycine |
| D-α-methylglutamine | N-(2-aminoethyl)glycine |
| D-α-methylhistidine | N-(3-aminopropyl)glycine |
| D-α-methylisoleucine | N-amino-α-methylbutyrate |
| D-α-methylleucine | α-napthylalanine |
| D-α-methyllysine | N-benzylglycine |
| D-α-methylmethionine | N-(2-carbamylediyl)glycine |
| D-α-methylornithiine | N-(carbamylmethyl)glycine |
| D-α-methylphenylalanine | N-(2-carboxyethyl)glycine |
| D-α-methylproline | N-(carboxymethyl)glycine |
| D-α-methylserine | N-cyclobutylglycine |
| D-α-methylthreonine | N-cycloheptylglycine |
| D-α-methyltryptophan | N-cyclohexylglycine |
| D-α-methyltyrosine | N-cyclodecylglycine |
| L-α-methylleucine | L-α-methyllysine |
| L-α-methylmethionine | L-α-methylnorleucine |
| L-α-methylnorvatine | L-α-methylornithine |
| L-α-methylphenylalanine | L-α-methylproline |
| L-α-methylserine | L-α-methylthreonine |
| L-α-methyltryptophan | L-α-methyltyrosine |
| L-α-methylvaline | L-N-methylhomophenylalanine |
| N-(N-(2,2-diphenylethyl | N-(N-(3,3-diphenylpropyl |

TABLE 3-continued

NON-CONVENTIONAL AMINO ACIDS
Non-Conventional Amino Acids

| | |
|---|---|
| carbamylmethyl)glycine | carbamylmethyl)glycine |
| 1-carboxy-1-(2,2-diphenyl-ethyl amino) cyclopropane | |

The neuritin polypeptides of the present invention also include polypeptides that are encoded by polynucleotides that hybridize under stringency conditions as defined herein, especially medium or high stringency conditions, to neuritin encoding polynucleotide sequences, or the non-coding strand thereof, as described below. Illustrative Nrn polynucleotide sequences may comprise a nucleotide sequence selected from:

(a) Nrn polynucleotide encoding human neuritin precursor:

[SEQ ID NO: 1]
atgggacttaagttgaacggcagatatatttcactgatcctcgcggtgc aaatagcgtatctggtgcaggccgtgagagcagcgggcaagtgcgatgc ggtcttcaagggcttttcggactgtttgctcaagctgggcgacagcatg gccaactacccgcagggcctggacgacaagacgaacatcaagaccgtgt gcacatactgggaggatttccacagctgcacggtcacagcccttacgga ttgccaggaaggggcgaaagatatgtgggataaactgagaaaagaatcc aaaaacctcaacatccaaggcagcttattcgaactctgcggcagcggca acggggcggcggggtccctgctcccggcgttcccggtgctcctggtgtc tctctcggcagctttagcgacctggctttccttctga, as described for example in GenBank Accession No. NM_016588;

(b) Nrn polynucleotide encoding human neuritin minus secretory signal peptide:

[SEQ ID NO: 3]
gcgggcaagtgcgatgcggtcttcaagggcttttcggactgtttgctca agctgggcgacagcatggccaactacccgcagggcctggacgacaagac gaacatcaagaccgtgtgcacatactgggaggatttccacagctgcacg gtcacagcccttacggattgccaggaaggggcgaaagatatgtgggata aactgagaaaagaatccaaaaacctcaacatccaaggcagcttattcga actctgcggcagcggcaacggggcggcggggtccctgctcccggcgttc ccggtgctcctggtgtctctctcggcagctttagcgacctggctttcct tctga;

(c) Nrn polynucleotide encoding human neuritin minus secretory signal peptide and propeptide:

[SEQ ID NO: 5]
gcgggcaagtgcgatgcggtcttcaagggcttttcggactgtttgctca agctgggcgacagcatggccaactacccgcagggcctggacgacaagac gaacatcaagaccgtgtgcacatactgggaggatttccacagctgcacg gtcacagcccttacggattgccaggaaggggcgaaagatatgtggga ta -continued

```
aactgagaaaagaatccaaaaacctcaacatccaaggcagcttattcga actctgcggcagcggcaacggg; and
```

(d) a nucleotide sequence that shares at least 80% (and at least 81% to at least 99% and all integer percentages in between) sequence identity with the sequence set forth in any one of SEQ ID NO: 1, 3 or 5, or a complement thereof;

(e) a nucleotide sequence that hybridizes under at least medium or high stringency conditions to the sequence set forth in any one of SEQ ID NO: 1, 3 or 5, or a complement thereof, Variants of a reference neuritin polypeptide can be identified by screening combinatorial libraries of mutants, e.g., truncation mutants, of a neuritin polypeptide. Libraries or fragments e.g., N terminal, C terminal, or internal fragments, of a neuritin polypeptide coding sequence can be used to generate a variegated population of fragments for screening and subsequent selection of neuritin polypeptides.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of neuritin polypeptides.

The neuritin polypeptides of the present invention may be prepared by any suitable procedure known to those of skill in the art. For example, the neuritin polypeptides may be produced by any convenient method such as by purifying the peptides or polypeptides from naturally-occurring reservoirs including eukaryotes such as animals, especially vertebrate animals including mammals. Methods of purification include size exclusion, affinity or ion exchange chromatography/separation. The identity and purity of derived neuritin polypeptides is determined for example by SDS-polyacrylamide electrophoresis or chromatographically such as by high performance liquid chromatography (HPLC). Alternatively, the neuritin polypeptides may be synthesized by chemical synthesis, e.g., using solution synthesis or solid phase synthesis as described, for example, in Chapter 9 of Atherton and Shephard (supra) and in Roberge et al., 1995. Science 269:202.

In some embodiments, neuritin polypeptides are prepared by recombinant techniques. For example, the neuritin polypeptides of the invention may be prepared by a procedure including the steps of: (a) preparing a construct comprising a polynucleotide sequence that encodes a neuritin polypeptide and that is operably linked to a regulatory element; (b) introducing the construct into a host cell; (c) culturing the host cell to express the polynucleotide sequence to thereby produce the encoded neuritin polypeptide; and (d) isolating the neuritin polypeptide from the host cell. In illustrative examples, the nucleotide sequence encodes an amino acid sequence as set forth in SEQ ID NO: 2, 4 or 6, or an amino acid sequence corresponding thereto. Recombinant neuritin polypeptides can be conveniently prepared using standard protocols as described for example in Sambrook et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6.

The invention also contemplates Nrn allelic variants (same locus), homologs (different locus), and orthologs (different organism) as well as non-naturally-occurring Nrn polynucleotides. Nrn polynucleotides can contain nucleotide substitutions, deletions, inversions and insertions relative to a wild-type Nrn polynucleotide sequence. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the same amino acid sequence as a reference neuritin polypeptide sequence. Nrn nucleotide sequences also include synthetically derived nucleotide sequences, such as those generated, for example, using site-directed mutagenesis but which still encode a neuritin polypeptide. Generally, a Nrn nucleotide sequence will have at least about 80%, 81%, 82%, 83%, 84%, 85%, 86%, 87%, 88%, 89%, 90%, 91%, 92%, 93%, 94%, 95%, 96%, 97%, 98%, 99% or more sequence identity to that particular nucleotide sequence as determined by sequence alignment programs described for example herein using default parameters. In some embodiments, the Nrn nucleotide sequence displays at least about 80%, 81%, 82%, 83%, 84%, 85%, 86%, 87%, 88%, 89%, 90%, 91%, 92%, 93%, 94%, 95%, 96%, 97%, 98%, 99% or more sequence identity to a nucleotide sequence selected from any one of SEQ ID NO: 1, 3 or 5, or their complements.

Nrn nucleotide sequences can be used to isolate corresponding sequences and alleles from other organisms, particularly other mammals. Methods are readily available in the art for the hybridization of nucleic acid sequences. Coding sequences from other organisms may be isolated according to well-known techniques based on their sequence identity with the coding sequences set forth herein. In these techniques all or part of the known coding sequence is used as a probe which selectively hybridizes to other neuritin-coding sequences present in a population of cloned genomic DNA fragments or cDNA fragments (i.e., genomic or cDNA libraries) from a chosen organism (e.g., mammals). Accordingly, the present invention also contemplates polynucleotides that hybridize to reference Nrn nucleotide sequences, or to their complements, (e.g., SEQ ID NO: 1, 3 or 5, or their complements) under stringency conditions described below. As used herein, the term "hybridizes under medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used. Reference herein to medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In certain embodiments, a neuritin polypeptide is encoded by a polynucleotide that hybridizes to a disclosed nucleotide sequence under very high stringency conditions. One embodiment of very high stringency conditions includes hybridizing 0.5 M sodium phosphate, 7% SDS at 65° C., followed by one or more washes at 0.2×SSC, 1% SDS at 65° C.

Other stringency conditions are well known in the art and a skilled addressee will recognize that various factors can be manipulated to optimize the specificity of the hybridization. Optimization of the stringency of the final washes can serve to ensure a high degree of hybridization. For detailed examples, see Ausubel et al., (1994, supra) at pages 2.10.1 to 2.10.16 and Sambrook et al., (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., (1994, supra) at page 2.10.8). In general, the $T_m$ of a perfectly matched duplex of DNA may be predicted as an approximation by the formula:

$$T_m=81.5+16.6(\log_{10} M)+0.41(\% \ G+C)-0.63(\% \ \text{formamide})-(600/\text{length})$$

[0134] wherein: M is the concentration of Na$^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m$—15° C. for high stringency, or $T_m$—30° C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrrolidone and 0.1% bovine serum albumin), 0.1% SDS and 200 mg/mL denatured salmon sperm DNA) containing labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.).

The present invention also contemplates neuritin chimeric or fusion proteins. As used herein, a neuritin "chimeric protein" or "fusion protein" includes a neuritin polypeptide linked to a non-neuritin peptide or polypeptide. A "non-neuritin peptide or polypeptide" refers to a peptide or polypeptide having an amino acid sequence corresponding to a protein which is different from a neuritin polypeptide and which is synthetic or derived from the same or a different organism. The non-neuritin peptide or polypeptide can be fused to the N-terminus or C-terminus of the neuritin polypeptide. Inclusion of a cleavage site at or near the fusion junction will facilitate removal of the non-neuritin peptide or polypeptide after purification.

The fusion protein can include a moiety which has a high affinity for a ligand. For example, the fusion protein can be a GST-neuritin fusion protein in which the neuritin sequence is fused to the C-terminus of the GST sequence. Such fusion proteins can facilitate the purification of recombinant neuritin polypeptide. Other types of fusion proteins include, but are not limited to, enzymatic fusion proteins, for example beta-galactosidase fusions, yeast two-hybrid GALA fusions, poly-His fusions and immunoglobulin or other antibody fusions. Other useful fusions include linking of functional domains, such as, for example, active sites from enzymes, glycosylation domains, cellular targeting signals or transmembrane regions. In certain host cells (e.g., mammalian host cells), expression and/or secretion of a protein can be increased by using a heterologous signal sequence. Therefore, in another embodiment, the fusion protein contains a heterologous signal sequence at its N-terminus. Alternatively, or in addition, neuritin fusion proteins may include all or a part of a serum protein, e.g., an immunoglobulin (e.g., IgG) constant region, or human serum albumin.

In specific embodiments, neuritin fusion protein constructs comprise a portion of an immunoglobulin constant region. For example, the Fc portion of an immunoglobulin is useful in therapy and diagnosis and thus results, for example, in improved pharmacokinetic properties (see, for example, EP-A 0232 262). In drug discovery, for example, human proteins have been fused with Fc portions for the purpose of high-throughput screening assays to identify antagonists (Bennett et al., 1995. *J Mol Recog* 8:52-58 and Johanson et al., 1995. *J Biol Chem* 270:9459-9471). Thus, this invention also encompasses soluble fusion proteins containing an neuritin polypeptide and various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. For some uses it is desirable to remove the Fc after the fusion protein has been used for its intended purpose, for example when the fusion protein is to be used as antigen for immunizations. In a particular embodiment, the Fc part can be removed in a simple way by a cleavage sequence, which is also incorporated and can be cleaved with factor Xa. A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence.

Neuritin polypeptide may be isolated from natural sources. Typically, the neuritin polypeptides and fusion constructs of the present invention are prepared by chemical synthesis or recombinant means. In exemplary embodiments, the polypeptides are prepared by expression of a recombinant construct that encodes the neuritin polypeptide or fusion construct in suitable host cells, although any suitable methods can be used. Suitable host cells include, for example, insect cells (e.g., *Aedes aegypti, Autographa californica, Bombyx mori, Drosophila melanogaster, Spodoptera frugiperda,* and *Trichoplusia ni*), mammalian cells (e.g., human, non-human primate, horse, cow, sheep, dog, cat, and rodent (e.g., hamster)), avian cells (e.g., chicken, duck, and geese), bacteria cells (e.g., *Escherichia coli, Bacillus subtilis,* and *Streptococcus* spp.), yeast cells (e.g., *Saccharomyces cerevisiae, Candida albicans, Candida maltosa, Hansenula polymorphs, Kluyveromyces fragilis, Kluyveromyces lactis, Pichia guillerimondii, Pichia pastoris, Schizosaccharomyces pombe* and *Yarrowia lipolytica*), Tetrahymena cells (e.g., Tetrahymena thermophile) or combinations thereof. Many suitable insect cells and mammalian cells are well-known in the art. Suitable insect cells include, for example, Sf9 cells, Sf21 cells, Tn5 cells, Schneider S2 cells, and High Five cells (a clonal isolate derived from the parental *Trichoplusia ni* BTI-TN-5B1-4 cell line (Invitrogen)). Suitable mammalian cells include, for example, Chinese hamster ovary (CHO) cells, human embryonic kidney cells (HEK293 cells, typically transformed by sheared adenovirus type 5 DNA), NIH-3T3 cells, 293-T cells, Vero cells, HeLa cells, PERC.6 cells (ECACC deposit number 96022940), Hep G2 cells, MRC-5 (ATCC CCL-171), WI-38 (ATCC CCL-75), fetal rhesus lung cells (ATCC CL-160), Madin-Darby bovine kidney ("MDBK") cells, Madin-Darby canine kidney ("MDCK") cells (e.g., MDCK (NBL2), ATCC CCL34; or MDCK 33016, DSM ACC 2219), baby hamster kidney (BHK) cells, such as BHK21-F, HKCC cells, and the like. Suitable avian cells include, for example, chicken embryonic stem cells (e.g., EBx® cells), chicken embryonic fibroblasts, chicken embryonic germ cells, duck cells (e.g., AGE1.CR and AGE1.CR.pIX cell lines (ProBioGen) which are described, for example, in Vaccine 27:4975-4982 (2009) and WO2005/042728), EB66 cells, and the like.

Suitable insect cell expression systems, such as Baculovirus systems, are known to those of skill in the art and described in, e.g., Summers and Smith, Texas Agricultural Experiment Station Bulletin No. 1555,1987. Materials and methods for Baculovirus/insert cell expression systems are commercially available in kit form from, inter alia, Invitrogen, San Diego Calif. Avian cell expression systems are also known to those of skill in the art and described in, e.g., U.S. Pat. Nos. 5,340,740; 5,656,479; 5,830,510; 6,114,168; and 6,500,668; European Patent No. EP 0787180B; European Patent Application No's. EP03291813.8; WO 03/043415; and WO 03/076601. Similarly, bacterial and mammalian cell expression systems are also known in the art and described in, e.g., Yeast Genetic Engineering (Barr et al., eds., 1989) Butterworths, London.

Recombinant constructs encoding the neuritin polypeptides and fusion proteins of the present invention can be prepared in suitable vectors using conventional methods. A number of suitable vectors for expression of recombinant proteins in insect or mammalian cells are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell (e.g., of mammalian origin or from a heterologous mammalian or non-mammalian species). For example, for expression in insect cells a suitable Baculovirus expression vector, such as pFastBac (Invitrogen), can be used to produce recombinant Baculovirus particles. The Baculovirus particles are amplified and used to infect insect cells to express recombinant protein. For expression in mammalian cells, a vector that will drive expression of the construct in the desired mammalian host cell (e.g., Chinese hamster ovary cells) is used.

In some embodiments, the neuritin polypeptide compound (e.g., naked neuritin polypeptide or a neuritin fusion construct) is attached to, or enclosed or enveloped by, a macromolecular complex. The macromolecular complex can be, without limitation, a virus, a bacteriophage, a bacterium, a liposome, a microparticle, a targeting sequence, a nanoparticle (e.g., a gold nanoparticle), a magnetic bead, a yeast cell, a mammalian cell, a cell or a micro-device. These are representative examples only and macromolecular complexes within the scope of the methods and compositions described herein can include virtually any complex that can attach or enclose a neuritin polypeptide compound and be administered to a subject.

If desired, the neuritin polypeptide compound can be attached to a solid support, such as, for example, magnetic beads, Sepharose beads, agarose beads, a nitrocellulose membrane, a nylon membrane, a column chromatography matrix, a HPLC matrix or a fast performance liquid chromatography (FPLC) matrix for purification. In one embodiment, the neuritin polypeptide compound can be attached to a scaffold or other device for local and/or sustained delivery of the neuritin polypeptide compound to a selected site (e.g., a GC).

The neuritin polypeptide compounds of the present invention can be modified to improve their bioavailability, tolerance and/or stability. Illustrative modifications include for example glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Polyethylene glycol (PEG) can be conjugated to the neuritin polypeptide compounds of the invention. Pegylation can be achieved by incubation of a reactive derivative of PEG with the target macromolecule. The conjugation to PEG can be performed either enzymatically or chemically, the methods of which are well established in the art. With Pegylation the total size of a polypeptide can be increased, which reduces the chance of renal filtration and can increase the circulating half-life of the neuritin polypeptide compound. Pegylation further protects peptides from proteolytic degradation and slows the clearance from the blood. In addition, pegylation reduces immunogenicity and increases solubility of macromolecules (e.g., polypeptides). The improved pharmacokinetics by the addition of PEG is due to several different mechanisms: increase in size of the molecule, protection from proteolysis, reduced antigenicity, and the masking of specific sequences from cellular receptors.

PEG moieties useful with the compositions and methods described herein include PEG polymers, derivatives and PEG lipids. PEG polymers can be e.g., linear, branched or multi-armed, among others. The PEG conjugate according to the present invention may be of any molecular weight, for example, the molecular weight may be between 500 and 100,000 Da, between 500 and 60,000 Da, between 1000 and 40,000 Da, or between 5000 and 40,000 Da. PEGs having molecular weights of 10000 Da, 20000 Da, 30000 Da or 40000 Da may be used with the peptides or polypeptides described herein.

In addition, other polymers are also contemplated for use with the methods and compositions described herein and include, but are not limited to, poly(alkylene glycols) such as poly(propylene glycol) ("PPG"), copolymers of ethylene glycol and propylene glycol and the like, poly(oxyethylated polyol), poly(olefinic alcohol), poly(vinylpyrrolidone), poly (hydroxyalkylmethacrylamide), poly(hydroxyalkylmethacrylate), poly(saccharides), poly($\alpha$-hydroxy acid), poly(vinyl alcohol), polyphosphazene, polyoxazoline, poly(N-acryloylmorpholine), and combinations of any of the foregoing. Representative polymeric reagents and methods for conjugating these polymers to an active moiety are known in the art and further described in Zalipsky S., et al., 1992. "Use of Functionalized Poly(Ethylene Glycols) for Modification of Polypeptides". In: Polyethylene Glycol Chemistry: Biotechnical and Biomedical Applications, J. M. Harris, Plenus Press, New York, and in Zalipsky S., 1995. *Advanced Drug Reviews* 6:157-182.

The neuritin polypeptides and fusion constructs can be purified using any suitable method. Suitable methods for purifying desired proteins include precipitation and various types of chromatography, such as hydrophobic interaction, ion exchange, affinity, chelating and size exclusion are well-known in the art. Appropriate purification schemes can be created using two or more of these or other suitable methods. In specific embodiments, the neuritin polypeptide is in the form of a fusion protein or chimeric construct, which includes a purification moiety or "tag", that facilitates purification. Such tagged polypeptides can conveniently be purified, for example from conditioned media, by chelating chromatography or affinity chromatography.

The present invention also encompasses T lymphocytes (also known as T cells) from which a neuritin polypeptide coding sequence is expressible. Typically, the T lymphocytes contain a nucleic acid construct or expression vector comprising a neuritin polypeptide coding sequence in operable connection with a regulatory element, which is typically heterologous with respect to the coding sequence. Suitably, the T cells used for recombinant expression of a neuritin polypeptide coding sequence are $CD4^+$ T cells, more particularly, $T_{REG}$ cells and even more particularly, $T_{FR}$ cells.

In specific embodiments, $T_{FR}$ precursor cells, for example, $T_{REG}$ progenitor cells are derived from a mixed cell population containing such cells (e.g., from peripheral blood, tissue or organs). Preferably the mixed cell population containing $T_{FR}$ cell precursors is enriched such that $T_{FR}$ cells precursors comprise more $T_{FR}$ cells than other cell types in the population. Suitably, an enriched composition of $T_{FR}$ cells is a composition wherein the $T_{FR}$ cells make up greater than about 50% (e.g., 55%, 60%, 65%, 70%, 75%, 80%, 85%, 90%, 95%, 98%, 99%, 99.5%, 99.9% or more) of the cell population in the composition. In some embodiments, the $T_{FR}$ cells comprise about 90%, 95%, 98%, 99%, 99.5%, 99.9% or more of the cells in the composition, and such compositions are referred to herein as "highly purified" or "substantially homogenous" $T_{FR}$ cell compositions.

$T_{FR}$ cells can be enriched by targeting for selection of cell surface markers specific for immune suppressive $T_{FR}$ cells and separating using automated cell sorting such as fluorescence-activated cell sorting (FACS), solid-phase magnetic beads, etc. To enhance enrichment, positive selection may be combined with negative selection against cells comprising surface makers specific to non-T-regulatory cell types, such as depletion of CD8, CD11b, CD16, CD19, CD36 and CD56-bearing cells. In specific embodiments, $T_{FR}$ cells are sorted via flow cytometry based on surface markers of $CD4^+CXCR5^+ICOS^+GITR^+$, or $CD4^+CXCR5^+ICOS^+CD25^+$, as described for example in U.S. Patent Publication No. 2016/0032245, which is incorporated herein by reference in its entirety. In non-limiting examples of this type, $T_{FR}$ cells are sorted via flow cytometry based on the following cell surface markers: $CD4^+CXCR5^|ICOS^+$ and at least one surface marker selected from one or more of: $GITR^+$, $CD25^{hi}$, CD162, CD27, CD95, CD9, CD43, CD278, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, IntegrinR7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86.

An initial population of $T_{FR}$ cells may also be isolated from the peripheral blood of a subject and further enriched for $T_{FR}$ cells. Methods of purifying $T_{FR}$ from other PBMCs in the blood, using methods such as differential sedimentation through an appropriate medium, e.g., Ficoll-Hypaque [Pharmacia Biotech, Uppsala, Sweden], and/or methods of cell sorting, are well known and examples of such methods are described herein.

Populations of $T_{FR}$ cells may be expanded and/or activated using any suitable technique. Representative methods of expanding and/or activating T cells are described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. In specific embodiments, the $T_{FR}$ cells may be expanded and/or activated with a T cell stimulatory composition and/or in the presence of a PD-1 or PD-1L antagonist, as described for example in U.S. Patent Publication No. 2016/0032245, or with IL-2 or IL-2/anti-IL2 immune complexes as used to expand conventional $T_{REG}$ cells. If an expanding step is desired, the cells are preferably expanded at least 50-fold, and preferably at least 100, 200, 300, 500 and 800-fold.

The nucleic acid construct from which the neuritin coding sequence can be self-replicating extra-chromosomal vectors/replicons (e.g., plasmids) or vectors that integrate into a host genome. In specific embodiments, the nucleic acid constructs are viral vectors. Exemplary viral vectors include retroviral vectors, lentiviral vectors, poxvirus vectors, vaccinia virus vectors, adenovirus vectors, adenovirus-associated virus vectors, herpes virus vectors, flavivirus vectors, and alphavirus vectors. Viral vectors may be live, attenuated, replication conditional or replication deficient, and typically is a non-pathogenic (defective), replication competent viral vector.

By way of example, when the viral vector is a vaccinia virus vector, a neuritin coding sequence of the invention may be inserted into a non-essential site of a vaccinia viral vector genome. Such non-essential sites are described, for example, in Perkus et al., (1986. *Virology* 152:285); Hruby et al., (1983. *Proc Natl Acad Sci USA* 80:3411); Weir et al., (1983. *J Virol* 46:530). Suitable promoters for use with vaccinia viruses include but are not limited to P7.5 (see, e.g., Cochran et al., 1985. *J Virol* 54:30); P11 (see, e.g., Bertholet, et al., 1985. *Proc Natl Acad Sci USA* 82:2096); and CAE-1 (see, e.g., Patel et al., 1988. *Proc Natl Acad Sci USA* 85:9431). Highly attenuated strains of vaccinia are more acceptable for use in humans and include Lister, NYVAC, which contains specific genome deletions (see, e.g., Guerra et al., 2006. *J Virol* 80:985-998); Tartaglia et al., 1992. *AIDS Research and Human Retroviruses* 8:1445-1447), or MVA (see, e.g., Gheradi et al., 2005. *J Gen Virol* 86:2925-2936); Mayr et al., 1975. *Infection* 3:6-14). See also Hu et al., (2001. *J Virol* 75:10300-10308), describing use of a Yaba-Like disease virus as a vector for cancer therapy); U.S. Pat. Nos. 5,698,530 and 6,998,252. See also, e.g., U.S. Pat. No. 5,443,964. See also U.S. Pat. Nos. 7,247,615 and 7,368,116.

In certain embodiments, an adenovirus vector may be used for expressing a neuritin coding sequence. The adenovirus on which a viral transfer vector may be based may be from any origin, any subgroup, any subtype, mixture of subtypes, or any serotype. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 are available from the American Type Culture Collection (ATCC, Manassas, Va.). Non-group C adenoviruses, and even non-human adenoviruses, can be used to prepare replication-deficient adenoviral vectors. Non-group C adenoviral vectors, methods of producing non-group C adenoviral vectors, and methods of using non-group C adenoviral vectors are disclosed in, for example, U.S. Pat. Nos. 5,801,030, 5,837,511, and 5,849,561, and International Patent Applications WO 97/12986 and WO 98/53087. Any adenovirus, even a chimeric adenovirus, can be used as the source of the viral genome for an adenoviral vector. For example, a human adenovirus can be used as the source of the viral genome for a replication-deficient adenoviral vector. Further examples of adenoviral vectors can be found in Molin et al., (1998. *J Virol* 72:8358-8361), Narumi et al., (1998. *Am J Respir Cell Mol Biol* 19:936-941) Mercier et al., (2004. *Proc Natl Acad Sci USA* 101:6188-6193), U.S. Publication No's. 20150093831, 20140248305, 20120283318, 20100008889, 20090175897 and 20090088398 and U.S. Pat. Nos. 6,143,290; 6,596,535; 6,855,317; 6,936,257; 7,125,717; 7,378,087; and 7,550,296.

The viral vector can also be based on adeno-associated viruses (AAVs). For a description of AAV-based vectors, see, for example, U.S. Pat. Nos. 8,679,837, 8,637,255, 8,409,842, 7,803,622, and 7,790,449, and U.S. Publication No's. 20150065562, 20140155469, 20140037585, 20130096182, 20120100606, and 20070036757. The AAV vectors may also be self-complementary (sc) AAV vectors, which are described, for example, in U.S. Patent Publications 2007/01110724 and 2004/0029106, and U.S. Pat. Nos. 7,465,583 and 7,186,699.

Herpes simplex virus (HSV)-based viral vectors are also suitable for endogenous production of a neuritin coding sequence of the invention. Many replication-deficient HSV vectors contain a deletion to remove one or more intermediate-early genes to prevent replication. Advantages of the herpes vector are its ability to enter a latent stage that can result in long-term DNA expression, and its large viral DNA genome that can accommodate exogenous DNA up to 25 kb. For a description of HSV-based vectors, see, for example, U.S. Pat. Nos. 5,837,532, 5,846,782, 5,849,572, and 5,804,413, and International Patent Applications WO 91/02788, WO 96/04394, WO 98/15637, and WO 99/06583.

Retroviral vectors may include those based upon murine leukemia virus (MuLV), gibbon ape leukemia virus (GaLV), ecotropic retroviruses, simian immunodeficiency virus (SW), human immunodeficiency virus (HIV), and combinations (see, e.g., Buchscher et al., 1992. *J Virol* 66:2731-2739; Johann et al., 1992. *J Virol* 66:1635-1640; Sommerfelt et al., 1990. *Virology* 176:58-59; Wilson et al., 1989. *J Virol* 63:2374-2378; Miller et al., 1991. *J Virol* 65:2220-2224; Miller et al., 1990. *Mol Cell Biol* 10:4239; Kolberg, 1992. *NIH Res* 4:43; Cornetta et al., 1991. *Hum Gene Ther* 2:215).

In specific embodiments, the retroviral vector is a lentiviral vector. As would be understood by the skilled person, a viral vector, such as a lentiviral vector, generally refers to a viral vector particle that comprises the viral vector genome. For example, a lentiviral vector particle may comprise a lentiviral vector genome. With respect to lentiviral vectors, the vector genome can be derived from any of a large number of suitable, available lentiviral genome based vectors, including those identified for human gene therapy applications (see, e.g., Pfeifer et al., 2001. *Annu Rev Genomics Hum Genet* 2:177-211). Suitable lentiviral vector genomes include those based on Human Immunodeficiency Virus (HIV-1), HIV-2, feline immunodeficiency virus (FIV), equine infectious anemia virus, Simian Immunodeficiency Virus (SIV), and maedi/visna virus. A desirable characteristic of lentiviruses is that they are able to infect both dividing and non-dividing cells, although target cells need not be dividing cells or be stimulated to divide. Generally, the genome and envelope glycoproteins will be based on different viruses, such that the resulting viral vector particle is pseudotyped. Safety features of the viral vector are desirably incorporated. Safety features include self-inactivating LTR and integration deficiency as described in more detail herein. In certain embodiments integration deficiency may be conferred by elements of the vector genome but may also derive from elements of the packaging system (e.g., a non-functional integrase protein that may not be part of the vector genome but supplied in trans). Exemplary vectors contain a packaging signal (psi), a Rev-responsive element (RRE), splice donor, splice acceptor, optionally a central poly-purine tract (cPPT), and WPRE element. In certain exemplary embodiments, the viral vector genome comprises sequences from a lentivirus genome, such as the HIV-1 genome or the SIV genome. The viral genome construct may comprise sequences from the 5' and 3' LTRs of a lentivirus, and in particular may comprise the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Typically, the LTR sequences are HIV LTR sequences.

The vector genome may comprise an inactivated or self-inactivating 3' LTR (see, e.g., Zufferey et al., 1998. *J Virol* 72: 9873; Miyoshi et al., 1998. *J Virol* 72:8150). A self-inactivating vector generally has a deletion of the enhancer and promoter sequences from the 3' long terminal repeat (LTR), which is copied over into the 5' LTR during vector integration. In one instance, the U3 element of the 3' LTR contains a deletion of its enhancer sequence, the TATA box, Spl and NF-kappa B sites. As a result of the self-inactivating 3' LTR, the provirus that is generated following entry and reverse transcription will comprise an inactivated 5' LTR. The rationale is to improve safety by reducing the risk of mobilization of the vector genome and the influence of the LTR on nearby cellular promoters. The self-inactivating 3' LTR may be constructed by any method known in the art.

Optionally, the U3 sequence from the lentiviral 5' LTR may be replaced with a promoter sequence in the viral construct, such as a heterologous promoter sequence. This can increase the titer of virus recovered from the packaging cell line. An enhancer sequence may also be included. Any enhancer/promoter combination that increases expression of the viral RNA genome in the packaging cell line may be used. In one example, the CMV enhancer/promoter sequence is used (see, e.g., U.S. Pat. Nos. 5,385,839 and 5,168,062).

In certain embodiments, the risk of insertional mutagenesis is minimized by constructing the lentiviral vector to be integration defective. A variety of approaches can be pursued to produce a non-integrating vector genome. These approaches entail engineering a mutation(s) into the integrase enzyme component of the pol gene, such that it encodes a protein with an inactive integrase. The vector genome itself can be modified to prevent integration by, for example, mutating or deleting one or both attachment sites, or making the 3' LTR-proximal polypurine tract (PPT) non-functional through deletion or modification. In addition, non-genetic approaches are available; these include pharmacological agents that inhibit one or more functions of integrase. The approaches are not mutually exclusive, that is, more than one of them can be used at a time. For example, both the integrase and attachment sites can be non-functional, or the integrase and PPT site can be non-functional, or the attachment sites and PPT site can be non-functional, or all of them can be non-functional.

Exemplary lentivirus vectors are described for example in U.S. Publication No's. 20150224209, 20150203870, 20140335607, 20140248306, 20090148936 and 20080254008.

The viral vectors may also be based on an alphavirus. Alphaviruses include Sindbis virus (and Venezuelan equine encephalitis virus (VEEV)), Aura virus, Babanki virus, Barmah Forest virus, Bebaru virus, Cabassou virus, Chikungunya virus, Eastern equine encephalitis virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, O'nyong-nyong virus, Pixuna virus, Rio Negro virus, Ross River virus, Salmon pancreas disease virus, Semliki Forest virus (SFV), Southern elephant seal virus, Tonate virus, Trocara virus, Una virus, Venezuelan equine encephalitis virus, Western equine encephalitis virus, and Whataroa virus. Generally, the genome of such viruses encode nonstructural (e.g., replicon) and structural proteins (e.g., capsid and envelope) that can be translated in the cytoplasm of the host cell. Ross River virus, Sindbis virus, SFV, and VEEV have all been used to develop viral transfer vectors for transgene delivery. Pseudotyped viruses may be formed by combining alphaviral envelope glycoproteins and retroviral capsids. Examples of alphaviral vectors can be found in U.S. Publication No's. 20150050243, 20090305344 and 20060177819.

Alternatively, the viral vectors can be based on a flavivirus. Flaviviruses include Japanese encephalitis virus, Dengue virus (e.g., Dengue-1, Dengue-2, Dengue-3, Dengue-4), Yellow fever virus, Murray Valley encephalitis virus, St. Louis encephalitis virus, West Nile virus, Kunjin virus, Rocio encephalitis virus, Ilheus virus, Tick-borne encephalitis virus, Central European encephalitis virus, Siberian encephalitis virus, Russian Spring-Summer encephalitis virus, Kyasanur Forest Disease virus, Omsk Hemorrhagic fever virus, Louping ill virus, Powassan virus, Negishi virus, Absettarov virus, Hansalova virus, Apoi virus, and Hypr virus. Examples of flavivirus vectors can be found in U.S. Publication No's. 20150231226, 20150024003, 20140271708, 20140044684, 20130243812, 20120294889, 20120128713, 20110135686, 20110014229, 20110003884, 20100297167, 20100184832, 20060159704, 20060088937, 20030194801 and 20030044773.

The T cells are suitably transfected with the nucleic acid construct using any suitable technique, representative examples of which include microinjection, electroporation, calcium phosphate precipitation, liposome-mediated transfection, microprojectile bombardment and the like, or simply by contacting the cells with a viral vector as described for example above.

3. Compositions

The present invention further provides compositions, including pharmaceutical compositions, comprising a neuritin agent as broadly described above and elsewhere herein, and optionally a pharmaceutically acceptable carrier. Representative compositions may include a buffer, which is selected according to the desired use of the neuritin agent, and may also include other substances appropriate to the intended use. Where the intended use is to modulate an immune response, including a deleterious or unwanted immune response, the composition is referred to as an "immune-modulating" or "immunomodulating" composition. Such compositions include preventative compositions (i.e., compositions administered for the purpose of preventing a deleterious or unwanted immune response) and therapeutic compositions (i.e., compositions administered for the purpose of treating a deleterious or unwanted immune response). An immunomodulating composition of the present invention may therefore be administered to a recipient for prophylactic, ameliorative, palliative, or therapeutic purposes.

Those skilled in the art can readily select an appropriate buffer, a wide variety of which are known in the art, suitable for an intended use. In some instances, the composition can comprise a pharmaceutically acceptable carrier or excipient, a variety of which are known in the art and need not be discussed in detail herein. Pharmaceutically acceptable carriers or excipients have been amply described in a variety of publications, including, for example, Gennaro A., 2000. "Remington: The Science and Practice of Pharmacy", 20th edition, Lippincott, Williams, & Wilkins; Ansel et al., eds., 1999. "Pharmaceutical Dosage Forms and Drug Delivery Systems", 7.sup.th ed., Lippincott, Williams, & Wilkins; and Kibbe et al., eds., 2000. "Handbook of Pharmaceutical Excipients", $3^{rd}$ ed., American Pharmaceutical Association.

Depending on the specific condition being treated, the neuritin agents may be formulated and administered systemically, topically or locally. Suitable routes may, for example, include oral, rectal, transmucosal, or intestinal administration; parenteral delivery, including intramuscular, subcutaneous, transcutaneous, intradermal, intramedullary delivery (e.g., injection), as well as intrathecal, direct intraventricular, intravenous, intraperitoneal, intranasal, or intraocular delivery (e.g., injection). For injection, the neuritin agents of the invention may be formulated in aqueous solutions, suitably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

The neuritin agents of the present invention may be formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are familiar to those skilled in the art and include, but are not restricted to, ethoxylated and non-ethoxylated surfactants, fatty alcohols, fatty acids, hydrocarbon oils (such as palm oil, coconut oil, and mineral oil), cocoa butter waxes, silicon oils, pH balancers, cellulose derivatives, emulsifying agents such as non-ionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

Alternatively, the neuritin agents of the present invention can be formulated readily using pharmaceutically acceptable carriers or excipients well known in the art into dosages suitable for oral administration, which is also contemplated for the practice of the present invention. Such carriers enable the neuritin agents of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

Pharmaceutical formulations for parenteral administration include aqueous solutions of the particles in water-soluble form. Additionally, suspensions of the neuritin agents may be prepared as appropriate oily injection suspensions. Suitable lipophilic solvents or vehicles include fatty oils such as sesame oil, or synthetic fatty acid esters, such as ethyl oleate or triglycerides. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the neuritin agents to allow for the preparation of highly concentrated solutions.

The neuritin agents of the present invention may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients.

When T cells, including regulatory T cells such as $T_{FR}$ cells, are employed, the cells can be introduced into a patient by any means (e.g., injection), which produces the desired modified immune response. The cells may be derived from the patient (i.e., autologous cells) or from an individual or individuals who are MHC-matched or -mismatched (i.e., allogeneic) with the patient. In specific embodiments, autologous cells are injected back into the patient from whom the source cells were obtained. The injection site may be subcutaneous, intraperitoneal, intramuscular, intradermal, or intravenous. The cells may be administered to a patient already suffering from the unwanted or deleterious immune response or who is predisposed to the unwanted or deleterious immune response in sufficient number to prevent or at least partially arrest the development, or to reduce or eliminate the onset of, that response. Single or multiple administrations of the cells can be carried out with cell numbers and pattern being selected by the treating physician. The cells should be administered in a pharmaceutically acceptable carrier, which is non-toxic to the cells and the individual. Such carrier may be the growth medium in which the cells were grown, or any suitable buffering medium such as phosphate buffered saline. The cells may be administered alone or as an adjunct therapy in conjunction with other therapeutics known in the art for the treatment or prevention of unwanted immune responses for example but not limited to glucocorticoids, methotrexate, D-penicillamine, hydroxychloroquine, gold salts, sulfasalazine, TNF-α or IL-1 inhibitors, and/or other forms of specific immunotherapy.

Pharmaceutical compositions of the present invention may be provided in a kit. The kit may comprise additional components to assist in performing the methods of the present invention such as, for example, administration device(s), buffer(s), and/or diluent(s). The kits may include containers for housing the various components and instructions for using the kit components in the methods of the present invention. Typically, the kits include instructions for using the immunomodulating compositions of the present invention, either by themselves or with a companion diagnostic, as for example described herein.

4. Immunomodulatory Methods

In accordance with the present invention, neuritin agents are useful in compositions and methods for modifying an immune response, especially for inhibiting PC differentiation, reducing the number of autoreactive B cells, and treating, or inhibiting the development or progression of, autoreactive B cell disorders (e.g. a B cell-mediated autoimmune disease) and IgE-mediated disorders.

Accordingly, in one aspect, the present invention is specifically related to combatting autoreactive B-cells and the treatment or prevention of disease conditions related thereto. The autoreactive B cell disorder is a B cell autoimmune disease, or an autoimmune disease in which B cells or their products have been shown to exacerbate disease, preferably selected from the group consisting of SLE, SjS, scleroderma, RA, PM, juvenile idiopathic arthritis, graft versus host disease, DM, type I diabetes mellitus, Hashimoto's thyroiditis, Graves's disease, Addison's disease, celiac disease, Crohn's Disease, pernicious anemia, Pemphigus vulgaris, Vitiligo, autoimmune hemolytic anemia, idiopathic thrombocytopenic purpura, giant cell arteritis, Myasthenia gravis, MS, suitably relapsing-remitting MS (RRMS), glomerulonephritis, Goodpasture's syndrome, bullous pemphigoid, colitis ulcerosa, Guillain-Barre syndrome, chronic inflammatory demyelinating polyneuropathy, Anti-phospholipid syndrome, narcolepsy, sarcoidosis, Wegener's granulomatosis, type I diabetes, ulcerative colitis, and autoimmune pancreatitis.

In another aspect, the present invention relates to the treatment or prevention of IgE-mediated disorders. Representative disorders of this type include atopic disorders such as but not limited to allergic asthma, allergic rhinitis (conjunctivitis), atopic dermatitis, food allergy, anaphylaxis, contact dermatitis, allergic gastroenteropathy, allergic bronchopulmonary aspergillosis and allergic purpura (Henoch-Schonlein). Atopic patients often have multiple allergies, meaning that they have IgE antibodies to, and symptoms from, many environmental allergens, including seasonal, perennial and occupational allergens. Example seasonal allergens include pollens (e.g., grass, tree, rye, timothy, ragweed), while example perennial allergens include fungi (e.g., molds, mold spores), feathers, animal (e.g., pet or other animal dander) and insect (e.g., dust mite) debris. Example occupational allergens also include animal (e.g. mice) and plant antigens as well as drugs, detergents, metals and immunoenhancers such as isocyanates. Non-antigen specific stimuli that can result in an IgE-mediated reaction include infection, irritants such as smoke, combustion fumes, diesel exhaust particles and sulfur dioxide, exercise, cold and emotional stress. Specific hypersensitivity reactions in atopic and nonatopic individuals with a certain genetic background may result from exposure to proteins in foods (e.g., legumes, peanuts), venom (e.g., insect, snake), vaccines, hormones, antiserum, enzymes, latex, antibiotics, muscle relaxants, vitamins, cytotoxins, opiates, and polysaccharides such as dextrin, iron dextran and polygeline.

In another aspect, the present invention relates to the treatment or prevention of PC dyscrasias. PC dyscrasias (also termed PC disorders and PC proliferative diseases) are a spectrum of progressively more severe monoclonal gammopathies in which a clone or multiple clones of premalignant or malignant PCs (sometimes in association with lymphoplasmacytoid cells or B lymphocytes) over-produce a myeloma protein, i.e., an abnormal monoclonal antibody or portion thereof. A common and clinically silent disorder termed MGUS may progress to the malignant form which includes multiple myeloma, Waldenström's macroglobulinemia, or other B cell-associated neoplasms that derive stepwise from an MGUS precursor.

Other disorders associated with elevated IgE levels, that appear to be IgE-mediated and are proposed to be treatable with the formulations of this present invention include: ataxia-telangiectasia, Churg-Strauss Syndrome, eczema, enteritis, gastroenteropathy, graft-versus-host reaction, hyper-IgE (Job's) syndrome, hypersensitivity (e.g., anaphylactic hypersensitivity, candidiasis, vasculitis), IgE myeloma, inflammatory bowel disease (e.g., Crohn's disease, ulcerative colitis, indeterminate colitis and infectious colitis), mucositis (e.g., oral mucositis, gastrointestinal mucositis, nasal mucositis and proctitis), necrotizing enterocolitis and esophagitis, parasitic diseases (e.g., trypanosomiasis), hypersensitivity vasculitis, urticaria and Wiskott-Aldrich syndrome.

Additionally, disorders that may be treatable by lowering IgE levels, regardless of whether the disorders themselves are associated with elevated IgE, and thus should be considered within the scope of "IgE-mediated disorder" include: Addison's disease (chronic adrenocortical insufficiency), alopecia, hereditary angioedema, angioedema (Bannister's disease, angioneurotic edema), ankylosing spondylitis, aplastic anemia, arteritis, amyloidosis, immune disorders, such as autoimmune hemolytic anemia, autoimmune oophoritis, autoimmune orchitis, autoimmune polyendocrine failure, autoimmune hemolytic anemia, autoimmunocytopenia, autoimmune glomerulonephritis, Behcet's disease, bronchitis, Buerger's disease, bullous pemphigoid, Caplan's syndrome (rheumatoid pneumoconiosis), carditis, celiac sprue, Chediak-Higashi syndrome, chronic obstructive lung Disease (COPD), Cogan-Reese syndrome (iridocorneal endothelial syndrome), CREST syndrome, dermatitis herpetiformis (Duhring's disease), diabetes mellitus, eosinophilic fasciitis, eosinophilic nephritis, episcleritis, extrinsic allergic alveolitis, familial paroxysmal polyserositis, Felty's syndrome, fibrosing alveolitis, glomerulonephritis, Goodpasture's syndrome, granulocytopenia, granuloma, granulomatosis, granuloma myositis, Graves' disease, Guillain-Barre syndrome (polyneuritis), Hashimoto's thyroiditis (lymphadenoid goiter), hemochromatosis, histocytosis, hypereosinophilic syndrome, irritable bowel syndrome, juvenile arthritis, keratitis, leprosy, SLE, Lyell's disease, Lyme disease, mixed connective tissue disease, mononeuritis, mononeuritis multiplex, Muckle-Wells syndrome, mucocutaneous lymphoid syndrome (Kawasaki's disease), multicentric reticulohistiocytosis, MS, myasthenia gravis, mycosis fungoides, panniculitis, pemphigoid, pemphigus, pericarditis, polyneuritis, polyarteritis nodosa, psoriasis, psoriatic arthritis, pulmonary arthritis, pulmonary adenomatosis, pulmonary fibrosis, relapsing polychondritis, rheumatic fever, rheumatoid arthritis, rhinosinusitis (sinusitis), sarcoidosis, scleritis, sclerosing cholangitis, serum sickness, Sezary syndrome, SjS, Stevens-Johnson syndrome, systemic mastocytosis, transplant rejection, thrombocytopenic purpura, thymic alymphoplasia, uveitis, vitiligo, Wegener's granulomatosis.

The dosage range for the neuritin agents depends upon the potency and route of administration, and include amounts large enough to produce the desired effect, e.g., a measurable decrease in at least one symptom of a B cell autoimmune disease or an IgE-mediated disorder (e.g., an allergic response). The dosage should not be so large as to cause unacceptable adverse side effects. Generally, the dosage will vary with the particular compound used and with the age, condition, and gender of the patient. The dosage can be determined by one of skill in the art and can also be adjusted by the individual physician in the event of any complication. Typically, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 µg/kg body weight. Alternatively, the dose range will be titrated to maintain serum levels between 5 µg/mL and 30 µg/mL.

In cell therapy embodiments, the number of cells injected into the patient in need of the treatment or prophylaxis may range for example from between about $10^3$ and $10^{11}$, and usually between about $10^5$ and $10^7$ cells (e.g., T cells, including regulatory T cells such as $T_{FR}$ cells, or their precursors).

The neuritin agents of the present invention may be administered over a period of hours, days, weeks, or months, depending on several factors, including the severity of the condition being treated, whether a recurrence of the condition is considered likely, etc. The administration may be constant, e.g., constant infusion over a period of hours, days, weeks, months, etc. Alternatively, the administration may be intermittent, e.g., neuritin agents may be administered once a day over a period of days, once an hour over a period of hours, or any other such schedule as deemed suitable. The duration of treatment will typically depend upon the subject's clinical progress and responsiveness to therapy. Continuous, relatively low maintenance doses are contemplated after an initial higher therapeutic dose.

The dosage of neuritin agent administered is typically in an effective amount. An effective amount is an amount of an agent that is sufficient to produce a statistically significant, measurable change in at least one symptom of the B cell autoimmune disease or IgE-mediated disorder to be treated. Such effective amounts can be gauged in clinical trials as well as animal studies for a given neuritin agent.

Agents useful in the methods and compositions described herein can be administered by e.g., inhalation, topically, direct injection, intravenously (by bolus or continuous infusion), orally, intraperitoneally, intracavity, and can be delivered by peristaltic means, if desired, or by other means known by those skilled in the art.

Therapeutic compositions containing at least one neuritin agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The neuritin agent-containing compositions are typically administered in a manner compatible with the dosage formulation, and in an effective amount. The quantity to be administered and timing depends on the subject to be treated, capacity of the subject's system to utilize the active ingredient, and degree of therapeutic effect desired.

The efficacy of a given treatment for cell B cell-mediated autoimmune disease, PC dyscrasia, or IgE-mediated disorder can be determined by the skilled clinician. However, a treatment is considered "effective treatment", as the term is used herein, if any one or more of the signs or symptoms of cell B cell-mediated autoimmune disease (e.g., hypergammaglobulinemia, high levels of autoantibodies, antigen-antibody complex deposits in tissues, paraprotein or myeloma protein, monoclonal gammaglobulin, elevated circulating plasmablasts or PCs, etc.) or IgE-mediated disorder (e.g., allergic responses such as, but not limited to, coughing, sneezing, mucus production, rhinitis, itchy eyes, anaphylactic response to allergen, skin irritation, redness, inflammation, breathing difficulties, etc.) are altered in a beneficial manner, other clinically accepted symptoms or markers of disease are improved, or ameliorated. In one embodiment, the improvement is seen as a need for fewer anti-autoimmune (e.g., corticosteroids or immunosuppressives, etc.) or anti-allergy treatments (e.g., allergy shots, steroids, etc.), fewer episodes of hospitalization, and/or longer intervals between hospitalizations, than the individual has experienced prior to treatment with the peptide/polypeptide. Efficacy can also be measured by a failure of an individual to worsen as assessed by hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progress of a B cell-mediated autoimmune disease or IgE-mediated disorder or reaction; or (2) relieving the disease, e.g., causing regression of symptoms. The methods can also be used to prevent or reduce the likelihood of the development of a chronic condition or complication relating to a B cell-mediated autoimmune disease or IgE-mediated disorder.

5. Articles of Manufacture

The present invention also contemplates articles of manufacture that contains the subject compositions and preferably provide instructions for their use. The articles of manufacture typically comprise a container. Suitable containers include, for example, bottles, vials (e.g., dual chamber vials), syringes (such as single or dual chamber syringes) and test tubes. The containers may be formed from a variety of materials such as glass or plastic. The containers typically hold the composition. The label, which is on, or associated with the container may indicate directions for reconstitution and/or use. The label may further indicate that the composition is useful or intended for subcutaneous administration. The container holding the composition may be a multi-use vial, which allows for repeat administrations (e.g., from 2-6 administrations) of the reconstituted formulation. An article of manufacture may further comprise a second container comprising a suitable diluent. The article of manufacture may further include other materials desirable from a commercial and user standpoint, including other buffers, diluents, filters, needles, syringes, and package inserts with instructions for use.

In order that the invention may be readily understood and put into practical effect, particular preferred embodiments will now be described by way of the following non-limiting examples.

EXPERIMENTAL

Human and Mouse $T_{Fr}$ Cells are the Major Source of Neuritin in the GC

Neuritin was initially found in a microarray comparing the gene expression profile of $T_{FR}$ VS $T_{FH}$ cells in sorted cells from Foxp3-GFP reporter mice (FIG. 1A).

Nrn-1 gene expression was evaluated in T cell subsets from human and mice samples by qPCR analysis, confirming that Nrn-1 is upregulated in $T_{FR}$ cells, and to a lesser extent in $T_{REG}$ cells (FIG. 1B-C). Protein expression analyses by immunofluorescence and Western blot of sorted T cell subsets conform to previous findings where most of $T_{FR}$ cells express neuritin protein, as well as some $T_{REG}$ cells (FIG. 1D-F).

Soluble Neuritin Binds Preferentially to GC B Cells in Culture

To date, the identification of a receptor for neuritin remains elusive. It has been suggested that it might act in the signaling pathway of receptor tyrosine kinases and that blocking of the insulin receptor diminishes its effect in amplification and induction of K+ channels (Yao et al., 2012. *J Biol Chem* 287(49):41534-41545).

Given that $T_{FR}$ cells are the source of neuritin in the GC, the target cells are most likely GC B or $T_{FH}$ cells. By conjugating commercially available neuritin to a fluorophore (AF647) the present inventors were able to design an assay to track those cells that can bind neuritin in culture and analyze them by flow cytometry. In both mice and humans, neuritin bound nearly exclusively B cells. Amongst the different B cell subsets, GC B cells were found to preferentially bind neuritin in mice. On the other hand, preliminary data showed no significant differences in the capacity to bind neuritin among different B cell subsets in human (FIG. 2B-C).

Figure 2:
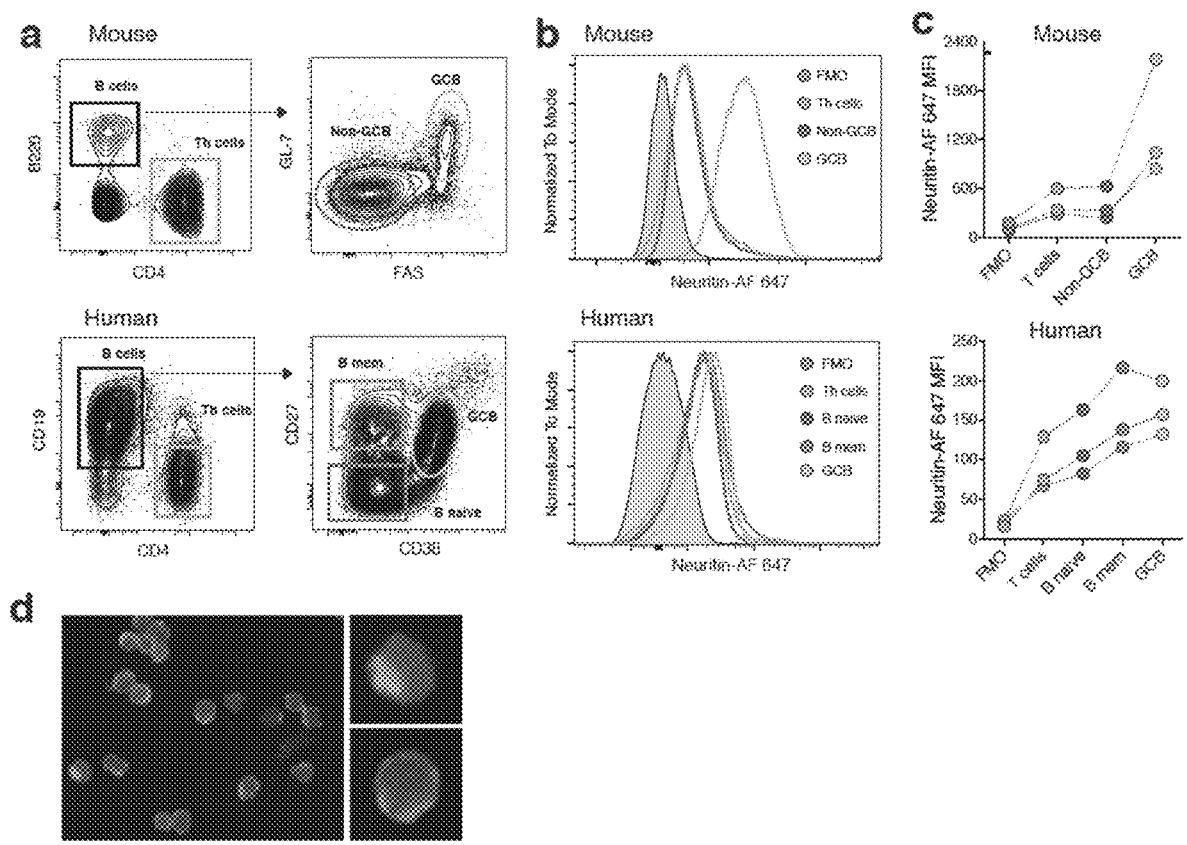
FIG. 2 is a graphical and photographic representation showing that neuritin binds preferentially to GC B cells in vitro. Human neuritin conjugated to Alexa Fluor 647 (AF647) was used to track those cells able to bind it. Single cell suspensions from mouse spleen and human tonsil were stained for B cell markers and incubated with neuritin conjugated to AF647 and analyzed by flow cytometry. The gating strategy (A), AF647 histogram (B) and mean fluorescence intensity (MFI) quantification (C) are shown for mouse and human samples. D) Cytospin immunofluorescence of sorted GC B cells stained with anti-neuritin antibody (red) and DAPI (blue).

Interestingly, although neuritin mRNA was not detected in GC B cells by qPCR (FIG. 1B-C) or RNA-seq (data not shown), GC B cells were found to stain positively for neuritin protein by immunofluorescence (FIG. 2D). This suggests that GC B cells can uptake neuritin from an external source, likely from $T_{FR}$ cells.

Localization of Neuritin$^+$ Cells in Human Tonsillar Tissue and Mouse Spleen Sections Neuritin has been shown to be highly expressed in the nervous system and in some cancer cell lines, but it has not been shown to be expressed in the immune system so far. The present inventors found that $T_{FR}$ cells express high levels of neuritin mRNA and protein.

Figure 3:
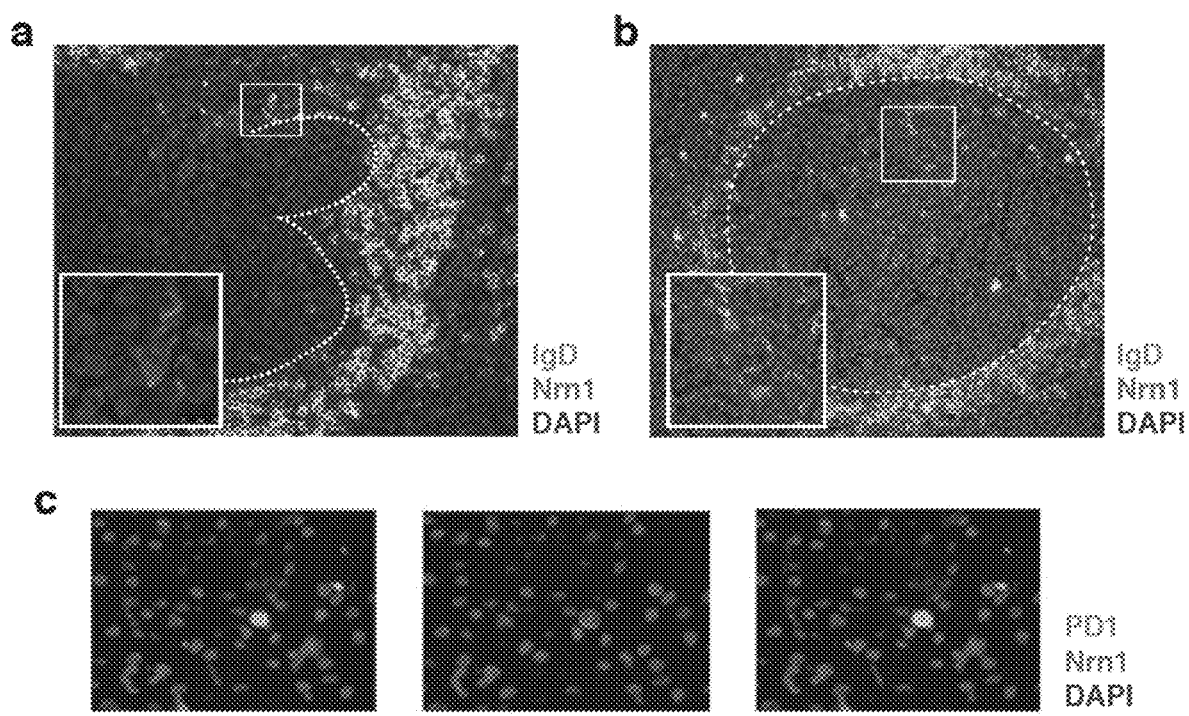
FIG. 3 is a photographic representation depicting localization of neuritin-expressing cells in germinal centers and at the T:B border of secondary lymphoid organs. Frozen sections from spleen from a sheep red blood cells (SRBC)-immunized mouse at day 6 (A) and human tonsil (B) were stained with fluorescently labeled anti-IgD (green: naïve B cells), anti-neuritin (red), and DAPI (blue). C) Human tonsillar tissue section stained with PD-1 (green), neuritin (red), and DAPI (blue).

To assess the presence of neuritin$^+$ cells in secondary lymphoid tissues, frozen sections from immunized mice and from human tonsils obtained from children undergoing routine tonsillectomy were analyzed by immunofluorescence. Sections were stained with anti-IgD antibody to delimit GCs. IgD is expressed in mature follicular naïve B cells that circumscribed the rapidly dividing IgD$^-$ GC B cells. Neuritin$^+$ cells could be seen both inside the boundaries of the GC, and at the periphery of the GC, specifically at the T:B border. Interestingly, neuritin-positive cells were often seen in contact with IgD$^+$ naïve B cells (FIG. 3) suggesting that they could have a role in screening those B cells before they enter the GC reaction. Similar results were found in human and mouse samples.

Additionally, these neuritin$^+$ cells were found to co-express PD-1, a marker highly expressed by follicular T cells (FIG. 3C).

$T_{Fr}$-Deficient and Neuritin-Deficient Mice have Normal $T_{Fh}$, $T_{Reg}$ and GC B Cell Compartments at the Peak of the GC Reaction After Bcl6$^{flox/flox}$ mice were crossed to Cre$^{Foxp3}$ to generate $T_{FR}$ deficient mice, mice were immunophenotyped to see if they had any obvious abnormalities and to confirm the absence of $T_{FR}$ cells in immunized mice.

To assess the impact of the lack of neuritin in some of the key lymphocyte compartments in vivo, Neuritin$^{flox/flox}$.Cre$^{Foxp3}$ mice were generated, which selectively lack neuritin in Foxp3-expressing T cells (i.e., $T_{REG}$ and $T_{FR}$ cells).

Importantly, the Cre$^{Foxp3}$ transgene is located in the X chromosome, which makes it susceptible to lionization. Cre transgenes are often used as heterozygous traits in case its insertion in the genome can cause unforeseen genomic disruptions. The use of females that are heterozygous for Cre could result in erratic phenotypes where some females will delete the Bcl6 gene in Foxp3-expressing cells while others will have a normal $T_{FR}$ compartment. For this reason, only male mice are chosen for the experiments.

Figure 4:
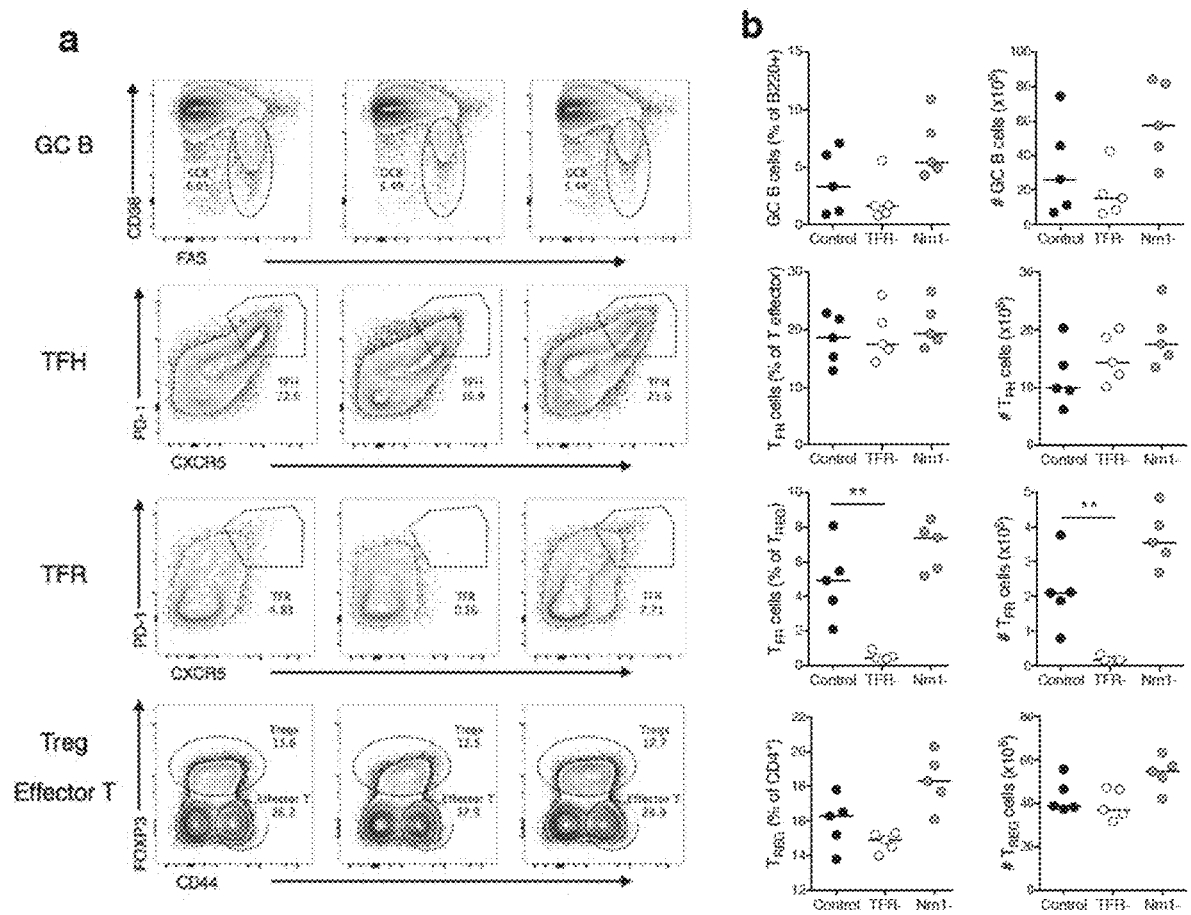
FIG. 4 is a graphical representation showing the immunophenotype of $Cre^{Foxp3}$ (control), $Bcl6^{flox/flox}.Cre^{Foxp3}$ ($T_{FR}$-deficient), and $Neuritin^{flox/flox}.Cre^{Foxp3}$ (neuritin-deficient) mice. Male mice were immunized with $2\times10^8$ SRBC intravenously and the different lymphocyte subsets were analyzed at the peak of the GC reaction (day 6) by flow cytometry. A) Representative flow cytometric plots of the different lymphocyte subsets analyzed. B) Dot plots showing proportion and total numbers of lymphocyte subsets.

Male $T_{FR}$ deficient and neuritin deficient mice showed normal number and proportion of $T_{FH}$, $T_{REG}$ and GC B cells compared to CreFoxp3 control mice. As expected, Bcl6$^{flox/flox}$.Cre$^{Foxp3}$ had a drastic reduction in $T_{FR}$ cell numbers and proportion (FIG. 4).

Figure 5:
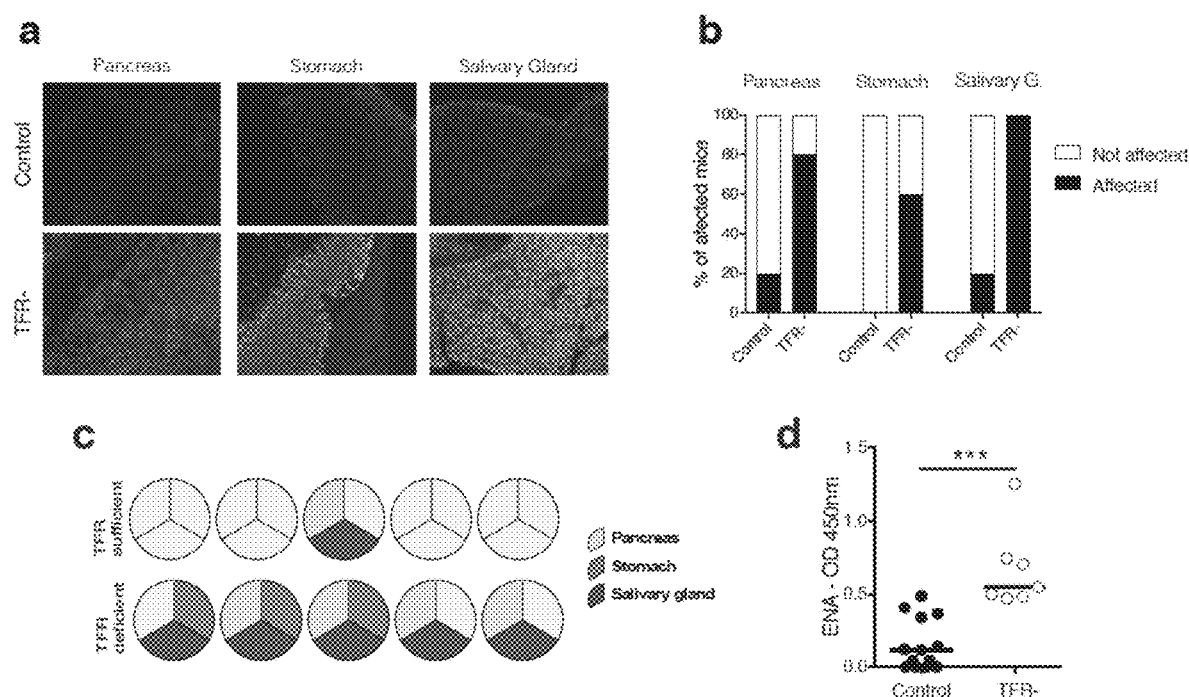
FIG. 5 is a photographic and graphical representation showing that $T_{FR}$-deficient mice develop spontaneous tissue-specific and systemic autoantibodies. A) Representative immunofluorescence images of pancreas, stomach, and salivary gland tissue cryosections from $RAG^{-/-}$ mice incubated with serum from $Bcl6^{flox/flox}.Cre^{Foxp3}$ ($T_{FR}$-deficient) or $Cre^{Foxp3}$ (control) mice followed by anti-mouse IgG conjugated to Alexa Fluor 488. B) Percentage of mice of the indicated genotype that stained positive for tissue-specific antibodies against the designated organ. C) Each circle represents an individual mouse from the indicated genotype and summarizes the pattern of tissue-specific antibodies as indicated by the color key on the right. D) Dot plot showing the quantification of circulating antibodies against extractable nuclear antigens (ENA) in control and $T_{FR}$-deficient mice by ELISA.

$T_{Fr}$ Deficient and Neuritin Deficient Mice are Prone to Develop Tissue-Specific and Nucleosome Autoantibodies The present findings have shown that mice lacking $T_{FR}$ cells spontaneously develop systemic and organ-specific autoantibodies (FIG. 5), pointing to $T_{FR}$ cells as the elusive executor of negative selection in GCs. To date, the mechanisms by which $T_{FR}$ cells exert their function are unknown.

Figure 6:
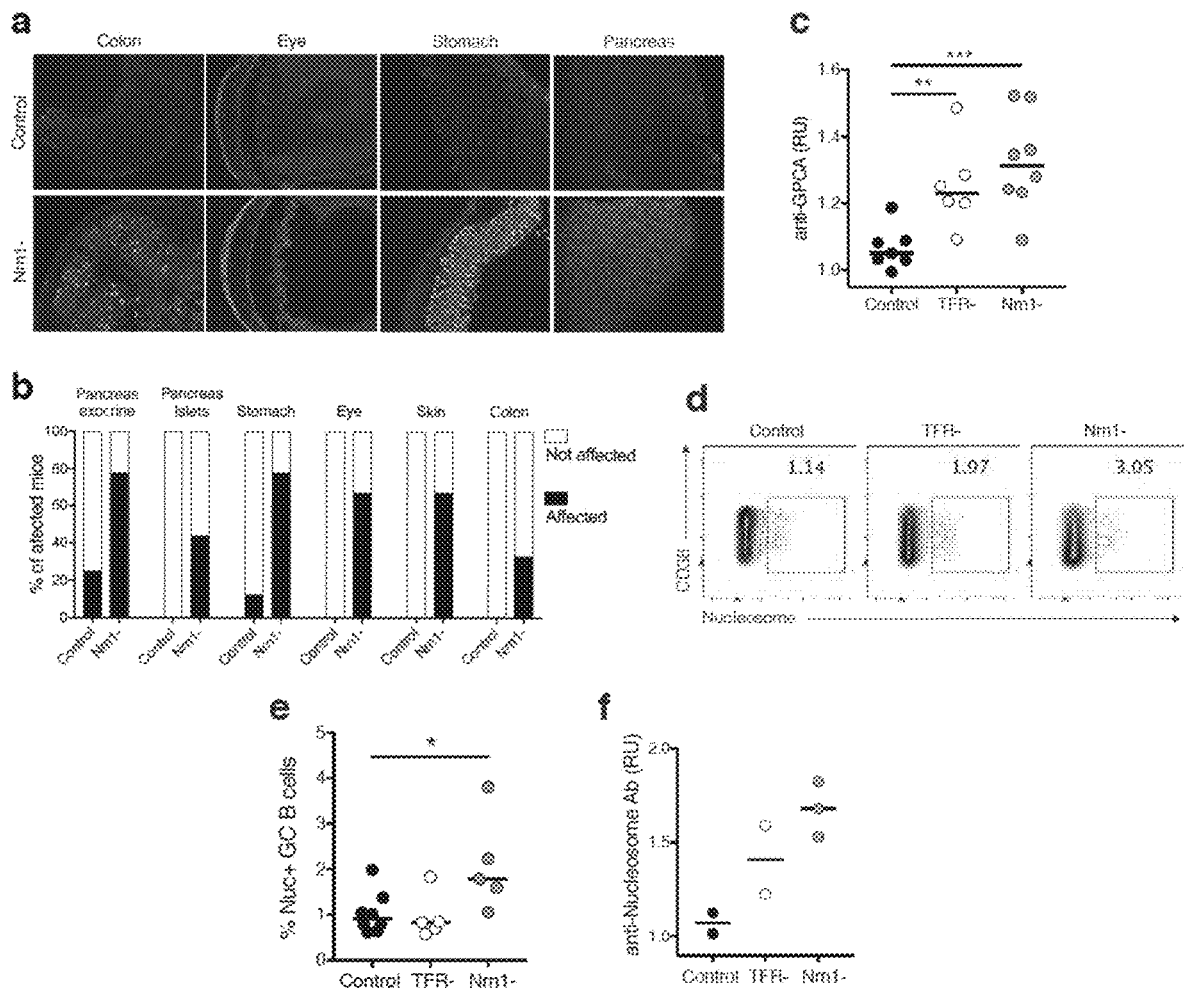
FIG. 6 is a photographic and graphical representation showing that neuritin-deficient mice develop spontaneous tissue-specific and systemic autoantibodies. A) Representative immunofluorescence images of colon, eye, stomach, and pancreas tissue cryosections from $RAG^{-/-}$ mice incubated with serum from $Neuritin^{flox/flox}.Cre^{Foxp3}$ (neuritin-deficient) or $Cre^{Foxp3}$ (control) mice followed by anti-mouse IgG conjugated to Alexa Fluor 488. B) Percentage of mice of the indicated genotype that stained positive for tissue-specific antibodies against the designated organ. C) Dot plot showing the quantification of circulating antibodies against gastric parietal cells (GPCA) in control, $T_{FR}$-deficient, and neuritin-deficient mice by ELISA. D) Flow cytometric plots and E) quantification of nucleosome-specific GC B cells in control, $T_{FR}$-deficient and neuritin-deficient mice, showing nucleosome autoantibodies are highest in neuritin-deficient mice. F) Dot plot showing the quantification of circulating antibodies against nucleosomes in control, $T_{FR}$-deficient, and neuritin-deficient mice by ELISA, again showing that nucleosome antibodies are highest in neuritin-deficient mice.

In order to test the role of neuritin, the present inventors generated mice that selectively lack neuritin in Foxp3-expressing $T_{REG}$ cells. $T_{REG}$ cells are the precursors of $T_{FR}$ cells in secondary lymphoid tissues. The results presented herein have demonstrated that $T_{REG}$-specific loss of neuritin leads to spontaneous tissue-specific (FIGS. 6A-C) and anti-nucleosome antibody production (FIG. 6D-F), suggesting that neuritin is a key mediator of $T_{FR}$-mediated protection from autoimmunity.

Neuritin Suppresses IgE Production and Terminal Differentiation of Pcs In Vitro

Neuritin in culture has been previously studied in retinal ganglion, neurons, glial, cerebellum granule, HeLa, primary embryonic hippocampal and cortical cells (Sharma et al., 2015. *Cell Death and Diseases* 6:e1661; Yao et al., 2012. *J Biol Chem* 287(49):41534-41545; Yao et al., 2016. *J Biol Chem* 291(33): 17369-17381). These studies showed an important role of neuritin in cell migration, intracellular calcium and regeneration in the context of the nervous system.

The present inventors sought to study the effect of neuritin in vitro to understand its biological relevance on GC B cells. To do this, they set up cultures using sorted human GC B cells in the presence CD40L, IL-4, and IL-21 to promote survival and differentiation, in the presence or absence of different concentrations of soluble full length neuritin. IL-13 was included in the culture media when polarization to IgE was required.

Figure 7:
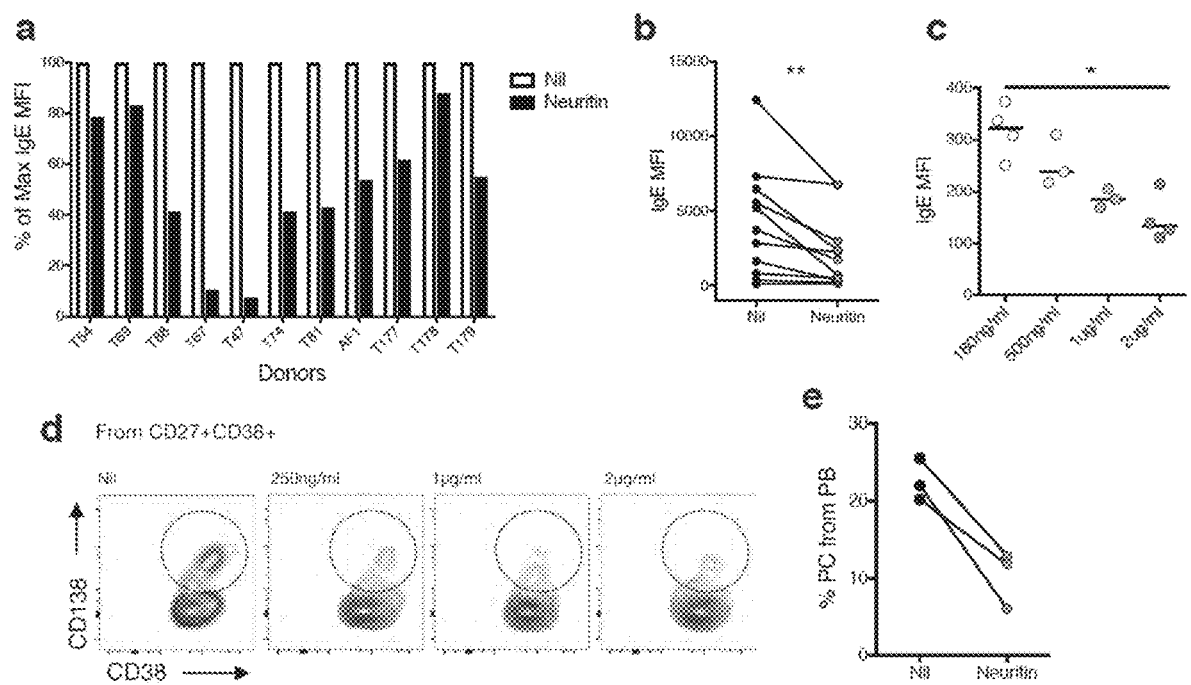
FIG. 7 is a graphical representation depicting neuritin-mediated repression of IgE production and plasma cell differentiation from human GC B cells in culture. A) IgE cytometric bead array (CBA) from the supernatant of human GC B cells treated (black bars) or untreated (white bars) with neuritin 2 μg/ml. Values are expressed as a percentage of the IgE mean fluorescence intensity (MFI) out of its respective untreated sample. B) Pooled analysis of in vitro IgE suppression assay from FIG. 7A. C) IgE cytometric bead array (CBA) from the supernatant of human GC B cell cultured five days with the indicated concentration of soluble neuritin. D) Flow cytometric plots and (F) quantification of terminally-differentiated plasma cells, as a percentage of $CD138^+$ cells from the $CD38^{hi}CD27^{hi}$ B cell gate, after culturing GC B cells five days with the designated soluble neuritin concentration.
Figure 8:
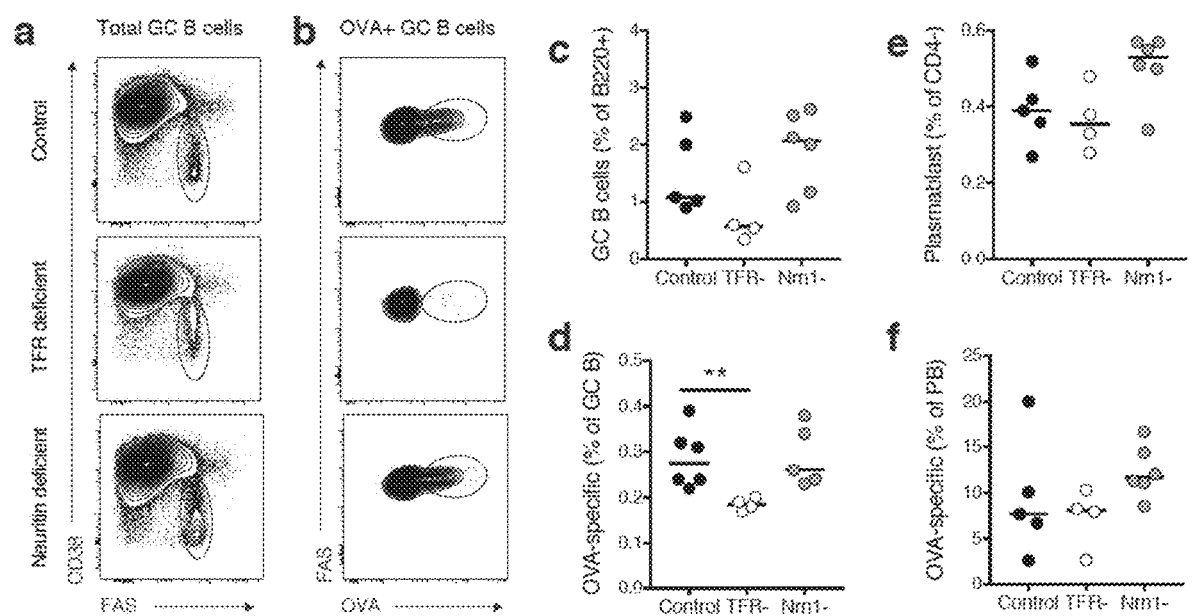
FIG. 8 is a schematic and graphical representation illustrating that GCs from $T_{FR}$-deficient mice are enriched in non-antigen-specific B cells. Mice were immunized with OVA in alum intraperitoneally on day 0 and boosted three weeks after with soluble OVA. A) Representative flow cytometric plots showing total GC B cells and (B) OVA-specific GC B cells. Dot plots showing the quantification of (C) total GC B cells ($B220^+CD38^-FAS^+$), (D) OVA-specific GC B cells ($B220^+CD38^-FAS^+OVA^+$), (E) total plasma cells ($B220^{lo}CD138^+$), and (F) OVA-specific plasma cells ($B220^{lo}CD138^+OVA^+$) in immunized control, $T_{FR}$-deficient, and neuritin-deficient mice. Lines show median values. Each dot represents data obtained from one mouse.

When culturing GC B cells in the presence of IL-13 there was a significant reduction in the amount of IgE in the supernatant of cultures treated with neuritin (FIGS. 7A-B) and this seemed to occur in a dose-dependent manner (FIG. 7C). Furthermore, a reduction in the percentage of PCs (CD138$^{hi}$) was observed in the presence of neuritin at every concentration tested (FIG. 7D-E).

Loss of $T_{Fr}$ Cells and Neuritin in the Specificity of the GC Reaction

Previous attempts to identify the role of $T_{FR}$ cells in the GC proposed that they could be involved in maintaining the dominance of antigen-specific B cell clones, ensuring that the processes of affinity maturation and selection are directed towards the immunizing antigen and preventing the maturation of an immune response against self-antigens. These attempts included cell transfers into knockout mice, which can result in high variability depending on the number of cells transferred, the time at which they are transferred, and the compatibility and possible rejection between different mouse strains.

To test whether $T_{FR}$ deficiency is relevant to generate normal antigen-specific B cell enriched GCs, $T_{FR}$-deficient (Bcl6$^{flox/flox}$.Cre$^{Foxp3}$), neuritin-deficient (Neuritin$^{flox/flox}$.Cre$^{Foxp3}$) and control mice (Bcl6$^{+/+}$.Cre$^{Foxp3}$, from now on Cre$^{Foxp3}$) were immunized with OVA in alum on day 0, boosted three weeks later and spleens were collected 5 days after boost.

The present inventors found that the absence of $T_{FR}$ cells led to a reduction in the proportion of OVA-specific cells within GC, while differences in the size of the GC were not significant (FIG. 8A-D). On the other hand, neuritin did not seem to be involved in the selection of antigen-specific GC B cells seeding the GC, since neuritin-deficient mice showed similar proportion of antigen specific B cells compared to the control. Interestingly, $T_{REG}$-derived neuritin appears to have a role in preventing plasma cell differentiation, as neuritin-deficient mice have increased proportion of plasma cells compared to control and $T_{FR}$-deficient mice (FIG. 8E-F).

Impact of Neuritin Deficiency on Ige Production In Vivo

Considering the previous findings showing a reduction in IgE production by GC B cells in culture upon neuritin treatment, the present inventors sought to evaluate IgE production in vivo in the absence of neuritin-expressing $T_{REG}$ cells. Neuritin-deficient mice (Neuritin$^{flox/flox}$ Cre$^{Foxp3}$) and control mice (Cre$^{Foxp3}$) were immunized by intraperitoneal injection of OVA precipitated in alum to induce a $T_{H-2}$ type response and thus, IgE production. Serum from immunized mice was obtained by retro-orbital bleeding and analyzed for the presence of total IgE and IgG1 in circulation.

Figure 9:
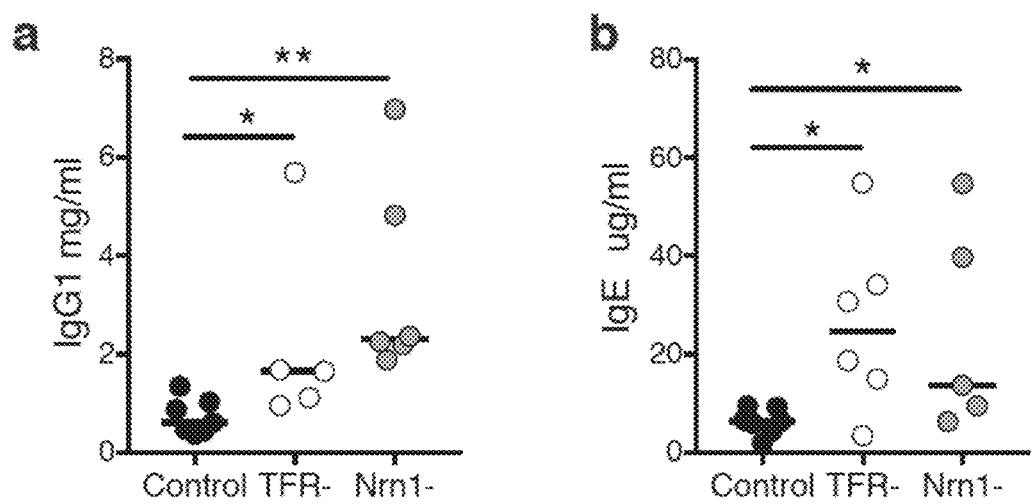
FIG. 9 is a schematic and graphical representation showing an augmented IgE and IgG1 response in neuritin-deficient mice after OVA immunization. Mice were immunized intraperitoneally on day 0 with OVA in alum and blood was collected three weeks later. A) Dot plot showing the quantification of IgG1 and (B) IgE in serum by ELISA in control, $T_{FR}$-deficient, and neuritin-deficient mice. Lines show median values. Each dot represents data obtained from one mouse.

Although, unlike $T_{FR}$-deficient mice, neuritin-deficient mice do not have elevated baseline IgE in plasma, they did show exaggerated IgE production in response to immunization (FIG. 9B).

$T_{Regs}$ from $T_{Fr}$ Deficient and Neuritin Deficient Mice have Similar Suppression Capacity Compared to Controls It has been reported that the Cre$^{Foxp3}$ allele, which encodes a Cre-YFP fusion protein, is a mild hypomorphic Foxp3 allele (Franckaert et al., 2015. *Immunol Cell Biol* 93(4): 417-423). Additionally, neuritin deletion occurs not only in $T_{FR}$ cells but also in $T_{REG}$ cells. The present inventors aimed to assessed that the different phenotypes observed in the $T_{FR}$-deficient and neuritin-deficient mice are not due to reduced Foxp3 activity and defective $T_{REG}$ function given by the lack of Bcl6 or neuritin in $T_{REG}$ cells or by the hypomorph Foxp3 present in these $T_{REG}$ cells.

Figure 10:
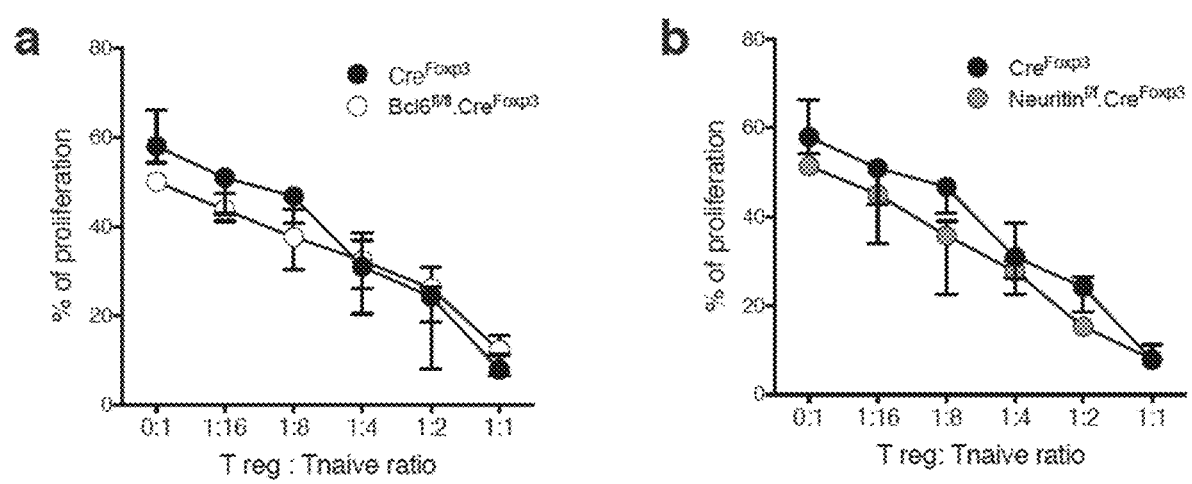
FIG. 10 is a graphical representation depicting comparable $T_{REG}$ suppression ability in $T_{REG}$ suppression assays from control, $T_{FR}$-deficient and neuritin-deficient mice. $T_{REG}$ ($B220^-CD4^+Foxp3^+CD44^{low}PD1^-$), naïve T cells ($B220^-CD4^+Foxp3^-CD44^-CD62L^+$) and pooled cells enriched in antigen presenting cells (APCs, $CD4^-$) from three mice from each genotype were sorted. Naïve T cells were pooled to evaluate the suppressive capacity of $T_{REG}$ cells from different genotypes over the same heterogeneous population. A) $T_{REG}$ suppression assay comparing control versus $T_{FR}$-deficient mice and (B) comparing control versus neuritin-deficient mice. Neither $T_{FR}$ nor neuritin deficiency impair $T_{REG}$ suppression capacity.

No significant differences were found in the suppression capacity of $T_{REG}$ cells from all genotypes tested (FIG. 10). As an additional control, the suppressive capacity of WT $T_{RE}G$ cells and $T_{REG}$ cells derived from our Cre$^{Foxp3}$ controls were compared and, again, no differences were found (data not shown).

Neuritin Treatment Reduces the Frequency of Plasma Cells in $T_{Fr}$ Deficient Mice The present inventors sought to study the potential therapeutic effect of neuritin treatment in the suppression of plasma cell (PC) differentiation in $T_{FR}$ deficient mice. $T_{FR}$ deficient mice develop an abnormal CD138$^+$PC-like GC B cell population spontaneously. The inventors hypothesized that exogenous neuritin might suppress the appearance of these PC-like GC B cells in $T_{FR}$-deficient mice.

Mice were treated eight times, twice a week with 200 μg of neuritin in PBS intravenously. After treatment, mice were sacrificed and splenic lymphocyte populations were analyzed by flow cytometry. Untreated $T_{FR}$-deficient mice and untreated control mice were used as controls.

Figure 11:
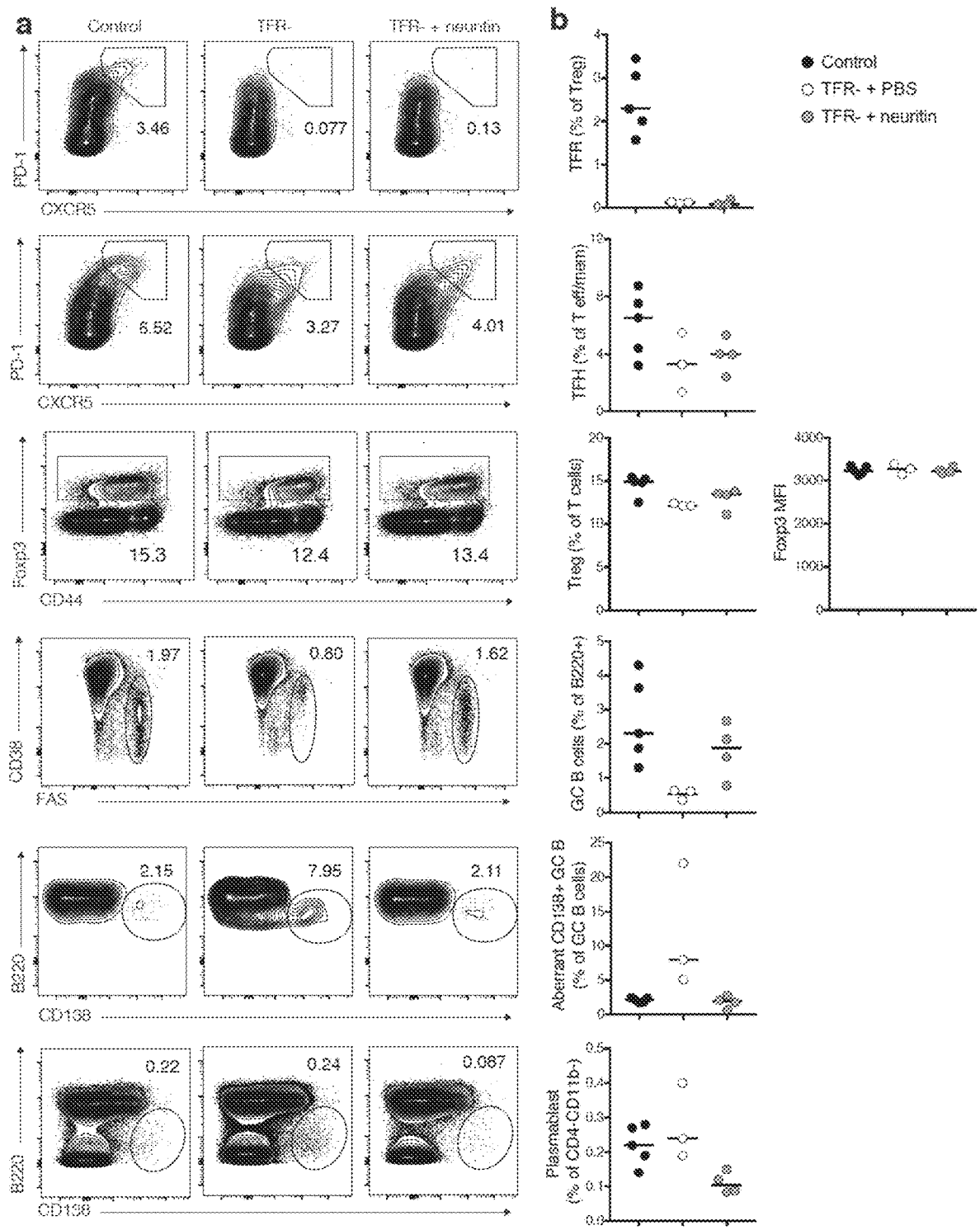
FIG. 11 is a graphical representation depicting neuritin treatment in vivo showing that neuritin eliminates the aberrant germinal center-derived plasma cell formation found in $T_{FR}$-deficient mice. $T_{FR}$-deficient mice were injected with soluble neuritin intravenously twice a week for four weeks, and lymphocyte populations were analyzed by flow cytometry. A) Representative flow cytometric plots and (B) quantification of the indicated lymphocyte population for each genotype after PBS or neuritin treatment.

Of note, this preliminary result shows that in vivo injection of neuritin is not toxic and has no obvious detrimental effect on mice overall health and longevity. Furthermore, neuritin treatment seems to have a positive effect in the control of conventional plasmablasts (B220$^{low}$CD138$^+$ B cells) and in eliminating the abnormal production of PC from GC B cells seen in $T_{FR}$-deficient mice (FIG. 11). No significant effect was observed in $T_{REG}$, $T_{FH}$ or $T_{FR}$ cells.

Neuritin Deficient Mice have Increased $T_{Reg}$ Proportion Upon Immunization

Although no proper articles have been published describing a role for neuritin in the immune system, there are two abstracts published stating that neuritin is important for Foxp3 stability and its expression in $T_{REG}$ cells is important for the persistence of these cells.

Figure 12:
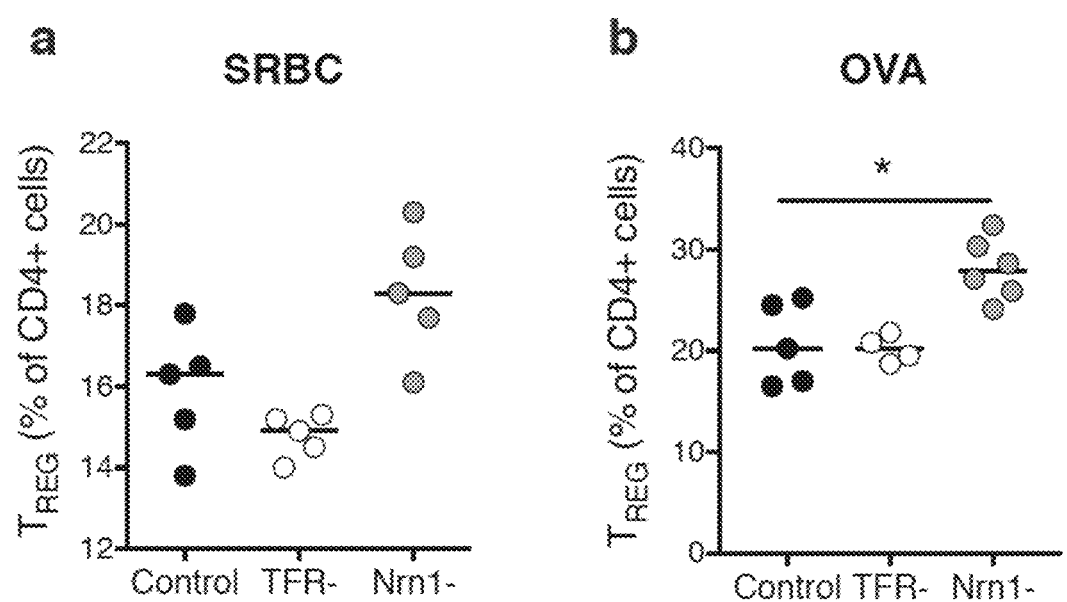
FIG. 12 is a graphical representation showing the expansion of $T_{REG}$ cells in neuritin deficient mice after immunization. Dot plots show the proportion of $T_{REG}$ cells within $CD4^+$ T cells at day 6 after SRBC immunization (A), and in mice immunized with OVA in alum intraperitoneally and boosted three weeks later (B). Lines show median values. Each dot represents data obtained from one mouse.

The present inventors demonstrate herein that neuritin loss specifically in $T_{REG}$ cells does not have a negative impact on the $T_{REG}$ pool. On the contrary, the present inventors found that in the absence of neuritin expression, $T_{REG}$ cells are expanded (FIG. 12) and their suppressive capacity is not affected (FIG. 10). The same trend of increased proportion of $T_{RE}G$ cells was observed with SRBC immunization at day 6 and with OVA in alum immunization at day 5 after boost (at day 19), however only in the latter it became significant. This trend of increased Tregs in the absence of neuritin was not observed in unimmunized mice (data not shown).

Collectively, the results presented herein indicate that intravenous administration of recombinant neuritin can target peripheral B cells to reduce potentially pathogenic antibody-producing plasma cells.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method for inhibiting plasma cell (PC) differentiation in a subject having an IgE-mediated disorder, wherein the IgE-mediated disorder is not an autoreactive B cell disorder, the method comprising administering a neuritin polypeptide to the subject, wherein a B cell of the subject is contacted with the neuritin polypeptide, to thereby inhibit PC differentiation in the subject, wherein the neuritin polypeptide is a polypeptide comprising an amino acid sequence set forth in any one of SEQ ID NO: 2, 4 and 6.

2. The method of claim 1, wherein the IgE-mediated disorder is an atopic disorder.

3. The method of claim 2, wherein the atopic disorder is selected from the group consisting of allergic asthma, allergic rhinitis, allergic conjunctivitis, atopic dermatitis, food allergy, anaphylaxis, contact dermatitis, allergic gastroenteropathy, allergic bronchopulmonary aspergillosis, allergic purpura, and Henoch-Schonlein purpura.

4. The method of claim 1, wherein the IgE-mediated disorder is an allergy.

5. The method of claim 4, wherein the allergy is associated with an environmental allergen selected from the group consisting of seasonal, perennial and occupational allergens.

6. The method of claim 4, wherein the allergy is associated with a seasonal allergen, wherein the seasonal allergen is a pollen.

7. The method of claim 4, wherein the allergy is associated with a perennial allergen, wherein the perennial allergen is selected from the group consisting of fungi, feathers, animal debris and insect debris.

8. The method of claim 4, wherein the allergy is associated with an occupational allergen, wherein the occupational allergen is selected from the group consisting of animal antigens, plant antigens, drugs, detergents, metals and immunoenhancers.

9. The method of claim 1, wherein the IgE-mediated disorder is selected from the group consisting of ataxia-telangiectasia, Churg-Strauss Syndrome, eczema, enteritis, gastroenteropathy, graft-versus-host reaction, hyper-IgE (Job's) syndrome, hypersensitivity, IgE myeloma, indeterminate colitis, infectious colitis, mucositis, necrotizing enterocolitis and esophagitis, parasitic diseases, hypersensitivity vasculitis, urticaria and Wiskott-Aldrich syndrome.

10. The method of claim 1, wherein the neuritin polypeptide is linked to all or part of an immunoglobulin constant region.

11. The method of claim 1, wherein the neuritin polypeptide is conjugated to a polymer.

12. The method of claim 11, wherein the polymer is a polyethylene glycol.

13. The method of claim 1, wherein the neuritin polypeptide is a naked neuritin polypeptide.

14. The method of claim 1, wherein the neuritin polypeptide is a chimeric polypeptide.

* * * * *